US011225514B2

(12) United States Patent
Hammock et al.

(10) Patent No.: US 11,225,514 B2
(45) Date of Patent: Jan. 18, 2022

(54) NANOBODIES AGAINST CYSTIC FIBROSIS TRANSMEMBRANE CONDUCTANCE REGULATOR (CFTR) INHIBITORY FACTOR (CIF)

(71) Applicants: THE REGENTS OF THE UNIVERSITY OF CALIFORNIA, Oakland, CA (US); THE TRUSTEES OF DARTMOUTH COLLEGE, Hanover, NH (US)

(72) Inventors: Bruce D. Hammock, Davis, CA (US); Natalia Vasylieva, Davis, CA (US); Jiexian Dong, Davis, CA (US); Christophe Morisseau, West Sacramento, CA (US); Dean R. Madden, Hanover, NH (US)

(73) Assignees: THE REGENTS OF THE UNIVERSITY OF CALIFORNIA, Oakland, CA (US); THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 16/616,930

(22) PCT Filed: May 29, 2018

(86) PCT No.: PCT/US2018/034878
§ 371 (c)(1),
(2) Date: Nov. 25, 2019

(87) PCT Pub. No.: WO2018/222587
PCT Pub. Date: Dec. 6, 2018

(65) Prior Publication Data
US 2020/0231659 A1 Jul. 23, 2020

Related U.S. Application Data

(60) Provisional application No. 62/512,711, filed on May 30, 2017.

(51) Int. Cl.
*C07K 16/12* (2006.01)
*G01N 33/569* (2006.01)
*C07K 16/40* (2006.01)

(52) U.S. Cl.
CPC .......... *C07K 16/1214* (2013.01); *C07K 16/40* (2013.01); *G01N 33/56911* (2013.01); *C07K 2317/22* (2013.01); *C07K 2317/569* (2013.01); *C07K 2317/76* (2013.01); *C07K 2317/92* (2013.01); *G01N 2333/21* (2013.01)

(58) Field of Classification Search
None
See application file for complete search history.

(56) References Cited

U.S. PATENT DOCUMENTS

2010/0197593 A1 8/2010 Stanton et al.
2015/0045389 A1 2/2015 Madden et al.

FOREIGN PATENT DOCUMENTS

| WO | WO-1994004678 A1 | 3/1994 |
| WO | WO-1999037681 A2 | 7/1999 |
| WO | WO-2000043507 A1 | 7/2000 |
| WO | WO-2001090190 A2 | 11/2001 |
| WO | WO-2002085945 A2 | 10/2002 |
| WO | WO-2003025020 A1 | 3/2003 |
| WO | WO-2003035694 A2 | 5/2003 |
| WO | WO-2004049794 A2 | 6/2004 |
| WO | WO-2007035092 A2 | 3/2007 |
| WO | WO-2013155047 A2 | 10/2013 |

OTHER PUBLICATIONS

Cui et al. Anal Bioanal Chem. 407(24): 7275-7283, 2015.*
Tibary et al. Theriogenology 66: 633-647, 2006.*
Sura et al. J. Vet. Diagn. Invest. 20: 349-352, 2008.*
Iglewski B. Medical Microbiology, 4th Edition, Chapter 27, pp. 1-11, 1996.*
Bahl et al., "Pseudomonas aeruginosa Cif defines a distinct class of alpha/beta epoxide hydrolases utilizing a His/Tyr ring-opening pair", Protein Pept Lett., Feb. 1, 2012, vol. 19, No. 2, pp. 186-193.
Bahl et al., "Crystal Structure of the Cystic Fibrosis Transmembrane Conductance Regulator Inhibitory Factor Cif Reveals Novel Active-Site Features of an Epoxide Hydrolase Virulence.Factor" Journal of Bacteriology, Apr. 2010, vol. 192, pp. 1785-1795.
Bahl et al.,"Inhibiting an epoxide hydrolase virulence protects CFTR", Angew Chem Int Ed Engl, Aug. 17, 2015, vol. 54, No. 34, pp. 9881-9885.
Bahl et al., "The cif Virulence Factor is Present in Keratitis patient Isolates of Pseudomonas aeruginosa", Cornea, Mar. 2017, vol. 36, No. 3, pp. 358-362.
Barbas, "Phage Display: A Laboratory Manual", Cold Spring Harbor Laboratory Press, 2001, 2 pages. Abstract Description.
Barlow et al., "Substrate-dependent modulation of enzyme activity by allosteric effector antibodies", Biochimica et Biophysica Acta, 2009, No. 1794, pp. 1259-1268.
Bever et al., "Development and Utilization of Camelid VHH Antibodies from Alpaca for 2,2',4,4'-Tetrabrominated Diphenyl Ether Detection", Analytical Chemistry, 2014, vol. 86, pp. 7875-7882.
Bever et al., "VHH antibodies: Emerging reagents for the analysis of environmental chemicals", Anal Bioanal Chem, 2016, vol. 408, No. 22, pp. 5985-6002.
Buelens et al., "Generation and characterization of inhibitory nanobodies towards thrombin activatable fibrinolysis inhibitor", Journal of Thrombosis and Haemostasis, 2010, vol. 8, pp. 1302-1312.
Chen et al., "Smartphone-interfaced lab-on-a-chip devices for field-deployable enzyme-linked immunosorbent assay", Biomicrofluidics, 2014, vol. 8, 064101-1-064101-11.

(Continued)

*Primary Examiner* — Sarvamangala Devi
(74) *Attorney, Agent, or Firm* — Mintz, Levin, Cohn, Ferris, Glovsky & Popeo, P.C.

(57) ABSTRACT

Provided are VHH or nanobodies that specifically bind to cystic fibrosis transmembrane conductance regulator (CFTR) inhibitory factor (Cif), and uses thereof for diagnosis and treatment of *Pseudomonas* infection.

19 Claims, 9 Drawing Sheets

Specification includes a Sequence Listing.

(56) References Cited

OTHER PUBLICATIONS

Comor et al., "Joining the in vitro immunization of alpaca lymphocytes and phage display: raid and cost effective pipeline for sdAb synthesis", Microbial Cell Factories, 2017, vol. 16:13, 13 pages.
Cui et al., "Heavy Chain Single Domain Antibodies to Detect Native Human Soluble Epoxide Hydrolase", Anal Bioanal Chem., Sep. 2015, vol. 407, No. 24, pp. 7275-7283.
Dmitriev et al., "Nanobodies as Probes for Protein Dynamics in Vitro and in Cells", The Journal of Biological Chemistry, Feb. 19, 2016, vol. 291, pp. 3767-3775.
Dolk et al., "Isolation of Llama Antibody Fragments for Prevention of Dandruff by Phage Display in Shampoo", Applied and Environmental Microbiology, Jan. 2005, vol. 71, No. 1, pp. 442-450.
Donato et al., "Fluorescence-based assays forscreening nine cytochrome P450 (P450) activities in intact cells expressing individual human P450 enzymes", Drug Metabolism and Disposition, 2004, vol. 32, pp. 699-706.
Flitter et al., "Pseudomonas aeruginosa sabotages the generation of host proresolving lipid mediators", P Natl Acad Sci USA, Jan. 3, 2017, vol. 114, No. I, pp. 136-141.
Fowler et al., "An evaluation of fluorescence polarization and lifetime discriminated polarization for high throughput screening of serine/threonine kinases", Analytical Biochemistry, 2002, vol. 308, pp. 223-231.
Frenken et al., "Isolation of antigen specific Llama $V_{HH}$ antibody fragments and their high level secretion by *Saccharomyces cerevisiae*". Journal of Biotechnology, 2000, vol. 78, pp. 11-21.
Ghannam et al., "Camelid nanobodies with high affinity for broad bean mottle virus: a possible promising tool to immunomodulate plant resistance against viruses", Plant Mol Biol, 2015, vol. 87, pp. 355-369.
Glickman et al., "Scintillation Proximity Assays in High-Throughput Screening", Asay and Drug Develpment Technologies, Nov. 3, 2008, vol. 6, No. 3, pp. 433-455.
Hamers-Casterman et al., "Naturally occurring antibodies devoid of light chains", Nature, Jun. 3, 993, vol. 363, pp. 446-448.
Harmsen et al., "Properties, production, and applications of camelid single-domain antibody fragments", Appl. Microbiol. Biotechnol., 2007, vol. 77, No. 1, pp. 13-22.
Hoogenboom, "Selecting and screening recombinant antibody libraries", Nature Biotechnology, 2005, vol. 23, No. 9, pp. 1105-1116.
International Search Report for OCT/US2018/034878 dated Oct. 15, 2018, 5 pages.
Jahnichen et al., "CXCR4 nanobodies (VHH-based single variable domains) potently inhibit chemotaxis and HIV-1 replication and mobilize stem cells", P Natl Acad Sci USA, Nov. 23, 2010, vol. 107, No. 47, pp. 20565-20570.
Jiang et al. "Generation of a phage-display library of single-domain camelid $V_H$Hs binding cell-surface antigens", The Plant Journal, 2013, vol. 76, pp. 709-717.
Joosten et al., "Production of bifunctional proteins by Aspergillus awamori: Llama variable heavy chain antibody fragment ($V_{HH}$) R9 coupled to Arthromyces ramosus peroxidase (ARP)", Journal of Biotechnology, 2005, vol. 120, pp. 347-359.
Kitamura et al., "Rational Design of Potent and Selective Inhibitors of an Epoxide Hydrolase Virulence Factor from Pseudomonas aeruginosa", Journal of Medicinal Chemistry, 2016, vol. 59, pp. 4790-4799.
Klooster et al., "Selection of VHH Antibody Fragments That Recognize Different A β Depositions Using Complex Immune Libraries", Methods in Molecular Biology, 2012, vol. 911, pp. 241-253.
Koh et al., "Generation of a Family-specific Phage Library of Llama Single Chain antibody Fragments That Neutralize HIV-1*", The Journal Biological Chemistry, Jun. 18, 2010, vol. 285, No. 25, pp. 19116-19124.
Lea et al., "Fluorescence Polarization Assays in Small Molecule Screening", Expert Opin Drug Discov, Jan. 2011, vol. 6, No. 1, pp. 17-32.
Lorimer et al., "Recombinant immunotoxins specific for a mutant epidermal growth factor receptor: Targeting with a single chain antibody variable domain isolated by phage display", Proc. Nat'l Acad. Sci. USA, Dec. 1996, vol. 93, 14815-14820.
MacEachran et al., "The Pseudomonas aeruginosa Secreted Protein PA2934 Decreases Apical Membrane Expression of the Cystic Fibrosis Transmembrane Conductance Regulator", Infection and Immunity, Aug. 2007, vol. 75, No. 8, pp. 3902-3912.
Maussang et al., "Llama-derived Single Variable Domains (Nanobodies) Directed against Chemokine Receptor CXCR7 Reduce Head and Neck Cancer Cell Growth in Vivo", The Journal Biological Chemistry, Oct. 11, 2013, vol. 288, No. 41, pp. 29562-29572.
Menzel et al., "The art of blocking ADP-ribosyltransferases (ARTs): nanobodies as experimental and therapeutic tools to block mammalian and toxin ARTs", The FEBS journal 280, 3543-3550, doi:10.1111/febs.12313 (2013).
Möller et al., "Intracellular Activation of Interferon Regulatory factor-1 by Nanobodies to the Multifunctional (Mf1) Domain", The Journal of Biological Chemistry, Dec. 3, 2010, vol. 285, No. 49, pp. 38348-38361.
Morisseau et al., "Development of fluorescent substrates for microsomal epoxide hydrolase and application to inhibition studies", Analytical Biochemistry, 2011, vol. 414, pp. 154-162.
Nakayama et al., "Characterization and Selection of 3-(1-Naphthoyl)-Indole Derivative-Specific Alpaca VHH Antibodies Using a Phage Display Library", Monoclonal Antibodies Immunodiagnosis and Immunotherapy, 2016, vol. 35, No. 4, pp. 231-234.
Nam et al., "Active-site MMP-selective antibody inhibitors discovered from convex paratope synthetic libraries", P Natl Acad Sci USA, Dec. 27, 2016, vol. 113, No. 52, pp. 14970-14975.
Obishakin et al., "Generation of a Nanobody Targeting the Paraflagellar Rod Protein of Trypanosomes", PLOS One, Dec. 31, 2014, 17 pages.
Oyen et al., "Constraining Enzyme Conformational Change by an Antibody Leads to Hyperbolic Inhibition", Journal of Molecular Biology, 2011, vol. 407, pp. 138-148.
Qin et al., "A high-throughput inhibition screening of major human cytochrome P450 enzymes using an in vitro cocktail and liquid chromatography-tandem mass spectrometry", Biomedical Chromatography, 2014, vol. 28, pp. 197-203.
Rahbarizadeh et al., "Over expression of anti-MUC1 single-domain antibody fragments in the yeast *Pichia pastoris*", Molecular Immunology, 2006 vol. 43, pp. 426-435.
Rossotti et al., "A method for sorting and pairwise selection of nanobodies for the development of highly sensitive sandwich immunoassays", Anal Chem, Dec. 1, 2015, vol. 87, No. 23, pp. 11907-11914.
Sabir et al., "Construction of naïve camelids VHH repertoire in phage display-based library", Comptes Rendus Biologies, 2014, vol. 337, pp. 244-249.
Schmitz et al., "Structural evaluation of EGFR inhibition mechanisms for nanobodies/VHH domains", Structure, 2013, vol. 21, No. 7, pp. 1214-1224.
Sohier et al., "Allosteric inhibition of VIM metallo-β-lactamases by a camelid nanobody", Biochem J, 2013, vol. 450, pp. 477-486.
Stanfield et al., "Crystal Structure of a Shark Single-Domain Antibody V Region in Complex with Lysozyme", Science, Sep. 17, 2004, vol. 305, pp. 1770-1773.
Tabares-Da Rosa et al., "Competitive Selection from Single Domain Antibody Libraries Allows Isolation of High-Affinity Antihapten Antibodies That Are Not Favored in the llama Immune Response", Analytical Chemistry, Sep. 15, 2011, vol. 83, pp. 7213-7220.
Tian et al., "A high throughput drug screen based on fluorescence resonance energy transfer (FRET) for anticancer activity of compounds from herbal medicine", British Journal of Pharmacology, 2007, vol. 150, pp. 321-334.
Turek-Etienne et al., "Use of Red-Shifted Dyes in a Fluorescence Polarization AKT Kinase Assay for Detection of Biological Activity in Natural Product Extracts", Journal of Biomolecular Screening, 2004, vol. 9, No. 1, pp. 52-61.
Unger et al., "Selection of Nanobodies that Block the Enzymatic and Cytotoxic Activities of the Binary Clostridium Difficile Toxin CDT", Scientific Reports, 2015, 5:7805, 10 pages.

(56) References Cited

OTHER PUBLICATIONS

Von Ahsen et al., "High-Throughput Screening for Kinase Inhibitors", ChemBioChem, 2005, vol. 6, pp. 481-490.
Wang et al., "Heterologous Antigen Selection of Camelid Heavy Chain Single Domain Antibodies against Tetrabromobisphenol A", Analytical Chemistry, 2014, vol. 86, pp. 8296-8302.
Wesolowski et al., "Single domain antibodies: promising experimental and therapeutic tools in infection and immunity", Med Microbiol Immunol, 2009, vol. 198, pp. 157-174.
Written Opinion of the International Searching Authority for PCT/US2018/034878 dated Oct. 15, 2018, 10 pages.
Wu et al., "Application of Scintillation Proximity Assay in Drug Discovery", Biodrugs, 2005, vol. 19, No. 6, pp. 383-392.
Yan et al., "Construction of a synthetic phage-displayed Nanobody library with CDR3 regions randomized by trinucleotide cassettes for diagnostic applications", Journal of Translational Medicine, 2014, 12:343, 12 pages.
Zarebski et al., "Llama Single Domain Antibodies as a Tool for Molecular Mimicry", Journal of Molecular Biology, 2005, vol. 349, pp. 814-824.
Zhu et al., "Generation and characterization of non-competitive furin-inhibiting nanobodies", Biochem J, Nov. 15, 2012, vol. 448, No. 1, pp. 73-82.

\* cited by examiner

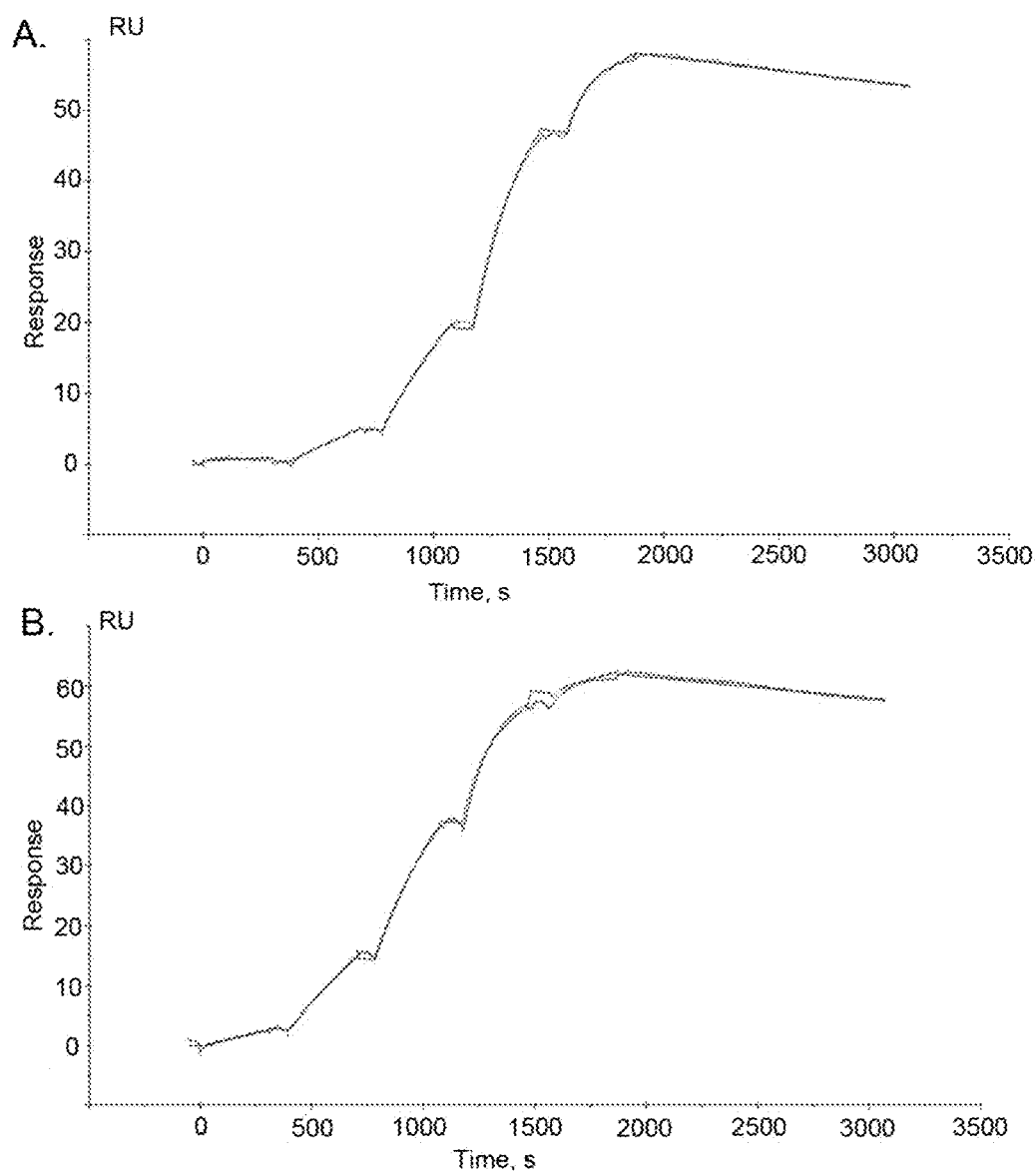
Fig. 4A-B

```
                FR1                       CDR1                    FR2
        ....|....|....|....|....|....|....|....|....|....|....|....|
                 10        20        30        40        50
113     -MQVQLVESGGGLVPAGGSLRLSCTTSERAFRSNAMGWFRQAPGKEREFVA
219     MAEVQLVESGGGLVQPGGSLRLSCTTSTSLFSITIMGWYRQAPGKQRELVA

CDR2                      FR3
        ....|....|....|....|....|....|....|....|....|....|....|....|
                 60        70        80        90        100
113     AVSVLSWSGDSAVYADSVAGRFTIFRDNAKNTVYLQMNSLKPEDTAVYYCN
219     SIK---RGGGINYADSMKGRFTISRDNARNTVFLEMNLTTEDTAVYYCN

CDR3               FR4 and TAG
        ....|....|....|....|....|....|....|....|....|....|....|....|
                 110       120       130       140       150
113     GASDIGALQSGASSWSWGHGTQVTVSSGQAGQHHHHHGAYPYDVPDYAS
219     ---AAILAYTGEVTINY-WGQGTQVTVSSGQAGQHHHHHGAYPYDVPDYAS
```

*Fig. 5*

SEQUENCE LISTING

```
<160> NUMBER OF SEQ ID NOS: 98

<210> SEQ ID NO 1
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Glu Val Gln Leu Val Glu Ser Gly Gly Gly Leu Val Gln Ala
1               5                   10                  15

Gly Gly Ser Leu Arg Leu Thr Cys Ala Ala Ser Ala Gly Ser Phe Arg
            20                  25                  30

Gly Tyr Ala Met Gly Trp Phe Arg Gln Ala Pro Gly Lys Glu Arg Glu
        35                  40                  45

Phe Val Ala Ala Val Ser Val Leu Thr Trp Ser Gly Asp Ser Thr Asn
    50                  55                  60

Ile Ala Asp Ser Val Lys Gly Arg Phe Thr Ile Phe Arg Asp Thr Ala
65                  70                  75                  80

Lys Asn Thr Val Tyr Leu Gln Met Asn Ser Leu Lys Pro Glu Asp Thr
                85                  90                  95

Ala Val Tyr Tyr Cys Asn Gly Ala Ser Glu Ile Gly Ala Leu Gln Ser
            100                 105                 110

Gly Ala Ser Leu Trp Ser Trp Gly Gln Gly Thr Gln Val Thr Val Ser
        115                 120                 125

Ser Gly Gln Ala Gly Gln His His His His His Gly Ala Tyr Pro
    130                 135                 140

Tyr Asp Val Pro Asp Tyr Ala Ser
145                 150

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Ala Ala Ser Ala Gly Ser Phe Arg Gly Tyr Ala Met
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 3

Ala Val Ser Val Leu Thr Trp Ser Gly Asp Ser Thr Asn
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ala Ser Glu Ile Gly Ala Leu Gln Ser Gly Ala Ser Leu Trp
1               5                   10                  15

<210> SEQ ID NO 5
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Glu Val Gln Leu Met Glu Ser Ala Gly Gly Leu Val Arg Pro
1               5                   10                  15

Gly Gly Ser Leu Arg Leu Ser Cys Val Ala Ser Gly Ser Ile Gly Asp
                20                  25                  30

Ile Tyr Ser Met Gly Trp Tyr Arg Gln Ala Pro Gly Lys Gln Arg Glu
            35                  40                  45

Leu Val Ala Thr Val Gly Ala Gly Gly Leu Thr Asp Tyr Gly Asp Ser
        50                  55                  60

Val Leu Gly Arg Phe Thr Ile Ser Arg Asp Lys Thr Lys Gly Thr Val
65                  70                  75                  80

Ser Leu Glu Met Asn Ser Leu Lys Pro Glu Asp Thr Ala Val Tyr Tyr
                85                  90                  95

Cys Asn Ala Asp Val Ser Ile Gly Pro Thr Gly Leu Arg Val Tyr Trp
            100                 105                 110

Gly Gln Gly Thr Gln Val Thr Val Ser Ser Gly Gln Ala Gly Gln His
        115                 120                 125

His His His His His Gly Ala Tyr Pro Tyr Asp Val Pro Asp Tyr Ala
    130                 135                 140

Ser
145

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Val Ala Ser Gly Ser Ile Gly Asp Ile Tyr Ser Met
1               5                   10

<210> SEQ ID NO 7
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 7

Thr Val Gly Ala Gly Gly Leu Thr Asp
1               5

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Asp Val Ser Ile Gly Pro Thr Gly Leu Arg Val
1               5                   10

<210> SEQ ID NO 9
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Glu Val Gln Leu Val Glu Ser Gly Gly Gly Leu Val Gln Pro
1               5                   10                  15

Gly Gly Ser Leu Arg Leu Ser Cys Glu Ala Thr Gly Asn Phe Asp Asp
                20                  25                  30

Arg Gly Ile Gly Trp Phe Arg Gln Ala Pro Gly Lys Glu Arg Glu Gly
            35                  40                  45

Ile Ala Cys Ile Thr Thr Arg Gly Arg Thr His Tyr Ala Glu Ser Val
        50                  55                  60

Glu Gly Arg Phe Thr Ile Ser Thr Asp Ile Ala Asn Asn Ala Val Tyr
65                  70                  75                  80

Leu Gln Met Asn Ser Leu Lys Pro Glu Asp Thr Ala Val Tyr Tyr Cys
                85                  90                  95

Ala Lys Ala Ile Arg Leu Thr Thr Asp Arg Thr Gln Cys Val Ala Phe
            100                 105                 110

Pro Gly Val Ser Trp Gly Arg Gly Thr Gln Val Thr Val Ser Ser Gly
        115                 120                 125

Gln Ala Gly Gln His His His His His Gly Ala Tyr Pro Tyr Asp
    130                 135                 140

Val Pro Asp Tyr Ala Ser
145                 150

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Glu Ala Thr Gly Asn Phe Asp Asp Arg Gly Ile
1               5                   10
```

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Ile Thr Thr Arg Gly Arg Thr His
1               5

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Ala Ile Arg Leu Thr Thr Asp Arg Thr Gln Cys Val Ala Phe Pro
1               5                   10                  15

Gly Val

<210> SEQ ID NO 13
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gln Val Gln Leu Val Glu Ser Gly Gly Gly Leu Val Pro Ala Gly
1               5                   10                  15

Gly Ser Leu Arg Leu Ser Cys Thr Thr Ser Glu Arg Ala Phe Arg Ser
                20                  25                  30

Asn Ala Met Gly Trp Phe Arg Gln Ala Pro Gly Lys Glu Arg Glu Phe
            35                  40                  45

Val Ala Val Ser Val Leu Ser Trp Ser Gly Asp Ser Ala Val Val
        50                  55                  60

Ala Asp Ser Val Ala Gly Arg Phe Thr Ile Phe Arg Asp Asn Ala Lys
65                  70                  75                  80

Asn Thr Val Tyr Leu Gln Met Asn Ser Leu Lys Pro Glu Asp Thr Ala
                85                  90                  95

Val Tyr Tyr Cys Asn Gly Ala Ser Asp Ile Gly Ala Leu Gln Ser Gly
            100                 105                 110

Ala Ser Ser Trp Ser Trp Gly His Gly Thr Gln Val Thr Val Ser Ser
        115                 120                 125

Gly Gln Ala Gly Gln His His His His His Gly Ala Tyr Pro Tyr
    130                 135                 140

Asp Val Pro Asp Tyr Ala Ser
145                 150

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 14

Cys Thr Thr Ser Glu Arg Ala Phe Arg Ser Asn Ala Met
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Val Ser Val Leu Ser Trp Ser Gly Asp Ser Ala Val
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ala Ser Asp Ile Gly Ala Leu Gln Ser Gly Ala Ser Ser Trp
1               5                   10                  15

<210> SEQ ID NO 17
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Gln Val Lys Leu Gln Glu Ser Gly Gly Gly Leu Val Gln Pro
1               5                   10                  15

Gly Glu Ser Leu Thr Leu Ser Cys Ala Val Ser Val Arg Leu Ser Gly
            20                  25                  30

Ile Thr Thr Met Gly Trp Tyr Arg Gln Ala Pro Gly Lys Gln Arg Glu
        35                  40                  45

Met Val Ala Ser Ile Ser Arg Gly Gly Ser Thr Val Tyr Leu Asp Ser
    50                  55                  60

Val Lys Gly Arg Phe Thr Val Ser Arg Asp Asn Thr Lys Asn Thr Val
65                  70                  75                  80

Lys Leu Gln Met Asn Ser Leu Lys Pro Glu Asp Thr Ala Ile Tyr Tyr
                85                  90                  95

Cys Asn Ala Lys Ile Leu Leu Val Ala Ser Thr Asp Asp Tyr Trp Gly
            100                 105                 110

Gln Gly Thr Gln Val Thr Val Ser Ser Gly Ala Gly Gln His His
        115                 120                 125

His His His His Gly Ala Tyr Pro Tyr Asp Val Pro Asp Tyr Ala Ser
    130                 135                 140

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 18

Cys Ala Val Ser Val Arg Leu Ser Gly Ile Thr Thr Met
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ile Ser Arg Gly Gly Ser Thr Val
1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Lys Ile Leu Leu Val Ala Ser Thr Asp Asp
1               5                   10

<210> SEQ ID NO 21
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ala Glu Val Gln Leu Val Glu Ser Gly Gly Gly Leu Val Gln Pro
1               5                   10                  15

Gly Gly Ser Leu Arg Leu Ser Cys Thr Ala Ser Gly Ser Ile Leu Lys
            20                  25                  30

Ile Tyr Thr Met Asp Trp Tyr Arg Gln Ala Pro Gly Lys Gln Arg Asp
        35                  40                  45

Leu Val Ala Thr Val Ser Ser Arg Gly Asp Thr Asp Tyr Thr Asp Ser
    50                  55                  60

Val Lys Gly Arg Phe Thr Ile Ser Arg Asp Asp Ala Lys Asn Thr Ala
65                  70                  75                  80

Tyr Leu Gln Met Ser Ser Leu Lys Pro Glu Asp Thr Ala Val Tyr Tyr
                85                  90                  95

Cys Asn Phe Tyr Ile Gln Ser Arg Thr Ala Pro Phe Asn Asp Tyr Trp
            100                 105                 110

Gly Gln Gly Thr Gln Val Thr Val Ser Ser Gly Gln Ala Gly Gln His
        115                 120                 125

His His His His His Gly Ala Tyr Pro Tyr Asp Val Pro Asp Tyr Ala
    130                 135                 140

Ser
145

<210> SEQ ID NO 22
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Thr Ala Ser Gly Ser Ile Leu Lys Ile Tyr Thr Met
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Val Ser Ser Arg Gly Asp Thr Asp
1               5

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Tyr Ile Gln Ser Arg Thr Ala Pro Phe Asn Asp
1               5                   10

<210> SEQ ID NO 25
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Ala Asp Val Gln Leu Gln Ala Ser Gly Gly Leu Val Gln Pro
1               5                   10                  15

Gly Gly Ser Leu Arg Leu Ser Cys Ala Ala Thr Gly Ser Thr Asp Arg
                20                  25                  30

Ile Ala Phe Met Gly Trp Tyr Arg Gln Ala Pro Gly Lys Leu Arg Glu
            35                  40                  45

Leu Val Ala Gly Ile Thr Ser Asp Gly Arg Thr Asn Tyr Ala Asp Asp
    50                  55                  60

Val Asp Val Ser Gly Arg Phe Thr Ile Ser Arg Asp Ser Ala Lys Asn
65                  70                  75                  80

Met Val Tyr Leu Gln Met Asn Ser Leu Lys Pro Glu Asp Thr Ala Val
                85                  90                  95

Tyr Tyr Cys Asn Ala Asp Ile Thr Leu Ala Met Gly Gly Leu Arg Val
            100                 105                 110

Tyr Trp Gly Gln Gly Thr Gln Val Thr Val Ser Ser Gly Gln Ala Gly
        115                 120                 125

Gln His His His His His Gly Ala Tyr Pro Tyr Asp Val Pro Asp
    130                 135                 140

Tyr Ala Ser
145
```

```
<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Ala Ala Thr Gly Ser Thr Asp Arg Ile Ala Phe Met
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Ile Thr Ser Asp Gly Arg Thr Asn
1               5

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Asp Ile Thr Leu Ala Met Gly Gly Leu Arg Val
1               5                   10

<210> SEQ ID NO 29
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Ala Gln Val Gln Leu Gln Gln Ser Gly Gly Leu Val Gln Pro
1               5                   10                  15

Gly Gly Ser Leu Arg Leu Ser Cys Thr Thr Ser Thr Ser Leu Phe Ser
            20                  25                  30

Ile Thr Thr Met Gly Trp Tyr Arg Gln Ala Pro Gly Lys Gln Arg Glu
        35                  40                  45

Leu Val Ala Gly Ile Lys Arg Gly Gly Ala Thr Asn Tyr Ala Asp Ser
    50                  55                  60

Val Lys Gly Arg Phe Thr Ile Ser Arg Asp Asn Ala Arg Asn Thr Val
65                  70                  75                  80

Phe Leu Gln Met Asn Ser Leu Thr Thr Glu Asp Thr Ala Val Tyr Tyr
                85                  90                  95

Cys Asn Ala Gln Ile Leu Ala Tyr Thr Gly Gly Glu Thr Asn Tyr Trp
                100                 105                 110

Gly Gln Gly Thr Gln Val Thr Val Ser Ser Gly Gln Ala Gly Gln His
            115                 120                 125

His His His His His Gly Ala Tyr Pro Tyr Asp Val Pro Asp Tyr Ala
```

-continued

```
                130                 135                 140
Ser
145

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Thr Thr Ser Thr Ser Leu Phe Ser Ile Thr Thr Met
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ile Lys Arg Gly Gly Ala Thr Asn
1               5

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Gln Ile Leu Ala Tyr Thr Gly Gly Glu Thr Asn
1               5                   10

<210> SEQ ID NO 33
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Ala Glu Val Gln Leu Val Glu Ser Val Gly Gly Leu Val Gln Pro
1               5                   10                  15

Gly Gly Ser Leu Arg Leu Ser Cys Val Ala Ser Gly Asn Ile Gly Asp
            20                  25                  30

Ile Tyr Thr Met Gly Trp Tyr Arg Gln Ala Pro Gly Lys Gln Arg Glu
        35                  40                  45

Leu Val Ala Thr Val Gly Asp Gly Gly Leu Thr Asn Phe Val Asp Ser
    50                  55                  60

Val Lys Gly Arg Phe Thr Ile Ser Arg Asp Lys Ser Lys Gly Thr Val
65                  70                  75                  80

Ser Leu Glu Met Asn Ser Leu Lys Pro Glu Asp Thr Ala Val Tyr Tyr
                85                  90                  95

Cys Asn Ala Asp Val Arg Ile Gly Pro Thr Gly Leu Arg Val Tyr Trp
            100                 105                 110
```

```
Gly Gln Gly Thr Gln Val Thr Val Ser Ser Gly Gln Ala Gly Gln His
            115                 120                 125

His His His His His Gly Ala Tyr Pro Tyr Asp Val Pro Asp Tyr Ala
    130                 135                 140

Ser
145

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Val Ala Ser Gly Asn Ile Gly Asp Ile Tyr Thr Met
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Val Gly Asp Gly Gly Leu Thr Asn
1               5

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Asp Val Arg Ile Gly Pro Thr Gly Leu Arg Val
1               5                   10

<210> SEQ ID NO 37
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Ala Glu Val Gln Leu Val Glu Ser Gly Gly Gly Leu Val Gln Pro
1               5                   10                  15

Gly Gly Ser Leu Thr Leu Ser Cys Ala Thr Ser Thr Ser Ile Phe Ser
            20                  25                  30

Ile Thr Ala Met Gly Trp Tyr Arg Gln Ala Pro Gly Lys Gln Arg Glu
        35                  40                  45

Leu Ile Ala Gly Ile Lys Arg Gly Gly Ser Thr Asn Tyr Ala Asp Ser
    50                  55                  60

Val Lys Gly Arg Phe Thr Ile Ser Arg Asp Asn Ala Arg Asn Thr Val
65                  70                  75                  80

Phe Leu Gln Met Asn Ser Leu Thr Thr Glu Asp Thr Ala Val Tyr Tyr
                85                  90                  95
```

Cys Asn Ala Gln Ile Leu Ser Tyr Val Gly Glu Ile Thr Asn Tyr Trp
            100                 105                 110

Gly Gln Gly Thr Gln Val Thr Val Ser Ser Gly Gln Ala Gly Gln His
        115                 120                 125

His His His His His Gly Ala Tyr Pro Tyr Asp Val Pro Asp Tyr Ala
    130                 135                 140

Ser
145

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Ala Thr Ser Thr Ser Ile Phe Ser Ile Thr Ala Met
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Gly Ile Lys Arg Gly Gly Ser Thr Asn
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Gln Ile Leu Ser Tyr Val Gly Glu Ile Thr Asn
1               5                   10

<210> SEQ ID NO 41
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Ala Glu Val Gln Leu Val Glu Ser Gly Gly Gly Leu Val Gln Pro
1               5                   10                  15

Gly Gly Ser Leu Arg Leu Ser Cys Thr Thr Ser Thr Ser Leu Phe Ser
            20                  25                  30

Ile Thr Thr Met Gly Trp Tyr Arg Gln Ala Pro Gly Lys Gln Arg Glu
        35                  40                  45

Leu Val Ala Ser Ile Lys Arg Gly Gly Gly Thr Asn Tyr Ala Asp Ser
    50                  55                  60

Met Lys Gly Arg Phe Thr Ile Ser Arg Asp Asn Ala Arg Asn Thr Val

```
                65                  70                  75                  80
Phe Leu Glu Met Asn Asn Leu Thr Thr Glu Asp Thr Ala Val Tyr Tyr
                        85                  90                  95

Cys Asn Ala Ala Ile Leu Ala Tyr Thr Gly Glu Val Thr Asn Tyr Trp
                100                 105                 110

Gly Gln Gly Thr Gln Val Thr Val Ser Ser Gly Gln Ala Gly Gln His
            115                 120                 125

His His His His His Gly Ala Tyr Pro Tyr Asp Val Pro Asp Tyr Ala
        130                 135                 140

Ser
145

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Thr Thr Ser Thr Ser Leu Phe Ser Ile Thr Thr Met
1               5                   10

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Ile Lys Arg Gly Gly Gly Thr Asn
1               5

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Ala Ile Leu Ala Tyr Thr Gly Glu Val Thr Asn
1               5                   10

<210> SEQ ID NO 45
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Ala Glu Val Gln Leu Val Glu Ser Gly Gly Gly Leu Val Gln Pro
1               5                   10                  15

Gly Gly Ser Leu Arg Leu Ser Cys Val Ala Ser Gly Asn Ile Gly Asn
            20                  25                  30

Ile Tyr Thr Met Gly Trp Tyr Arg Gln Ala Pro Gly Lys Gln Arg Glu
        35                  40                  45
```

```
Leu Val Ala Ala Val Gly Ala Gly Glu Leu Thr Asn Tyr Val Asp Ser
    50                  55                  60

Val Lys Gly Arg Phe Thr Ile Ser Arg Asp Lys Ser Lys Gly Thr Val
 65                  70                  75                  80

Ser Leu Glu Met Asn Ser Leu Lys Pro Glu Asp Thr Ala Val Tyr Tyr
                 85                  90                  95

Cys Asn Ala Asp Val Ser Ile Gly Pro Thr Gly Leu Arg Val Tyr Trp
            100                 105                 110

Gly Gln Gly Thr Gln Val Thr Val Ser Ser Gly Gln Ala Gly Gln His
            115                 120                 125

His His His His His Gly Ala Tyr Pro Tyr Asp Val Pro Asp Tyr Ala
    130                 135                 140

Ser
145

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys Val Ala Ser Gly Asn Ile Gly Asn Ile Tyr Thr Met
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Val Gly Ala Gly Glu Leu Thr Asn
1               5

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Asp Val Ser Ile Gly Pro Thr Gly Leu Arg Val
1               5                   10

<210> SEQ ID NO 49
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Ala Gln Val Lys Leu Gln Glu Ser Gly Gly Gly Leu Val Gln Pro
1               5                   10                  15

Gly Gly Ser Leu Arg Leu Ser Cys Ala Ser Ser Val Pro Ile Phe Ala
            20                  25                  30
```

Ile Thr Val Met Gly Trp Tyr Arg Gln Ala Pro Gly Lys Gln Arg Glu
            35                  40                  45

Leu Val Ala Gly Ile Lys Arg Ser Gly Asp Thr Asn Tyr Ala Asp Ser
     50                  55                  60

Val Lys Gly Arg Phe Thr Ile Ser Arg Asp Asp Ala Lys Asn Thr Val
 65                  70                  75                  80

Phe Leu Gln Met Asn Ser Leu Thr Thr Glu Asp Thr Ala Val Tyr Tyr
                 85                  90                  95

Cys Asn Ala Gln Ile Leu Ser Trp Met Gly Thr Asp Tyr Trp Gly
                100                 105                 110

Gln Gly Thr Gln Val Thr Val Ser Ser Gly Gln Ala Gly Gln His His
            115                 120                 125

His His His His Gly Ala Tyr Pro Tyr Asp Val Pro Asp Tyr Ala Ser
        130                 135                 140

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Ala Ser Ser Val Pro Ile Phe Ala Ile Thr Val Met
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Ile Lys Arg Ser Gly Asp Thr Asn
1               5

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Gln Ile Leu Ser Trp Met Gly Gly Thr Asp
1               5                   10

<210> SEQ ID NO 53
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (14)..(14)

```
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(32)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (37)..(38)
<223> OTHER INFORMATION: Any amino acid
<220> FEATURE:
<221> NAME/KEY: MOD_RES
<222> LOCATION: (52)..(52)
<223> OTHER INFORMATION: Any amino acid
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (77)..(78)
<223> OTHER INFORMATION: Any amino acid
<220> FEATURE:
<221> NAME/KEY: MOD_RES
<222> LOCATION: (81)..(82)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (88)..(88)
<223> OTHER INFORMATION: Any amino acid
<220> FEATURE:
<221> NAME/KEY: MOD_RES
<222> LOCATION: (95)..(97)
<223> OTHER INFORMATION: Any amino acid
<220> FEATURE:
<221> NAME/KEY: MOD_RES
<222> LOCATION: (107)..(108)
<223> OTHER INFORMATION: Any amino acid
<220> FEATURE:
<221> NAME/KEY: MOD_RES
<222> LOCATION: (110)..(110)
<223> OTHER INFORMATION: Any amino acid
<220> FEATURE:
<221> NAME/KEY: MOD_RES
<222> LOCATION: (118)..(118)
<223> OTHER INFORMATION: Any amino acid
<220> FEATURE:
<221> NAME/KEY: MOD_RES
<222> LOCATION: (125)..(125)
<223> OTHER INFORMATION: Any amino acid
<220> FEATURE:
<221> NAME/KEY: MOD_RES
```

```
<222> LOCATION: (141)..(141)
<223> OTHER INFORMATION: Any amino acid
<220> FEATURE:
<221> NAME/KEY: MOD_RES
<222> LOCATION: (146)..(146)
<223> OTHER INFORMATION: Any amino acid
<220> FEATURE:
<221> NAME/KEY: MOD_RES
<222> LOCATION: (148)..(148)
<223> OTHER INFORMATION: Any amino acid
<220> FEATURE:
<221> NAME/KEY: MOD_RES
<222> LOCATION: (151)..(151)
<223> OTHER INFORMATION: Any amino acid

<400> SEQUENCE: 53

Met Ala Glu Xaa Gln Leu Val Glu Ser Gly Gly Leu Xaa Glu Xaa
1               5                   10                  15

Gly Gly Ser Xaa Arg Leu Ser Xaa Gly Gly Xaa Gly Phe Thr Xaa Xaa
            20                  25                  30

Gly Xaa Gly Ile Xaa Xaa Phe Arg Gln Ala Pro Gly Lys Glu Arg Glu
        35                  40                  45

Gly Val Ser Xaa Ile Ser Asn Asp Asp Gly Arg Thr Xaa Tyr Thr Asp
    50                  55                  60

Ser Ala Lys Gly Arg Phe Thr Xaa Ser Val Asp Tyr Xaa Xaa Asn Thr
65                  70                  75                  80

Xaa Xaa Leu Gln Xaa Ser Thr Xaa Lys Pro Glu Asp Thr Ala Xaa Xaa
                85                  90                  95

Xaa Cys Ala Ala Ser Asn Tyr Met Asn Ser Xaa Xaa Val Xaa Tyr Gly
            100                 105                 110

Asn Gly Asn Glu Tyr Xaa Gly Gln Gly Thr Gln Val Xaa Val Ser Ser
        115                 120                 125

Gly Gln Ala Gly Gln His His His His His Gly Xaa Tyr Pro Tyr
    130                 135                 140

Asp Xaa Pro Xaa Tyr Ala Xaa
145                 150

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 54

Xaa Gly Gly Xaa Gly Phe Thr Xaa Xaa Gly Xaa Gly Ile
1               5                   10

<210> SEQ ID NO 55
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 55

Xaa Ile Ser Asn Asp Asp Gly Arg Thr Xaa
1               5                   10

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 56

Ala Ser Asn Tyr Met Asn Ser Xaa Xaa Val Xaa Tyr Gly Asn Gly Asn
1               5                   10                  15

Glu

<210> SEQ ID NO 57
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Ala Gln Val Lys Leu Gln Glu Ser Gly Gly Gly Leu Val Gln Pro
1               5                   10                  15

Gly Gly Ser Leu Arg Leu Ser Cys Val Ala Ser Gly Asn Ile Gly Asp
            20                  25                  30

Ile Tyr Thr Met Gly Trp Tyr Arg Gln Ala Pro Gly Lys Gln Arg Glu
        35                  40                  45

Leu Val Ala Thr Val Gly Asp Gly Gly Leu Thr Asn Phe Val Asp Ser
    50                  55                  60

Val Lys Gly Arg Phe Thr Ile Ser Arg Asp Lys Ser Lys Gly Thr Val
65                  70                  75                  80

Ser Leu Glu Met Asn Ser Leu Lys Pro Glu Asp Thr Ala Val Tyr Tyr
                85                  90                  95

Cys Asn Ala Asp Val Arg Ile Gly Pro Thr Gly Leu Arg Val Tyr Trp
            100                 105                 110

Gly Gln Gly Thr Gln Val Thr Val Ser Ser Gly Gln Ala Gly Gln His
        115                 120                 125
```

```
His His His His His Gly Ala Tyr Pro Tyr Asp Val Pro Asp Tyr Ala
            130                 135                 140

Ser
145

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Cys Val Ala Ser Gly Asn Ile Gly Asp Ile Tyr Thr Met
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Val Gly Asp Gly Gly Leu Thr Asn
1               5

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Asp Val Arg Ile Gly Pro Thr Gly Leu Arg Val
1               5                   10

<210> SEQ ID NO 61
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Ala Gln Val Gln Leu Gln Glu Ser Gly Gly Gly Leu Val Gln Pro
1               5                   10                  15

Gly Glu Ser Met Thr Leu Ser Cys Ala Val Ser Val Arg Leu Ser Ser
            20                  25                  30

Ile Thr Thr Met Gly Trp Tyr Arg Gln Ala Pro Gly Lys Gln Arg Glu
        35                  40                  45

Met Val Ala Ser Ile Arg Arg Gly Gly Ser Thr Ala Tyr Leu Asp Ser
    50                  55                  60

Leu Lys Asp Arg Phe Thr Ile Ser Arg Asp Asn Thr Lys Asn Thr Val
65                  70                  75                  80

Asn Leu Gln Met Asn Ser Leu Lys Pro Glu Asp Thr Ala Ile Tyr Tyr
                85                  90                  95

Cys Asn Ala Lys Ile Leu Leu Val Ala Ser Ser Glu Asp Tyr Trp Gly
            100                 105                 110
```

Gln Gly Thr Gln Val Thr Val Ser Ser Gly Gln Ala Gly Gln His His
            115                 120                 125

His His His His Gly Ala Tyr Pro Tyr Asp Val Pro Asp Tyr Ala Ser
    130                 135                 140

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Ala Val Ser Val Arg Leu Ser Ser Ile Thr Thr Met
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Ile Arg Arg Gly Gly Ser Thr Ala
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Lys Ile Leu Leu Val Ala Ser Ser Glu Asp
1               5                   10

<210> SEQ ID NO 65
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Ala Gln Val Gln Leu Val Gln Ser Gly Gly Gly Leu Val Gln Pro
1               5                   10                  15

Gly Gly Ser Leu Arg Leu Ser Cys Thr Thr Ser Thr Ser Leu Phe Ser
            20                  25                  30

Ile Thr Thr Met Gly Trp Tyr Arg Gln Ala Pro Gly Lys Gln Arg Glu
        35                  40                  45

Leu Val Ala Gly Ile Lys Arg Gly Gly Ala Thr Asn Tyr Ala Asp Ser
    50                  55                  60

Val Lys Gly Arg Phe Thr Ile Ser Arg Asp Asn Ala Arg Asn Thr Val
65                  70                  75                  80

Phe Leu Gln Met Asn Ser Leu Thr Thr Glu Asp Thr Ala Val Tyr Tyr
                85                  90                  95

Cys Asn Ala Gln Ile Leu Ala Tyr Thr Gly Gly Glu Thr Asn Tyr Trp

```
                       100                 105                 110
Gly Gln Gly Thr Gln Val Thr Val Ser Ser Gly Gln Ala Gly Gln His
            115                 120                 125

His His His His His Gly Ala Tyr Pro Tyr Asp Val Pro Asp Tyr Ala
    130                 135                 140

Ser
145

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Thr Thr Ser Thr Ser Leu Phe Ser Ile Thr Thr Met
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ile Lys Arg Gly Gly Ala Thr Asn
1               5

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Gln Ile Leu Ala Tyr Thr Gly Gly Glu Thr Asn
1               5                   10

<210> SEQ ID NO 69
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Ala Asp Val Gln Leu Gln Ala Ser Gly Gly Gly Leu Val Gln Pro
1               5                   10                  15

Gly Gly Ser Leu Arg Leu Ser Cys Ala Thr Ser Thr Ser Val Phe Ser
            20                  25                  30

Ile Thr Thr Leu Gly Trp Tyr Arg Gln Ala Pro Gly Lys Gln Arg Glu
        35                  40                  45

Leu Val Ala Ser Met Lys Arg Gly Gly Asp Thr Asn Tyr Ala Asp Ser
    50                  55                  60

Val Lys Gly Arg Phe Thr Ile Ser Arg Asp Asn Ala Arg Asn Thr Val
65                  70                  75                  80
```

```
Phe Leu Gln Met Asn Asn Leu Thr Thr Glu Asp Thr Ala Val Tyr Tyr
                85                  90                  95

Cys Asn Ala Ala Ile Leu Ala Tyr Thr Gly Ala Val Thr Asn Tyr Trp
            100                 105                 110

Gly Gln Gly Thr Gln Val Thr Val Ser Ser Gly Gln Ala Gly Gln His
        115                 120                 125

His His His His His Gly Ala Tyr Pro Tyr Asp Val Pro Asp Tyr Ala
    130                 135                 140

Ser
145

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Ala Thr Ser Thr Ser Val Phe Ser Ile Thr Thr Leu
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Met Lys Arg Gly Gly Asp Thr Asn
1               5

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Ala Ile Leu Ala Tyr Thr Gly Ala Val Thr Asn
1               5                   10

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Leu Asn Asp Ile Phe Glu Ala Gln Lys Ile Glu Trp His Glu
1               5                   10                  15

<210> SEQ ID NO 74
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 74

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Glu Glu Glu Glu Glu
1               5

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ala Pro Val Pro Tyr Pro Asp Pro Leu Glu Pro Arg
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Tyr Lys Asp Asp Asp Asp Lys
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Pro Tyr Asp Val Pro Asp Tyr Ala
1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 79
```

His His His His His His His His His His
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Gln Lys Leu Ile Ser Glu Glu Asp Leu
1               5                   10

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Lys Glu Asn Pro Arg Ser Asn Gln Glu Glu Ser Tyr Asp Asp Asn
1               5                   10                  15

Glu Ser

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Lys Glu Thr Ala Ala Ala Lys Phe Glu Arg Gln His Met Asp Ser
1               5                   10                  15

<210> SEQ ID NO 83
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Ser Leu Ala Glu Leu Leu Asn Ala Gly Leu Gly Gly Ser
1               5                   10
```

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

```
Thr Gln Asp Pro Ser Arg Val Gly
1               5
```

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

```
Trp Ser His Pro Gln Phe Glu Lys
1               5
```

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

```
Gly Lys Pro Ile Pro Asn Pro Leu Leu Gly Leu Asp Ser Thr
1               5                   10
```

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

```
Tyr Thr Asp Ile Glu Met Asn Arg Leu Gly Lys
1               5                   10
```

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Asp Leu Tyr Asp Asp Asp Asp Lys
1               5
```

<210> SEQ ID NO 90
<211> LENGTH: 6
<212> TYPE: PRT
<213> ORGANISM: Artificial Sequence
<220> FEATURE:

```
<223> OTHER INFORMATION: Description of Artificial Sequence: Synthetic
      6xHis tag

<400> SEQUENCE: 90

His His His His His His
1               5

<210> SEQ ID NO 91
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gttattactc gcggcccagg cggccatggc ccaggtsmar ctgcagsagt cwgg         54

<210> SEQ ID NO 92
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tgttattatc tgcggcccag gcggccatgg ccgatgtgca gctgcaggcg tctggrggag   60
g                                                                  61

<210> SEQ ID NO 93
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
catgccatga ctcgcggccc aggcggccat ggcccaggtg cagctggtgc agtctgg      57

<210> SEQ ID NO 94
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
catgccatga ctcgcggccc aggcggccat ggccgaggtg cagctggtgg agtctgg      57

<210> SEQ ID NO 95
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
catgccatga ctcgcggccc aggcggccat ggcccaggtg cagctgcagg agtcggg      57

<210> SEQ ID NO 96
<211> LENGTH: 60
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (49)..(49)
<223> OTHER INFORMATION: a, c, t, g, unknown or other

<400> SEQUENCE: 96
catgactgtg gcccaggcgg ccatgcaggt gcagctcgtg gaswchggng gaggmttggt        60

<210> SEQ ID NO 97
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
catgccatga ctgtggccca ggcggcccag ktgcagctcg tggagtc                      47

<210> SEQ ID NO 98
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ccacgattct ggccggcctg gcctgaggag acrgtgacct gggtcc                       46
```

NANOBODIES AGAINST CYSTIC FIBROSIS TRANSMEMBRANE CONDUCTANCE REGULATOR (CFTR) INHIBITORY FACTOR (CIF)

CROSS-REFERENCE TO RELATED APPLICATIONS

This application is the U.S. National Stage Entry under § 371 of International Application No. PCT/US2018/034878, filed May 29, 2018, which claims priority benefit of U.S. Provisional Application No. 62/512,711, filed on May 30, 2017, each of which is hereby incorporated herein by reference in its entirety for all purposes.

STATEMENT OF GOVERNMENTAL SUPPORT

This invention was made with government support under Grant Nos P42ES004699, R01ES002710 and AI091699, awarded by the National Institutes of Health. The government has certain rights in the invention.

SEQUENCE LISTING

This application contains a Sequence Listing in computer readable form (filename: 050759-515N01US_SL.TXT; 47,930 bytes—ASCII text file; created Nov. 25, 2019), which is incorporated hereby reference in its entirety and forms part of the disclosure.

BACKGROUND

Drug screening is a complex laborious yet critical step in drug identification. With biologics quickly developing and gaining a big part of the drug market, the small molecule drugs remain a major tool for health managing. To screen effectively small synthetic molecules for their potency on desired biomolecular targets, a number of approaches have been developed. The assays, including scintillation proximity assay (1,2), fluorescence resonance energy transfer (FRET) (3) and fluorescence polarization (4) are successfully used for high throughput screening for drug candidates in academia and in industry. In majority, the screening schemes use the high catalytic activity of the target proteins, as for example protein kinases (5). A fast turnover of these enzymes ensures rapid signal development in the assay and therefore its high sensitivity. Consequently, these techniques can be performed in homogeneous mix-and-measure format that allow the addition of all reaction and detection components in one step without need for separation and wash steps. In contrast, the enzymes with low activity, for example family of p450 enzymes, cannot provide sufficient sensitivity in the corresponding assays. Only highly sensitive analytical detection methods can be employed in the screening process of the slow enzymes. The most employed approach relies on a method of fluorescence generation from an appropriate reporter as a result of enzymatic reaction (6). Since the fluorescent signal is accumulating over the time it gives improved sensitivity compared to other screening formats. However, for drug screening purposes higher sensitivities are often required. Therefore, screening assays coupled with LC-MS/MS detection have been established when large number of compounds needs to be analyzed (7). In turn, affinity measuring methods, like Surface Plasmon Resonance (SPR) or Bio-layer interferometry (Octet), are employed for the target validation. Despite the fact, that these methods indeed provide high sensitivity in the assays with the slow enzymes, they suffer from being laborious, time-consuming and involving expensive instrumentation.

Along with enzymatic activity of the target enzyme, the antibodies are important component of screening assays. A wide variety of conventional and recombinant antibodies are available for these purposes. However, for the past 20 years, the novel variable fragments of heavy chain only antibodies, named VHHs or Nanobodies®, have been extensively studied (8). Due to their small size, unique physical and chemical properties they have found use in a variety of research fields. They were successfully employed in different immunoassay formats (10), including biosensors (9), for the detection of small molecules as well as large proteins (10,11). Nanobodies are often used in molecular and structural biology, for example as chaperons to facilitate protein crystallization. A number of studies focus on studying, evaluation and characterization of nanobodies as biologics to treat a variety of diseases (12,13). Indeed, nanobodies offer advantageous possibilities for drug development: they are easily amenable for genetic and chemical engineering; they possess high selectivity toward their target and thus have low offsite activity compared to small molecule drugs; high solubility of VHHs is another strong advantage compared to small molecule drugs or conventional antibodies etc. (10). In addition to these characteristics, the nanobodies also possess a unique long CDR3 region that forms a long loop often thought to be responsible for analyte recognition (14,15). A small size of VHHs combined with highly selective CDR3 is a unique property allowing development of nanobodies to the cavities, cleft and catalytic sited on the proteins in general, and enzymes, receptors and membrane proteins in particular (14). Such nanobodies have been shown to be effective in selective detection of infection with trypanosomes (16). They also have potential application in tumor imaging and cancer therapy (12,13,17). The nanobodies that selectively bind to the active site of the enzyme and inhibit its catalytic activity are very valuable as drug themselves. However, they can also be used as reagents in screening assay. Nanobodies are unique reagents, and their potential is not yet fully explored. Here we report a novel assay format involving nanobodies, that can be used as a tool for screening of small molecule inhibitors applied to slow enzymes and non-catalytic proteins.

As a model system, we used cystic fibrosis transmembrane conductance regulator (CFTR) inhibitory factor (Cif) (18) This factor is found in numerous lung pathogen bacteria 19 and particularly characteristic to *P. aeruginosa* (20). It is an epoxide hydrolase, which through its activity affects the host defenses (21), resulting in an environment that permits the bacterium to form biofilms and to establish a chronic infection of the lung. It was recently identified, that Cif is required for *P. aeruginosa* to infect effectively human tissues (22). Some work has been done toward synthesis of small molecule inhibitors targeting Cif (23). However, current methods available for monitoring inhibitors' potency are limited in sensitivity (23).

SUMMARY

In one aspect, provided are recombinant, synthetic and/or non-natural VHH molecules that specifically bind to cystic fibrosis transmembrane conductance regulator (CFTR) inhibitory factor (Cif). In some embodiments, the Cif is produced by a *Pseudomonas* bacterium. In some embodiments, the Cif is produced by a *Pseudomonas aeruginosa* bacterium. In some embodiments, the VHH binds to Cif with a KD of 0.2 nM or less, e.g., 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, or less. In some embodiments, the VHH reduces or inhibits the enzymatic activity of Cif. In some embodiments, the VHH inhibits the enzymatic activity of Cif with and IC50 concentration of 3.0 µM or less, e.g., 2.9 µM, 2.8 µM, 2.7 µM, 2.6 µM, 2.5 µM, 2.4 µM, 2.3 µM, 2.2 µM, 2.1 µM, 2.0 µM, 1.9 µM, 1.8 µM, 1.7 µM, 1.6 µM, 1.5 µM, 1.4 µM, 1.3 µM, 1.2 µM, 1.1 µM, 1.0 µM, 0.9 µM, 0.8 µM, 0.7 µM, 0.6 µM, 0.5 µM, or less. In some embodiments, the VHH inhibits the enzymatic activity of Cif with and IC90 concentration of 4.0 µM or less, e.g., 3.9 µM, 3.8 µM, 3.7 µM, 3.6 µM, 3.5 µM, 3.4 µM, 3.3 µM, 3.2 µM, 3.1 µM, 3.0 µM, 2.9 µM, 2.8 µM, 2.7 µM, 2.6 µM, 2.5 µM, or less. In some embodiments, the VHH comprises:

a) a CDR1 comprising SEQ ID NO:2, a CDR2 comprising SEQ ID NO:3 and a CDR3 comprising SEQ ID NO:4;
b) a CDR1 comprising SEQ ID NO:6, a CDR2 comprising SEQ ID NO:7 and a CDR3 comprising SEQ ID NO:8;
c) a CDR1 comprising SEQ ID NO:10, a CDR2 comprising SEQ ID NO:11 and a CDR3 comprising SEQ ID NO:12;
d) a CDR1 comprising SEQ ID NO:14, a CDR2 comprising SEQ ID NO:15 and a CDR3 comprising SEQ ID NO:16;
e) a CDR1 comprising SEQ ID NO:18, a CDR2 comprising SEQ ID NO:19 and a CDR3 comprising SEQ ID NO:20;
f) a CDR1 comprising SEQ ID NO:22, a CDR2 comprising SEQ ID NO:23 and a CDR3 comprising SEQ ID NO:24;
g) a CDR1 comprising SEQ ID NO:26, a CDR2 comprising SEQ ID NO:27 and a CDR3 comprising SEQ ID NO:28;
h) a CDR1 comprising SEQ ID NO:30, a CDR2 comprising SEQ ID NO:31 and a CDR3 comprising SEQ ID NO:32;
i) a CDR1 comprising SEQ ID NO:34, a CDR2 comprising SEQ ID NO:35 and a CDR3 comprising SEQ ID NO:36;
j) a CDR1 comprising SEQ ID NO:38, a CDR2 comprising SEQ ID NO:39 and a CDR3 comprising SEQ ID NO:40;
k) a CDR1 comprising SEQ ID NO:42, a CDR2 comprising SEQ ID NO:43 and a CDR3 comprising SEQ ID NO:44;
l) a CDR1 comprising SEQ ID NO:46, a CDR2 comprising SEQ ID NO:47 and a CDR3 comprising SEQ ID NO:48;
m) a CDR1 comprising SEQ ID NO:50, a CDR2 comprising SEQ ID NO:51 and a CDR3 comprising SEQ ID NO:52;
n) a CDR1 comprising SEQ ID NO:54, a CDR2 comprising SEQ ID NO:55 and a CDR3 comprising SEQ ID NO:56;
o) a CDR1 comprising SEQ ID NO:58, a CDR2 comprising SEQ ID NO:59 and a CDR3 comprising SEQ ID NO:60;
p) a CDR1 comprising SEQ ID NO:62, a CDR2 comprising SEQ ID NO:63 and a CDR3 comprising SEQ ID NO:64;
q) a CDR1 comprising SEQ ID NO:66, a CDR2 comprising SEQ ID NO:67 and a CDR3 comprising SEQ ID NO:68; or
r) a CDR1 comprising SEQ ID NO:70, a CDR2 comprising SEQ ID NO:71 and a CDR3 comprising SEQ ID NO:72.

In some embodiments, the VHH comprises an amino acid sequence having at least 80% sequence identity, e.g., at least 85%, 90%, 91%, 92%, 93%, 94%, 95%, 96%, 97%, 98%, 99% or 100% sequence identity, to an amino acid selected from the group consisting of:
a) amino acid residues 1-134 of SEQ ID NO:1;
b) amino acid residues 1-127 of SEQ ID NO:5;
c) amino acid residues 1-132 of SEQ ID NO:9;
d) amino acid residues 1-133 of SEQ ID NO:13;
e) amino acid residues 1-126 of SEQ ID NO:17;
f) amino acid residues 1-127 of SEQ ID NO:21;
g) amino acid residues 1-129 of SEQ ID NO:25;
h) amino acid residues 1-127 of SEQ ID NO:29;
i) amino acid residues 1-127 of SEQ ID NO:33;
j) amino acid residues 1-127 of SEQ ID NO:37;
k) amino acid residues 1-127 of SEQ ID NO:41;
l) amino acid residues 1-127 of SEQ ID NO:45;
m) amino acid residues 1-126 of SEQ ID NO:49;
n) amino acid residues 1-133 of SEQ ID NO:53;
o) amino acid residues 1-127 of SEQ ID NO:57;
p) amino acid residues 1-126 of SEQ ID NO:61;
q) amino acid residues 1-127 of SEQ ID NO:65; and
r) amino acid residues 1-127 of SEQ ID NO:69.

In a further aspect, provided is a polynucleotide encoding an anti-Cif VHH molecule as described above and herein. Also contemplated are expression cassettes and vectors comprising one or more polynucleotides encoding one or more anti-Cif VHH molecules, as described above and herein.

In another aspect, provided is a fusion protein comprising an anti-Cif VHH molecule as described above and herein. In some embodiments, the fusion protein comprises one or more detectable tags, e.g., a protein tag or a peptide tag, e.g., hemagglutinin (HA) tag, FLAG tag, c-myc, poly histidine tag. In some embodiments, the fusion protein further comprises a VHH molecule that specifically binds to a complement receptor (e.g., a bispecific VHH fusion that can concurrently binds to Cif and a complement receptor). In some embodiments, the fusion protein further comprises a VHH molecule that specifically binds to the complement receptor CD11b/CD18 (Mac-1) (e.g., a bispecific or dimeric VHH fusion that can concurrently binds to Cif and Mac-1). Also contemplated are polynucleotides encoding the fusion proteins.

In another aspect, provided is a conjugate comprising an anti-Cif VHH molecule, as described above and herein, and a small organic compound that is an inhibitor of Cif enzymatic activity (e.g., Cif inhibitor compounds 1a, 1k, 8c, 8d, 8f, 8h, 8j, 18f and 18NH2 as provided in Table 7). In a related aspect, provided is a conjugate comprising an anti-Cif VHH molecule, as described above and herein, and a detectable label. In some embodiments, the detectable label is a fluorophore, a chemiluminescent moiety, an enzyme or a radio-isotope.

In a further aspect, provided is a nanoparticle or liposome comprising an anti-Cif VHH molecule, a fusion protein and/or a conjugate, as described above and herein.

In another aspect, further provided are kits. In some embodiments, the kits comprise a VHH molecule, a fusion protein, a conjugate and/or a nanoparticle or liposome, as described above and herein.

In another aspect, further provided are host cells comprising one or more polynucleotides encoding the VHH molecules and/or the fusion proteins, as described above and herein. In another aspect, further provided are methods of making a VHH molecule or a fusion protein as described above and herein. In some embodiments, the methods comprise recombinantly expressing in a host cell one or more polynucleotides encoding the VHH molecules and/or the fusion proteins, as described above and herein.

In another aspect, provided are methods of identifying a Pseudomonas infection in a subject in need thereof. In some embodiments, the methods comprise:
a) identifying a subject exhibiting symptoms consistent with a Pseudomonas infection;
b) contacting a biological sample suspected of comprising Cif molecules and obtained from the subject with an anti-Cif VHH molecule, as described above and herein, or a conjugate comprising such an anti-Cif VHH molecule, under conditions that allow the VHH molecule to bind to the Cif molecules potentially in the sample;
c) identifying the subject as having a Pseudomonas infection upon positive detection of binding of the VHH molecule to the Cif molecules in the sample. In some embodiments, the *Pseudomonas* infection is a *Pseudomonas aeruginosa* infection. In some embodiments, the biological sample is from saliva, sputum, bronchoalveolar lavage fluid (BALF), cheek swab, mucus, blood, sweat, tears, serum, plasma, urine, skin, cerebral spinal fluid (CSF), lymph, Eustachian tube fluid, bone marrow and/or feces.

In another aspect, provided are methods of reducing, inhibiting, mitigating and/or reversing one or more symptoms associated with or caused by a *Pseudomonas* infection. In some embodiments, the methods comprise administering to the subject an effective amount of an agent selected from the group consisting of an anti-Cif VHH molecule, as described above and herein, or a fusion protein, a conjugate or a nanoparticle or liposome comprising such an anti-Cif VHH molecule, as described above and herein. In varying embodiment, the *Pseudomonas* infection is a *Pseudomonas aeruginosa* infection. In some embodiments, the agent is administered via a route selected from the group consisting of intrapulmonary, inhalational, intravenous, intramuscular, subcutaneous, intradermal, transcutaneous, topical (including to the eyes), intrathecal, intralesional, transmucosal (including through tissues around the eyes), intra-arterial, intraperitoneal, intraventricular and intracranial.

In a further aspect, provided are methods of screening for inhibitors of Cif enzymatic activity. In some embodiments, the method comprises:

a) providing a solid support coated with polyclonal antibodies raised against Cif and bound to Cif;

b) concurrently exposing the solid support to an anti-Cif VHH molecule, as described above and herein, and a candidate inhibitor of Cif;

c) identifying inhibitors of Cif that compete with or displace binding of the VHH molecule to the Cif bound to the polyclonal antibodies coated on the solid support. In some embodiments, the anti-Cif VHH molecule is attached to a detectable label, and detection of the label is used to measure displacement of the VHH molecule by the Cif inhibitor, e.g., used to measure unbound VHH molecule. In some embodiments, the anti-Cif VHH molecule further comprises one or more detectable tags (e.g., hemagglutinin (HA) tag, FLAG tag, c-myc, poly histidine tag), and an antibody against the tag is used to measure displacement of the VHH molecule by the Cif inhibitor. In some embodiments, the Cif inhibitor is a small organic compound. In some embodiments, the screening methods identifies a Cif inhibitor that inhibits Cif enzymatic or catalytic activity with a greater potency than the VHH molecule. In some embodiments, the solid support is a bead, a microwell plate, a chip or a microfluidics device.

In a further aspect, provided are methods of screening for inhibitors of enzymatic or catalytic activity of an enzyme. In some embodiments, the method comprises:

a) providing a solid support coated with polyclonal antibodies raised against the enzyme and bound to the enzyme;

b) concurrently exposing the solid support to a VHH molecule that binds to and inhibits the enzymatic or catalytic activity of the enzyme and a candidate inhibitor of the enzyme;

c) identifying inhibitors of the enzyme that compete with or displace binding of the VHH molecule to the enzyme bound to the polyclonal antibodies coated on the solid support. In some embodiments, the VHH molecule is attached to a detectable label, and detection of the label is used to measure displacement of the VHH molecule by the enzyme inhibitor. In some embodiments, the VHH molecule further comprises a detectable tag, and an antibody against the tag is used to measure displacement of the VHH molecule by the enzyme inhibitor. In some embodiments, the candidate enzyme inhibitor is a small organic compound. In some embodiments, the screening method identifies a candidate enzyme inhibitor that inhibits enzymatic or catalytic activity with a greater potency than the VHH molecule. In some embodiments, the solid support is a bead, a microwell plate, a chip or a microfluidics device.

In a further aspect, provided is an inhibitor of cystic fibrosis transmembrane conductance regulator (CFTR) inhibitory factor (Cif) comprising the structure selected from the group consisting of:

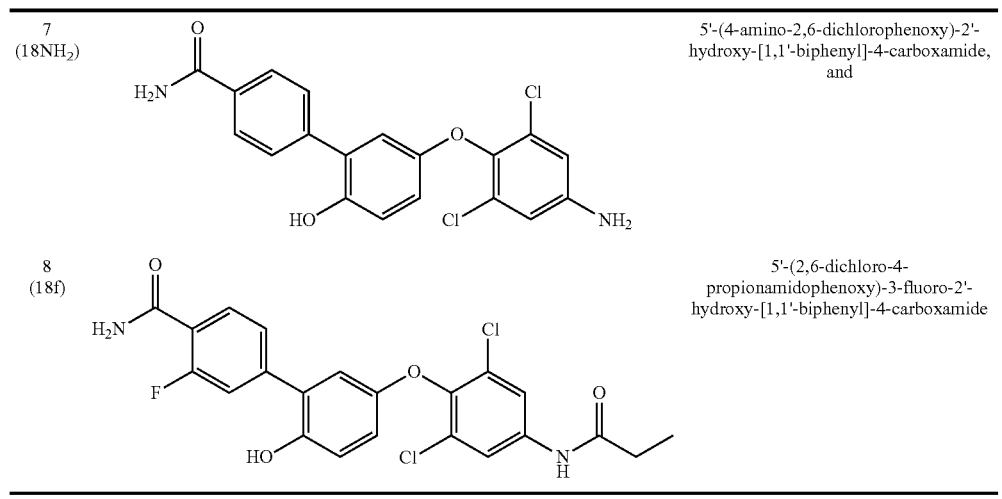

7 (18NH₂): 5'-(4-amino-2,6-dichlorophenoxy)-2'-hydroxy-[1,1'-biphenyl]-4-carboxamide, and 8 (18f): 5'-(2,6-dichloro-4-propionamidophenoxy)-3-fluoro-2'-hydroxy-[1,1'-biphenyl]-4-carboxamide In another aspect, provided is a pharmaceutical composition comprising one or both Cif inhibitors, e.g., compounds 7 and/or 8 as provided above and herein, or a pharmaceutically acceptable salt thereof, in a pharmaceutically acceptable carrier. In a further aspect, provided is a method of reducing, inhibiting, mitigating and/or reversing one or more symptoms associated with or caused by a *Pseudomonas* infection, comprising administering to the subject an effective amount of a composition comprising one or both Cif inhibitors, e.g., compounds 7 and/or 8 as provided above and herein. In some embodiments, the *Pseudomonas* infection is a *Pseudomonas aeruginosa* infection. IN some embodiments, the agent is administered via a route selected from the group consisting of intrapulmonary, inhalational, intravenous, intramuscular, subcutaneous, intradermal, transcutaneous, topical, intrathecal, intralesional, transmucosal, intra-arterial, intraperitoneal, intraventricular and intracranial.

Definitions

The terms "single domain antibody," "nanobody" refers to an antibody comprising one variable domain (VH) of a heavy-chain antibody ("VHH") obtained from camelids. Antibody proteins obtained from members of the camel and dromedary (*Camelus baclrianus* and *Camelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See, PCT/EP93/02214 (published as WO 94/04678).

The term 'VHH' refers to the single heavy chain variable domain antibodies devoid of light chains. Generally, a VHH is an antibody of the type that can be found in Camelidae or cartilaginous fish which are naturally devoid of light chains or to a synthetic and non-immunized VHH which can be constructed accordingly. Each heavy chain comprises a variable region encoded by V-, D- and J exons. The VHH may be a natural VHH antibody, preferably a Camelid antibody, or a recombinant protein comprising a heavy chain variable domain.

Structurally, "cystic fibrosis transmembrane conductance regulator (CFTR) inhibitory factor," "CFTR inhibitory factor," or "Cif" interchangeably refer to nucleic acids and polypeptide polymorphic variants, alleles, mutants, and interspecies homologs that: (1) have an amino acid sequence that has greater than about 80% amino acid sequence identity, for example, 81%, 82%, 83%, 84%, 85%, 86%, 87%, 88%, 89%, 90%, 91%, 92%, 93%, 94%, 95%, 96%, 97%, 98% or 99% or greater amino acid sequence identity, preferably over a region of at least about 25, 50, 100, 200, 300, or more amino acid residues, or over the full-length, to an Cif amino acid sequence, (e.g., NCBI Reference Sequence: NP_251624.1 and GenBank Accession No. CTQ36962.1). (2) bind to antibodies, e.g., polyclonal or monoclonal antibodies, raised against an immunogen comprising an amino acid sequence of a Cif polypeptide; or an amino acid sequence encoded by a Cif nucleic acid, and conservatively modified variants thereof; (3) specifically hybridize under stringent hybridization conditions to an anti-sense strand corresponding to a nucleic acid sequence encoding a Cif protein, and conservatively modified variants thereof; (4) have a nucleic acid sequence that has greater than about 80%, preferably greater than about 81%, 82%, 83%, 84%, 85%, 86%, 87%, 88%, 89%, 90%, 91%, 92%, 93%, 94%, 95%, 96%, 97%, 98%, 99%, or higher nucleotide sequence identity, preferably over a region of at least about 25, 50, 100, 200, 500, or more nucleotides, or over the full-length, to a Cif nucleic acid. Functionally, Cif refers to an epoxide hydrolase virulence factor secreted by *Pseudomonas* bacteria, particularly *Pseudomonas aeruginosa* bacteria. Cif can decrease levels of CFTR on the membrane of host airway epithelial cells, resulting in an altered microenvironment and lower host immune defense, facilitating *Pseudomonas* biofilm formation and chronic infection. See, e.g., Bahl, et al., *Cornea*. (2017) 36(3):358-362; Bahl, et al., *Biochemistry*. (2016) 55(5):788-97; and Bahl, et al., *Angew Chem Int Ed Engl*. (2015) 54(34):9881-5.

The phrase "sequence identity," in the context of two nucleic acids or polypeptides, refers to two or more sequences or subsequences that have a certain level of nucleotide or amino acid residue identity, when compared and aligned for maximum correspondence, as measured using one of the following sequence comparison algorithms or by visual inspection. Preferably, the aligned sequences share at least 90% sequence identity, for example, at least 95%, 96%, 97%, 98%, 99% or 100% sequence identity. The sequence identity can exist over a region of the sequences that is at least about 10, 20 or 50 residues in length, sometimes over a region of at least about 100 or 150 residues. In some embodiments, the sequences share a certain level of sequence identity over the entire length of the sequence of interest.

For sequence comparison, typically one sequence acts as a reference sequence (e.g., SEQ ID NOs: 1-72), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel, et al. Editor, Current Protocols in Molecular Biology, USA, 1984-2017). Another example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (on the World Wide Web at ncbi.nhn nih.gov/) (see Henikoff & Henikoff, Proc. Natl. Acad. Sci. USA 89:10915 (1989)).

With respect to the numbering of positions in a given amino acid polymer or nucleic acid polymer, the terms "corresponding to," "corresponds to," is in "reference to," or is "relative to" the numbering of a selected amino acid polymer or nucleic acid polymer refers to the position of any given polymer component (e.g., amino acid, nucleotide, also referred to generically as a "residue") as designated by reference to the same or to an equivalent position in the selected amino acid or nucleic acid polymer, rather than by the actual numerical position of the component in the given polymer. Thus, for example, the numbering of a given amino acid position in a given polypeptide sequence corresponds to the same or equivalent amino acid position in a selected polypeptide sequence used as a reference sequence.

An "equivalent position" (for example, an "equivalent amino acid position" or "equivalent nucleic acid position" or "equivalent residue position") is defined herein as a position (such as, an amino acid position or nucleic acid position or residue position) of a test polypeptide (or test polynucleotide) sequence which aligns with a corresponding position of a reference polypeptide (or reference polynucleotide) sequence, when optimally aligned using an alignment algorithm as described herein. The equivalent amino acid position of the test polypeptide need not have the same numerical position number as the corresponding position of the reference polypeptide; likewise, the equivalent nucleic acid position of the test polynucleotide need not have the same numerical position number as the corresponding position of the reference polynucleotide.

Two polypeptide sequences are "optimally aligned" or in "optimal alignment" when they are aligned using defined parameters, i.e., a defined amino acid substitution matrix, gap existence penalty (also termed gap open penalty), and gap extension penalty, so as to arrive at the highest similarity score possible for that pair of sequences. The BLOSUM62 matrix (Henikoff and Henikoff (1992) Proc. Natl. Acad. Sci. USA 89(22):10915-10919) is often used as a default scoring substitution matrix in polypeptide sequence alignment algorithms (such as BLASTP). The gap existence penalty is imposed for the introduction of a single amino acid gap in one of the aligned sequences, and the gap extension penalty is imposed for each residue position in the gap. Unless otherwise stated, alignment parameters employed herein are: BLOSUM62 scoring matrix, gap existence penalty=11, and gap extension penalty=1. The alignment score is defined by the amino acid positions of each sequence at which the alignment begins and ends (e.g. the alignment window), and optionally by the insertion of a gap or multiple gaps into one or both sequences, so as to arrive at the highest possible similarity score.

With respect to the determination of an amino acid position by optimal alignment with a reference sequence, the amino acid position in a test amino acid sequence corresponds to the position in the reference sequence with which the residue is paired in the alignment. The "position" is denoted by a number that sequentially identifies each amino acid in the reference sequence based on its position relative to the N-terminus. Owing to deletions, insertions, truncations, fusions, and the like that must be taken into account when determining an optimal alignment, in general the amino acid residue number in a test sequence is determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" as used herein applies to amino acid sequences. One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

The term "polynucleotide" or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs.

As used herein, "operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a heterologous polynucleotide encoding a polypeptide of interest (e.g., a therapeutic polypeptide, e.g., an antibody or antibody fragment), if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, "vector" means a construct, which is capable of delivering, and preferably expressing, one or more gene(s) or sequence(s) of interest (e.g., a therapeutic polypeptide) in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Green and Sambrook, Molecular Cloning: A Laboratory Manual, 4th ed., Cold Spring Harbor, 2012).

As used herein, "administering" refers to local and systemic administration, e.g., including enteral, parenteral, pulmonary, and topical/transdermal administration. Routes of administration for the anti-Cif VHH molecules, fusion proteins and/or functional variants thereof described herein include, e.g., oral (per os (P.O.)) administration, nasal or inhalation administration, administration as a suppository, topical contact (including to and around the eyes), transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intrapulmonary, intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering the anti-Cif VHH molecules, fusion proteins and/or functional variants thereof to a mammal so that the compound or composition is delivered to sites in the body, including the targeted site of pharmaceutical action, via the circulatory system. Systemic administration includes, but is not limited to, oral, intrapulmonary, intranasal, rectal and parenteral (e.g., other than through the alimentary tract, such as, inhalational, intravenous, intramuscular, intra-arterial, intraperitoneal, intraventricular, transdermal and subcutaneous) administration.

The term "co-administering" or "concurrent administration", when used, for example with respect to the anti-Cif VHH molecules, fusion proteins and/or functional variants thereof, refers to administration of the compound and/or analogs and the active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g., in the plasma) at a significant fraction (e.g., 20% or greater, preferably 30% or 40% or greater, more preferably 50% or 60% or greater, most preferably 70% or 80% or 90% or greater) of their maximum serum concentration for any given dose.

The term "effective amount" or "pharmaceutically effective amount" refer to the amount and/or dosage, and/or dosage regime of the anti-Cif VHH molecules, fusion proteins and/or functional variants thereof necessary to bring about the desired result e.g., an amount sufficient to mitigating in a mammal one or more symptoms associated a Pseudomonas infection, or an amount sufficient to lessen the severity or delay the progression of a Pseudomonas infection, an amount sufficient to reduce the risk or delaying the onset, and/or reduce the ultimate severity of a Pseudomonas infection (e.g., prophylactically effective amounts).

The phrase "cause to be administered" refers to the actions taken by a medical professional (e.g., a physician), or a person controlling medical care of a subject, that control and/or permit the administration of the anti-Cif VHH molecules, fusion proteins and/or functional variants thereof to the subject. Causing to be administered can involve diagnosis and/or determination of an appropriate therapeutic or prophylactic regimen, and/or prescribing particular anti-Cif VHH molecules, fusion proteins and/or functional variants thereof for a subject. Such prescribing can include, for example, drafting a prescription form, annotating a medical record, and the like.

As used herein, the terms "treating" and "treatment" refer to delaying the onset of, retarding or reversing the progress of, reducing the severity of, or alleviating or preventing either the disease or condition to which the term applies, or one or more symptoms of such disease or condition (e.g., a Pseudomonas infection).

The term "mitigating" refers to reduction or elimination of one or more symptoms of that pathology or disease, and/or a reduction in the rate or delay of onset or severity of one or more symptoms of that pathology or disease, and/or the prevention of that pathology or disease (e.g., a Pseudomonas infection).

As used herein, the phrase "consisting essentially of" refers to the genera or species of active pharmaceutical agents recited in a method or composition, and further can include other agents that, on their own do not substantial activity for the recited indication or purpose.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments the subject may not be under the care or prescription of a physician or other healthworker.

BRIEF DESCRIPTION OF THE DRAWINGS

FIGS. 2A-B illustrate amino acid sequences of 18 Cif-selective VHHs (SEQ ID NOS 1, 5, 9, 13, 17, 21, 25, 29, 33, 37, 41, 45, 49, 53, 57, 61, 65, and 69, respectively, in order of appearance). FR indicates framework, or conserved domain of the antibody; CDR is the complementarity-determining region, a variable domain of the antibody responsible for selective recognition of the target analyte; TAG includes 6xHistag (SEQ ID NO: 90) and hemagglutinin (HA) tag.

FIGS. 4A-B illustrate surface plasmon resonance (SPR) curves. A. Clone 113, concentrations tested: 0.05, 0.5, 2, 8, 20 nM; B. Clone 219, concentrations tested 0.2, 1, 3, 10, 20 nM. Binding assays were performed at a flow rate of 30 µL/min with 300 s injection time of VHHs followed by washing with buffer for 1200 s. Sodium phosphate buffer (20 mM pH 7.0) containing 50 mM NaCl and 0.05% (v/v) TWEEN 20 was used as a running buffer in the assay.

FIG. 5 illustrates amino acid sequences for inhibitory nanobodies 113 (SEQ ID NO: 13) and 219 (SEQ ID NO:

41). FR indicates framework, or conserved domain of the nanobody; CDR stands for complementarity-determining region, a variable domain of the nanobody responsible for selective recognition of the target analyte; TAG includes 6×His tag (SEQ ID NO: 90) and hemagglutinin (HA) tag.

Figure 6A:
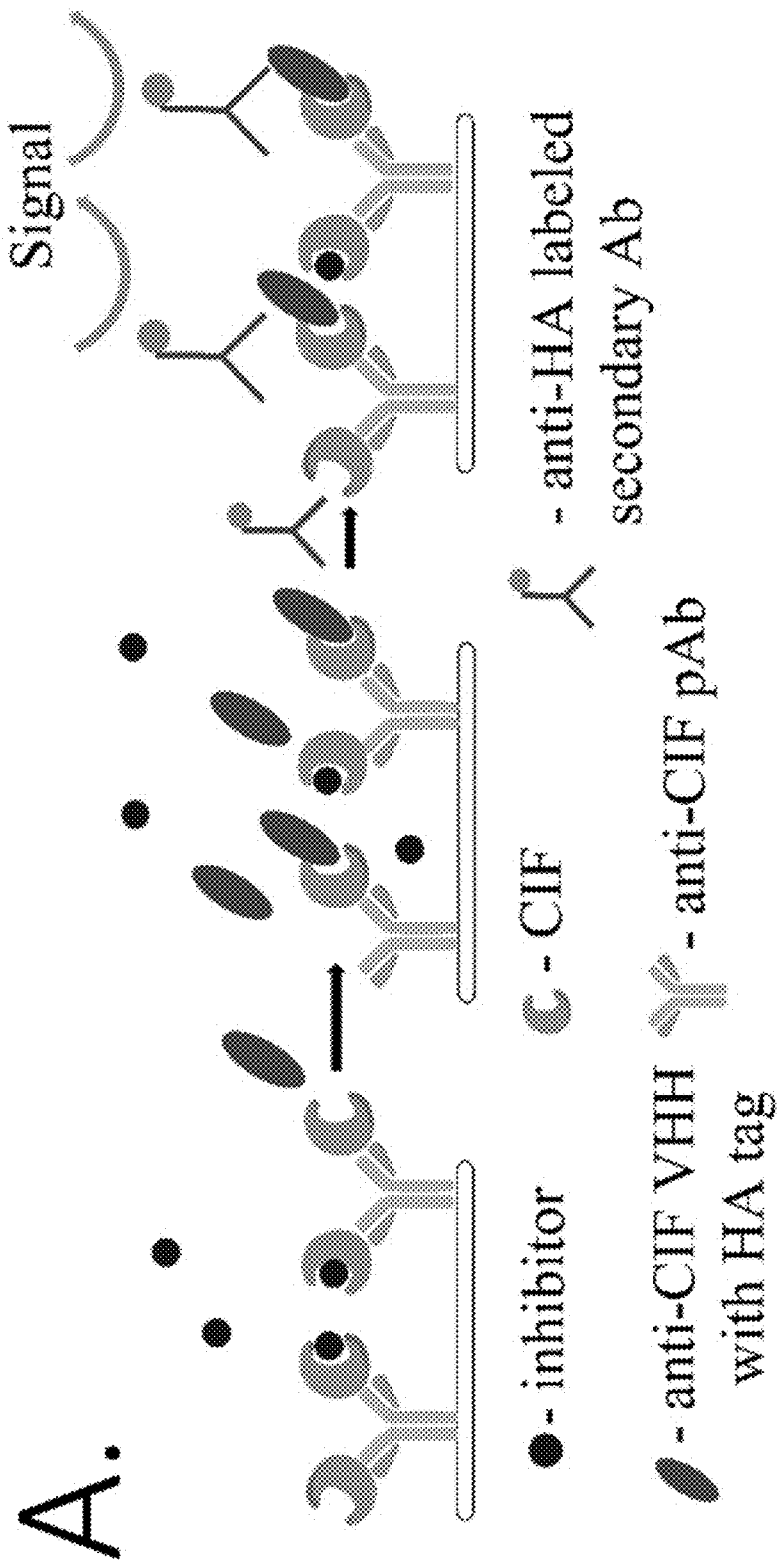
Figure 6B:
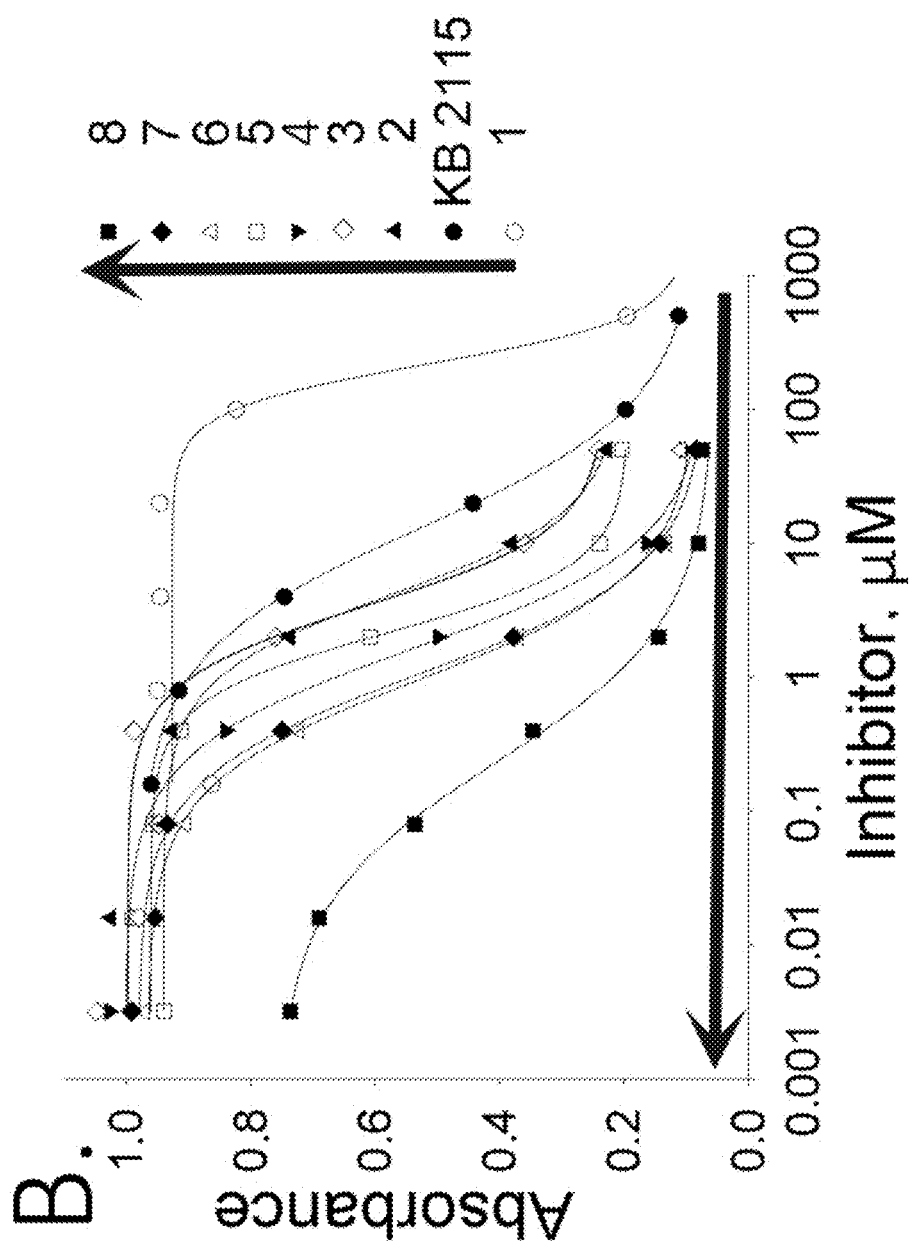

FIGS. 6A-B illustrate a schematic of displacement sandwich ELISA (dsELISA). A. Workflow scheme of the assay: the plate is coated with anti-Cif pAb and Cif, followed by incubation with the small molecule inhibitor and the nanobody. Unbound material is washed out and the bound nanobody is reveled with secondary anti-HA antibody labeled with HRP. Conditions: anti-Cif pAb 0.3 µg/well; Cif 20 ng/mL in PBS; VHH 5 ng/well in PBS; anti-HA mAb dilution 1:3000 in PBST. B. Inhibition curves for the tested compounds reveal high competitive capacity of the compound 8, followed by 7 and 6. Blue arrows indicate the order of increasing potency, where compound 8 is the most potent and compound 1 is the less potent. Compounds with higher potency have inhibitory curves shifted to the left of the graph.

Figure 7:
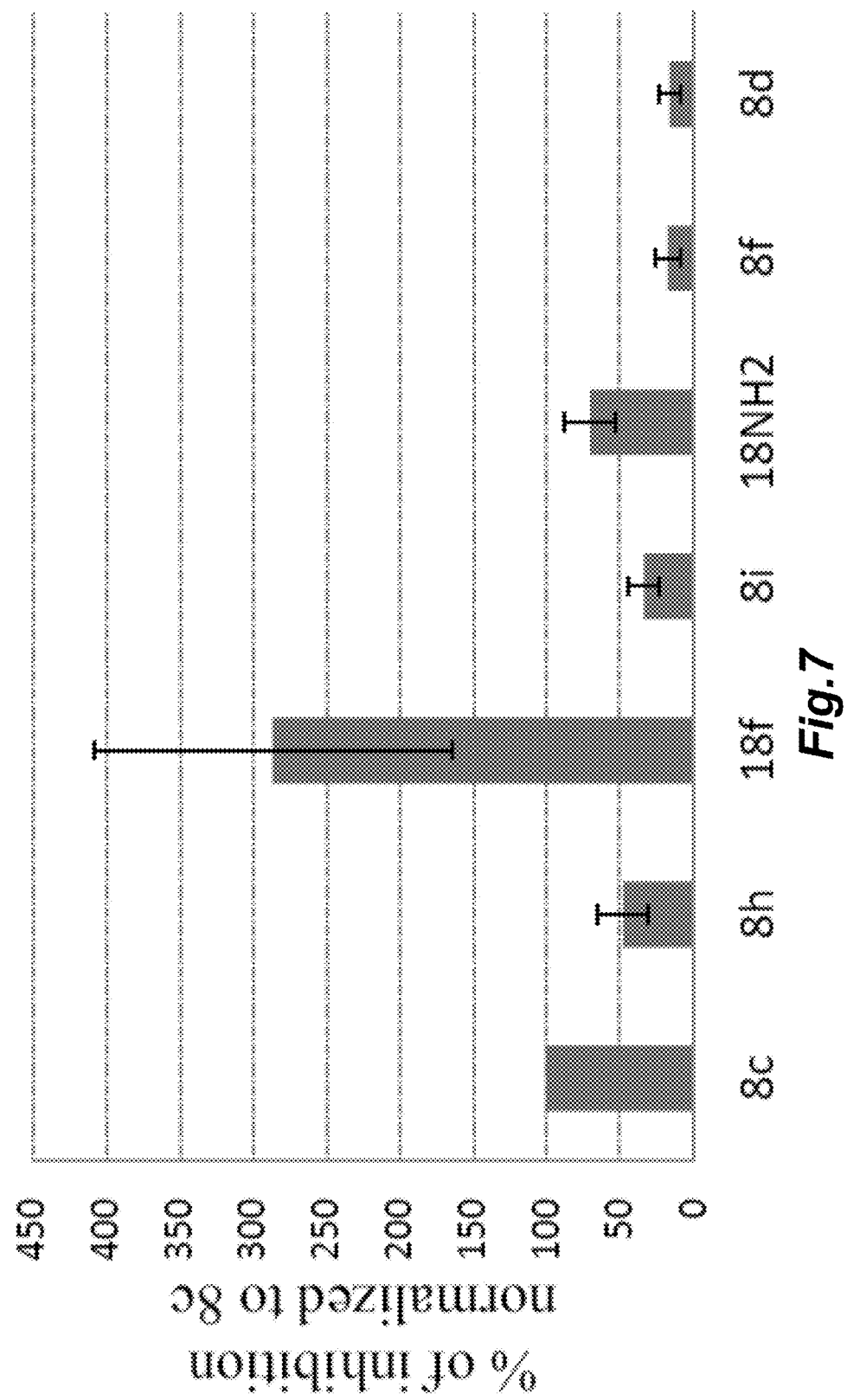

FIG. 7 illustrates day-to-day variation of the signal normalized to the signal of the compound 8c (data include measurements some performed over period of 5 months and some within a week), mean±SD, n=3-4.

DETAILED DESCRIPTION

1. Introduction

Drug identification and development is a research direction that always requires faster, cheaper, more selective and sensitive tools to keep advancing and improving health care. High-throughput screening methods for identification of selective small molecule inhibitors of biologically active proteins often rely on their efficient catalytic properties. However, there is lack of screening tools combining low cost and high sensitivity for drugs targeting low activity proteins. Here we report a screening and detection method involving nanobodies allowing sensitive screening of small molecule compounds targeting active site of the cystic fibrosis transmembrane conductance regulator (CFTR) inhibitory factor (Cif), that is associated with the establishment of chronic inflammation in the lung following colonization with *Pseudomonas Aeruginosa*.

A nanobody inhibiting the catalytic activity of Cif was selected and used in a displacement sandwich ELISA (dsELISA), where the inhibitory nanobody also interferes with the binding of a small-molecule inhibitor to the active site of Cif. The dsELISA assay correlates strongly with a conventional fluorogenic assay in predicting the inhibitory potency of the tested compounds. However, the novel dsELISA is an order of magnitude more sensitive and allows the identification and ranking of potent inhibitors missed by the classic assay method. These data were supported with surface plasmon resonance and Octet biolayer measurement techniques. The novel method described herein relies solely on the binding properties of the specific neutralizing nanobody, and thus is applicable to any pharmacological target for which such a nanobody can be found, independent of any requirement for catalytic activity.

Using seven compounds known inhibitors of Cif we showed a strong agreement between conventional fluorescent method and csELISA in predicting inhibitory potency of the tested compounds. The csELISA method allowed identification of two new compounds, one with 10-fold higher inhibitory potency. These data were confirmed with surface plasmon resonance and Octet biolayer measurement techniques. In addition to the catalytic proteins like enzymes, the competitive sandwich immunoassay can be applied to a larger class of proteins, including receptors, transporters, other non-catalytic proteins since the screening method does not rely on other properties except the chemistry of the binding site.

2. Compositions

Provided are VHH or nanobodies that specifically bind to cystic fibrosis transmembrane conductance regulator (CFTR) inhibitory factor (Cif), a protein that is produced by *Pseudomonas* bacteria, particularly *Pseudomonas aeruginosa*, and which contributes to *Pseudomonas* infection and pathogenicity in a host. Further provided are fusion proteins, conjugates, nanoparticles and liposomes comprising the anti-Cif VHH and polynucleotides encoding the anti-Cif VHH and fusion proteins thereof.

Nanobodies are single domain antibodies (sdAb) typically consisting of a single monomeric variable antibody domain. Like whole antibodies (intact immunoglobulins), nanobodies are able to bind selectively to a specific antigen. With a molecular weight typically ranging from about 12 kDa to about 15 kDa, the single-domain nanobodies are much smaller than intact immunoglobulins which are typically composed of two heavy protein chains and two light chains. Nanobodies are also typically smaller than Fab fragments (~50 kDa, one light chain and half a heavy chain) and single-chain variable fragments (~25 kDa, two variable domains, one from a light and one from a heavy chain). Methods of producing nanobodies are described, inter alia, by Harmsen and Haard (2007) *Appl. Microbiol. Biotechnol.* 77 (1): 13-22).

Initially, nanobodies were engineered from heavy-chain antibodies found in camelids. These are called VHH fragments. Cartilaginous fishes also have heavy-chain antibodies (immunoglobulin new antigen receptor (IgNAR)'), from which single-domain antibodies called $V_{NAR}$ fragments can be obtained. An alternative approach is to split the dimeric variable domains from a common human or other mammal (e.g., mice, rabbits, etc.) into monomers. Although most research into single-domain antibodies is based on heavy chain variable domains, nanobodies derived from light chains have also been shown to bind specifically to target epitopes (see, e.g., Möller et al. (2010) *J. Biol. Chem.* 285(49): 38348-38361). Single-domain camelids antibodies have been shown to be just as specific as a regular antibody and in some cases they are more robust. As well, they are easily isolated using the same phage panning procedure used for traditional antibodies, allowing them to cultured in vitro in large concentrations. The smaller size and single domain make these antibodies easier to transform into bacterial cells for bulk production, making them particularly useful for research purposes.

Typically the single-domain antibody is a peptide chain about 110 amino acids long, comprising one variable domain (VH) of a heavy-chain antibody, or of a common IgG. These peptides have similar affinity to antigens as whole antibodies, but are more heat-resistant and stable towards detergents and high concentrations of urea. Those derived from camelid and fish antibodies are less lipophilic and more soluble in water, which, without being bound to a particular theory, is believed to be due to their complementarity determining region 3 (CDR3), which forms an extended loop covering the lipophilic site that normally binds to a light chain (see, e.g., Dolk et al. (2005) *Appl.*

*Environ. Microbiol.* 71(1): 442-450; Stanfield et al. (2004) *Science*, 305(5691): 1770-1773).

The comparatively low molecular mass of nanobodies often leads to better permeability in tissues, and to a short plasma half-life since they are eliminated renally. Unlike whole antibodies, they do not show complement system triggered cytotoxicity because they lack an Fc region. However, in certain embodiments, it is contemplated that an immunoglobulin Fc region (or variant Fc region) can be fused to the nanobody to provide additional functionality. Camelid and fish derived sdAbs are able to bind to hidden antigens that are may not be accessible to whole antibodies, for example to the active sites of enzymes. It is believed that this property has been shown to result from their extended CDR3 loop, which is able to penetrate such sites (see, e.g., Stanfield et al. (2004) *Science* 305(5691): 1770-1773; Desmyter et al. (1996) *Nat. Struct. Biol.* 3(9): 803-811).

a. Anti-Cif VHH or Anti-Cif Nanobodies

Provided are recombinant, synthetic and/or non-natural VHH or nanobody molecules that specifically bind to cystic fibrosis transmembrane conductance regulator (CFTR) inhibitory factor (Cif). In some embodiments, the Cif is produced by a *Pseudomonas* bacterium. In some embodiments, the Cif is produced by a *Pseudomonas aeruginosa* bacterium.

Functionally, in some embodiments, the anti-Cif VHH or nanobody binds to Cif with a KD of 0.2 nM or less, e.g., 0.19 nM, 0.18 nM, 0.17 nM, 0.16 nM, 0.15 nM, 0.14 nM, 0.13 nM, 0.12 nM, 0.11 nM, 0.10 nM, 0.09 nM, 0.08 nM, or less. In some embodiments, the VHH reduces or inhibits the enzymatic activity of Cif. In some embodiments, the VHH inhibits the enzymatic activity of Cif with and IC50 concentration of 3.0 µM or less, e.g., 2.9 µM, 2.8 µM, 2.7 µM, 2.6 µM, 2.5 µM, 2.4 µM, 2.3 µM, 2.2 µM, 2.1 µM, 2.0 µM, 1.9 µM, 1.8 µM, 1.7 µM, 1.6 µM, 1.5 µM, 1.4 µM, 1.3 µM, 1.2 µM, 1.1 µM, 1.0 µM, 0.9 µM, 0.8 µM, 0.7 µM, 0.6 µM, 0.5 µM, or less. In some embodiments, the VHH inhibits the enzymatic activity of Cif with and IC90 concentration of 4.0 µM or less, e.g., 3.9 µM, 3.8 µM, 3.7 µM, 3.6 µM, 3.5 µM, 3.4 µM, 3.3 µM, 3.2 µM, 3.1 µM, 3.0 µM, 2.9 µM, 2.8 µM, 2.7 µM, 2.6 µM, 2.5 µM, or less.

Structurally, in some embodiments, the VHH comprises:

a) a CDR1 comprising SEQ ID NO:2, a CDR2 comprising SEQ ID NO:3 and a CDR3 comprising SEQ ID NO:4;

b) a CDR1 comprising SEQ ID NO:6, a CDR2 comprising SEQ ID NO:7 and a CDR3 comprising SEQ ID NO:8;

c) a CDR1 comprising SEQ ID NO:10, a CDR2 comprising SEQ ID NO:11 and a CDR3 comprising SEQ ID NO:12;

d) a CDR1 comprising SEQ ID NO:14, a CDR2 comprising SEQ ID NO:15 and a CDR3 comprising SEQ ID NO:16;

e) a CDR1 comprising SEQ ID NO:18, a CDR2 comprising SEQ ID NO:19 and a CDR3 comprising SEQ ID NO:20;

f) a CDR1 comprising SEQ ID NO:22, a CDR2 comprising SEQ ID NO:23 and a CDR3 comprising SEQ ID NO:24;

g) a CDR1 comprising SEQ ID NO:26, a CDR2 comprising SEQ ID NO:27 and a CDR3 comprising SEQ ID NO:28;

h) a CDR1 comprising SEQ ID NO:30, a CDR2 comprising SEQ ID NO:31 and a CDR3 comprising SEQ ID NO:32;

i) a CDR1 comprising SEQ ID NO:34, a CDR2 comprising SEQ ID NO:35 and a CDR3 comprising SEQ ID NO:36;

j) a CDR1 comprising SEQ ID NO:38, a CDR2 comprising SEQ ID NO:39 and a CDR3 comprising SEQ ID NO:40;

k) a CDR1 comprising SEQ ID NO:42, a CDR2 comprising SEQ ID NO:43 and a CDR3 comprising SEQ ID NO:44;

l) a CDR1 comprising SEQ ID NO:46, a CDR2 comprising SEQ ID NO:47 and a CDR3 comprising SEQ ID NO:48;

m) a CDR1 comprising SEQ ID NO:50, a CDR2 comprising SEQ ID NO:51 and a CDR3 comprising SEQ ID NO:52;

n) a CDR1 comprising SEQ ID NO:54, a CDR2 comprising SEQ ID NO:55 and a CDR3 comprising SEQ ID NO:56;

o) a CDR1 comprising SEQ ID NO:58, a CDR2 comprising SEQ ID NO:59 and a CDR3 comprising SEQ ID NO:60;

p) a CDR1 comprising SEQ ID NO:62, a CDR2 comprising SEQ ID NO:63 and a CDR3 comprising SEQ ID NO:64;

q) a CDR1 comprising SEQ ID NO:66, a CDR2 comprising SEQ ID NO:67 and a CDR3 comprising SEQ ID NO:68; or r) a CDR1 comprising SEQ ID NO:70, a CDR2 comprising SEQ ID NO:71 and a CDR3 comprising SEQ ID NO:72.

Structurally, in some embodiments, the VHH comprises an amino acid sequence having at least 80% sequence identity, e.g., at least 85%, 90%, 91%, 92%, 93%, 94%, 95%, 96%, 97%, 98%, 99% or 100% sequence identity, to an amino acid selected from the group consisting of:

a) amino acid residues 1-134 of SEQ ID NO:1;
b) amino acid residues 1-127 of SEQ ID NO:5;
c) amino acid residues 1-132 of SEQ ID NO:9;
d) amino acid residues 1-133 of SEQ ID NO:13;
e) amino acid residues 1-126 of SEQ ID NO:17;
f) amino acid residues 1-127 of SEQ ID NO:21;
g) amino acid residues 1-129 of SEQ ID NO:25;
h) amino acid residues 1-127 of SEQ ID NO:29;
i) amino acid residues 1-127 of SEQ ID NO:33;
j) amino acid residues 1-127 of SEQ ID NO:37;
k) amino acid residues 1-127 of SEQ ID NO:41;
l) amino acid residues 1-127 of SEQ ID NO:45;
m) amino acid residues 1-126 of SEQ ID NO:49;
n) amino acid residues 1-133 of SEQ ID NO:53;
o) amino acid residues 1-127 of SEQ ID NO:57;
p) amino acid residues 1-126 of SEQ ID NO:61;
q) amino acid residues 1-127 of SEQ ID NO:65; and
r) amino acid residues 1-127 of SEQ ID NO:69.

b. Fusion Proteins

Further provided are fusion proteins comprising an anti-Cif VHH operably linked to a second polypeptide or peptide. In some embodiments, the second polypeptide comprises a detectable protein tag or peptide tag. Such tags can be useful for purification and/or detection.

Numerous peptide tags are known in the art and find use. Illustrative peptide tags that can be operably linked to an anti-Cif VHH include without limitation AviTag (BirA biotinylation sequence; GLNDIFEAQKIEWHE, SEQ ID NO:73); Calmodulin-tag (KRRWKKNFIAVSAANRFK-KISSSGAL, SEQ ID NO:74); polyglutamate tag (EEEEEE, SEQ ID NO:75); E-tag (GAPVPYPDPLEPR, SEQ ID NO:76); FLAG-tag (DYKDDDDK, SEQ ID NO:77); hemagglutinin (HA)-tag (YPYDVPDYA, SEQ ID NO:78); His-tag, 5-10 histidines ($His_{5-10}$, SEQ ID NO:79), Myc-tag (EQKLISEEDL, SEQ ID NO:80); NE-tag (TKEN-PRSNQEESYDDNES, SEQ ID NO:81); S-tag (KET-AAAKFERQHMDS, SEQ ID NO:82); streptavidin binding protein (SBP)-tag (MDEKTTGWRGGHVVEG-LAGELEQLRARLEHHPQGQREP, SEQ ID NO:83); Softag 1 (SLAELLNAGLGGS, SEQ ID NO:84); Softag 3

(TQDPSRVG; SEQ ID NO:85); Strep-tag (WSHPQFEK, SEQ ID NO:86); V5 tag (GKPIPNPLLGLDST, SEQ ID NO:87); VSV-tag (YTDIEMNRLGK; SEQ ID NO:88); and Xpress tag (DLYDDDDK, SEQ ID NO:89).

Additionally, numerous protein tags are known in the art and find use. Illustrative protein tags that can be operably linked to an anti-Cif VHH include without limitation BCCP (Biotin Carboxyl Carrier Protein), Glutathione-S-transferase-tag, a fluorescent protein-tag (including, e.g., green fluorescent protein, yellow fluorescent protein, red fluorescent protein (mCherry, mEos2, mRuby2, mRuby3, mClover3, mApple, mKate2, mMaple, mCardinal, mNeptune), mTurquoise, mVenus), HaloTag, Maltose binding protein-tag, Nus-tag, Thioredoxin-tag and an immunoglobulin Fc-tag.

In embodiments where the anti-Cif is to be used for therapy, e.g., to prevent, reduce, inhibit, mitigate or reverse a *Pseudomonas* infection, particularly a *Pseudomonas aeruginosa* infection, the fusion protein can be a bi-specific VHH or bi-specific immunoglobulin, comprising an anti-Cif VHH and a second VHH molecule or immunoglobulin that specifically binds to a complement receptor (e.g., a bispecific VHH fusion that can concurrently binds to Cif and a complement receptor). In some embodiments, the fusion protein further comprises a VHH molecule that specifically binds to the complement receptor CD11b/CD18 (Mac-1) (e.g., a bispecific VHH fusion that can concurrently binds to Cif and Mac-1).

c. Polynucleotides Encoding Anti-Cif VHH or Anti-Cif Nanobodies, and Fusion Proteins Thereof Further provided are polynucleotides encoding the anti-Cif VHH and fusion proteins thereof, as described above and herein. The polynucleotides can be synthetically or recombinantly produced, according to methods known in the art. Further, the sequences of the polynucleotides can be codon-biased or optimized, utilizing degeneracy of genetic coding, to increase levels of expression in a desired host cell (e.g., bacterial, mammalian, insect, plant or algae).

d. Conjugates

In some embodiments, the anti-Cif VHH are provided as a conjugate. The conjugate can be a therapeutic conjugate and/or a diagnostic conjugate.

In diagnostic conjugates, the anti-Cif VHH is linked or attached, covalently or non-covalently, to a detectable label. Illustrative detectable labels include fluorophores, chemoluminescent moieties, radioactive isotopes, quantum dots, and enzymes.

In therapeutic conjugates, the anti-Cif VHH is linked or attached, covalently or non-covalently, to a pharmacologically active agent. Illustrative agents include inhibitors of Cif and antibiotics. Antibiotics useful against *Pseudomonas aeruginosa* include without limitation, aminoglycosides (e.g., gentamicin, amikacin, tobramycin), quinolones (e.g., ciprofloxacin, levofloxacin), cephalosporins (e.g., ceftazidime, cefepime, cefoperazone, cefpirome, ceftobiprole), carboxypenicillins (e.g., carbenicillin and ticarcillin), ureidopenicillins (e.g., mezlocillin, azlocillin, and piperacillin), carbapenems (e.g., meropenem, imipenem, doripenem), polymyxins (e.g., polymyxin B and colistin), and monobactams (e.g., aztreonam). Illustrative Cif inhibitors include without limitation the compounds listed in Table 7. Additional Cif inhibitors that can be linked or attached to the anti-Cif VHH are identified in Kitamura, et al., *J Med Chem.* (2016) 59(10):4790-; Intl. Patent Publ. No. WO 2013/155047 and U.S. Patent Publ. No. 2015/0045389.

e. Nanoparticles/Liposomes

In various embodiments, the anti-Cif VHH, conjugate or fusion protein is attached to or encapsulated within a liposome. Liposomes include emulsions, foams, micelles, insoluble monolayers, liquid crystals, phospholipid dispersions, lamellar layers and the like. In these preparations the composition to be delivered is incorporated as part of a liposome, alone or in conjunction with a molecule which binds to a desired target, such as antibody, or with other therapeutic or immunogenic compositions. Liposomes for use are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., Ann. Rev. Biophys. Bioeng. 9:467 (1980), U.S. Pat. Nos. 4,235,871; 4,501,728; 4,837,028 and 5,019,369. The anti-Cif VHH, conjugate or fusion protein can be integrated into, attached or conjugated directly to the liposome using methods known in the art. Anti-CD22 antibodies conjugated to liposome-encapsulated doxorubicin has been tested in in vivo animal models. See, e.g., O'Donnell, et al., Invest New Drugs. (2010) 28(3):260-7; O'Donnell, et al., Cancer Immunol Immunother. (2009) 58(12):2051-8 and Tuscano, et al., Clin Cancer Res. (2010) 16(10):2760-8. Those of skill in the art will readily appreciate that the anti-CD22 targeting moiety can be replaced with an anti-Cif VHH, and the doxorubicin can be exchanged with another therapeutic agent(s) of interest.

In some embodiments, the anti-Cif VHH, conjugate or fusion protein is attached or conjugated to, or encapsulated within a liposome or a nanoparticle that encapsulates the therapeutic agent. Nanoparticles for encapsulation and delivery of a therapeutic agent are known in the art and can find use. Illustrative nanoparticles include without limitation, e.g., semiconductor quantum dots (QDs), silicon (Si) nanoparticles (Park, et al., *Nature Materials* (2009) 8:331-336; Tu, et al., *JACS*, (2010) 132:2016-2023; Zhang, et al., *JACS*, (2007) 129:10668; Singh M P et al., ACS Nano, (2012) In press, (DOI: 10.1021/nn301536n); Rosso-Vasic, et al., *J. Mater. Chem.* (2009) 19:5926-5933; Bhattacharjee S., et al., Nanotoxicology, (2011) DOI 10.3109/17435390.2011.633714, 1-14; Chandra, et al., Nanoscale (2011) 3:1533-1540), polylactide-co-glycolide nanoparticles for controlled delivery of anticancer agents (Dinarvand, et al., *Int J Nanomedicine.* 2011; 6:877-95); polyethyleneimine (PEI)-As(2)O(3)/Mn(0.5)Zn(0.5)Fe(2)O(4) magnetic nanoliposomes (Wang, et al., *Int J Nanomedicine.* 2011; 6:871-5); redox-responsive poly(ethylene glycol)-b-poly(lactic acid) (MPEG-SS-PLA) nanoparticles (Song, et al., *Colloids Surf B Biointerfaces.* 2011, PMID 21719259); Thiolated Pluronic (Plu-SH) nanoparticles (Abdullah-Al-Nahain, et al., *Macromol Biosci.* 2011, PMID 21717576); and mesoporous silica nanoparticles (MSNs) (Wu, et al., *Chem Commun* (Camb). 2011, PMID 21716992). In one embodiment, the anti-Cif VHH, conjugate or fusion protein is conjugated to or encapsulated within biocompatible nanomicelles comprised of cholic acid, lysine and polyethylene glycol (PEG) covalently conjugated together, e.g., described in Xiao, et al., *Biomaterials* (2009) 30:6006-6016; and Luo, et al., *Bioconjug Chem* (2010) 21:1216-1224. Further nanomicelles that find use are described, e.g., in PCT Patent Publ. WO 2010/039496.

In one embodiment, the anti-Cif VHH, conjugate or fusion protein is attached or conjugated to or encapsulated within biocompatible nanomicelles comprised of cholic acid, lysine and polyethylene glycol (PEG) covalently conjugated together, e.g., as described in Xiao, et al., *Biomaterials* (2009) 30:6006-6016; and Luo, et al., *Bioconjug Chem* (2010) 21:1216-1224. Recently, a biocompatible nanomicelle drug delivery system comprised of a unique amphiphilic polymers called telodendrimers was developed [Xiao, et al., *Biomaterials* (2009) 30:6006-6016; Luo, et al., *Bioconjug Chem* (2010) 21:1216-1224]. Telodendrimers consist of cholic acid, lysine and polyethylene glycol (PEG) covalently conjugated together, which impart the ability to self-assemble into a water-soluble spheroid with a hydrophobic core capable of sequestering many types of drugs. Cholic acid, a primary component of bile acid, possesses a facial amphiphilic structure: a rigid steroid scaffold with four hydrophilic groups on one surface, and hydrophobic methyl groups on the other surface of the scaffold. Lysine is a natural amino acid. PEG is biocompatible and has been used to improve the pharmacokinetics of therapeutic drugs. This nanocarrier system has many attractive characteristics for drug delivery, such as high drug loading capacity, narrow polydispersity, well-defined structure, easy chemical modification, superior physical, chemical stability and biocompatibility.

In some embodiments, the anti-Cif VHH, conjugate or fusion protein in conjunction with a therapeutic agent is formulated as a nanoparticle. Nanoparticle conjugates are known in the art and described, e.g., in Musacchio, et al., *Front Biosci.* (2011) 16:1388-412; Cuong, et al., *Curr Cancer Drug Targets.* (2011) 11(2):147-55; Jain, BMC Med. (2010) 8:83; Sunderland, et al., *Drug Development Research* (2006) 67(1):70-93; Gu, et al., *Nanotoday* (2007) 2(3):14-21; Alexis, et al., *ChemMedChem.* (2008) 3(12):1839-43; Fay, et al., *Immunotherapy.* (2011) 3(3):381-394; Minko, et al., *Methods Mol Biol.* (2010) 624:281-94; and PCT Publ. Nos. WO 2011/046842; WO 2010/040062; WO 2010/047765; and WO 2010/120385, the disclosures of which are hereby incorporated herein by reference in their entirety for all purposes. Known nanoparticle cores find use in encapsulating a therapeutic agent (e.g., a chemotherapeutic agent or an anti-neoplastic agent) for delivering to a lung cancer cell and/or to a prostate cancer cell. The anti-Cif VHH, conjugate or fusion protein can be integrated into, attached or conjugated directly to the nanoparticle core using methods known in the art. In some embodiments, the encapsulating nanoparticle is a cylindrical PRINT nanoparticle, e.g., as described in Gratton, et al., Proc Natl Acad Sci USA. (2008) 105(33):11613-8. The nanoparticle can be biodegradable or non-biodegradable, as appropriate or desired. Poly (lactic acid-co-glycolic acid) (PLGA), biodegradable poly(L lactic acid) (PLLA) and PEG-based hydrogels find use as a matrix material in particle drug delivery systems because they are biocompatible, bioabsorbable, and have already shown promise in medical applications.

Peptide nanoparticles and methods for their preparation are known in the art and described, e.g., in U.S. Patent Publication No. 2006/0251726, U.S. Patent Publication No. 2004/0126900, U.S. Patent Publication No. 2005/0112089, U.S. Patent Publication No. 2010/0172943, U.S. Patent Publication No. 2010/0055189, U.S. Patent Publication No. 2009/0306335, U.S. Patent Publication No. 2009/0156480, and U.S. Patent Publication No. 2008/0213377, each of which is hereby incorporated herein by reference in its entirety for all purposes. Further nanoparticle formulations that find use are described, e.g., in Emerich and Thanos, *Curr Opin Mol Ther* (2008) 10(2):132-9; Kogan, et al., *Nanomedicine* (2007) 2(3):287-306; Zhang, et al., *Bioconjug Chem* (2008) 19(1):145-152; Scarberry, et al., *J Am Chem Soc* (2008) 130(31):10258-10262; Fraysse-Ailhas, et al., *Eur Cells Materials* (2007) 14(Suppl. 3):115; Corrias F, Lai F., *Recent Pat Drug Deliv Formul.* 2011 Aug. 12, PMID:21834772; Wang, et al., *Biomaterials.* (2011) 32(32): 8281-90; and Kaur, et al., *Artif Cells Blood Substit Immobil Biotechnol.* 2011 Aug. 2., PMID:21806501.

3. Methods a. Methods of Making

Anti-Cif VHH can be derived from any immunoglobulin naturally devoid of light chains, such that the antigen-binding capacity and specificity is located exclusively in the heavy chain variable domain.

In certain embodiments an anti-Cif single-domain antibody can be obtained by immunization of dromedaries, camels, llamas, alpacas or sharks with the desired antigen and subsequent isolation of the mRNA coding for heavy-chain antibodies. By reverse transcription and polymerase chain reaction, a gene library of single-domain antibodies containing several million clones is produced. Screening techniques like phage display and ribosome display help to identify the clones binding the antigen (e.g. Cif). See, e.g., WO94/04678.

In one embodiment, a camelid is immunized with Cif to create a VHH library. VHH libraries from non-immunized camelids can also be screened. A VHH phage library can be built, as described herein or as known in the art. VHH phage libraries from immunized and non-immunized camelids are described, e.g., in Sabir, et al., C R Biol. (2014) 337(4):244-9; Nakayama, et al., *Monoclon Antib Immunodiagn Immunother.* (2016) 35(4):231-4; Yan, et al., *J Transl Med.* (2014) Dec. 10; 12:343; Klooster, et al., *Methods Mol Biol.* (2012) 911:241-53; Comor, et al., *Microb Cell Fact.* (2017) 16(1): 13; Jiang, et al., *Plant J.* (2013) 76(4):709-17 and Koh, et al., *J Biol Chem.* (2010) 285(25):19116-24. In some embodiments, anti-Cif VHH molecules are obtained from non-immunized libraries of camelid VHH sequences, for example by screening such a library against the antigen or at least one part, fragment, antigenic determinant or epitope thereof using one or more screening techniques known. Such libraries and techniques are for example described in WO99/37681, WO 01/90190, WO 03/025020 and WO 03/035694. Alternatively, synthetic or semi-synthetic libraries derived from non-immune VHH libraries may be used, such as VHH libraries obtained from naive VHH libraries by techniques such as random mutagenesis and/or CDR shuffling, as for example described in WO 00/43507.

Another technique useful for obtaining anti-Cif VHH involves suitably immunizing a transgenic mammal that is capable of expressing heavy chain antibodies (i.e. so as to raise an immune response and/or heavy chain antibodies directed against), obtaining a suitable sample from the transgenic mammal (such as a blood sample, or sample of B-cells), and then generating VHH sequences directed against starting from the sample, using any suitable technique known. For example, for this purpose, the heavy chain antibody-expressing mice and the further methods and techniques described in WO 02/085945 and in WO 04/049794 can be used.

In some embodiments, anti-Cif VHHs may be prepared by a method which does not require the donor previously to have been immunized with the target antigen. In some embodiments, the method comprises the use of a non-immunized library as described in EP1934611 A2. Such naïve or non-immunized libraries usually contain only antibodies with low affinity to the desired antigen. Accordingly affinity maturation by, for example, random mutagenesis may be utilized as an additional step. In one embodiment, the framework regions of the anti-Cif VHH domains may conveniently be derived from a non-immunized library of VHH domains. This allows the natural variability in these sequence segments to be reflected in the expression library. Such methods are well known in the art and described for instance in EP1934611 A2. In certain embodiments, the anti-Cif VHH are constructed with an amino acid sequence that corresponds to the amino acid sequence of a naturally occurring VHH domain, but that has been "humanized," as explained in EP1934611 A2. Humanization is generally not problematic because of the homology between camelid VHH and human VH fragments.

Other suitable ways and techniques for obtaining the VHH and/or nucleic acids encoding the same, starting from naturally occurring VHH sequences, will be clear to the skilled person, and may for example comprise combining one or more parts of one or more naturally occurring VH sequences (such as one or more FR sequences and/or CDR sequences), one or more parts of one or more naturally occurring VHH sequences (such as one or more FR sequences or CDR sequences), and/or one or more synthetic or semi-synthetic sequences, in a suitable manner, so as to provide a VHH or a nucleotide sequence or nucleic acid encoding the same.

The anti-Cif VHH can be generated in any manner known, which will be clear to the skilled person. Generally, this will involve at least one step of selecting anti-Cif VHH which bind to Cif, and in certain embodiments, a further step of selecting anti-Cif VHH capable of inhibiting Cif epoxide hydrolase activity. The first selection step can be performed in any manner known for selecting VHH or antibodies against a desired antigen, such as the techniques reviewed by Hoogenboom, *Nature Biotechnology*, 23, 9, 1105-1116 (2005), the so-called SLAM technology (as for example described in EP 0 542 810). The subsequent step(s) can generally be performed using any suitable in vitro, cell-based or in vivo assay (depending on the specific growth factor or antagonist thereto or material of an implant) and suitable assays will be clear to the skilled person based on the disclosure herein.

Typically in selections starting with an immune library the number of phages is reduced from $10^7$ to $10^4$; whereas in selections starting with a non-immunized library the number of phages is reduced from about $10^9$ to $10^4$. The selection is based on binding of the phage, (or of a yeast in a yeast display) to the antigen of choice. In the subsequent steps, consisting of DNA finger printing of the selected VHH genes, production in a production system, e.g., *E. coli*, and a lower eukaryote to evaluate the folding properties of the selected VHH in vivo, the number of positive phages is generally reduced from $10^4$ to $10^2$. The screening on in vivo folding properties of the selected VHHs selects for their functionality in and outside cells. It has been found that there is a strong correlation between correct folding in vivo and the refolding of VHHs in vitro. After this screening typically 20-50 VHHs remain suitable candidates and from these candidate VHHs the nucleotide sequences are determined, which also provide the amino acid sequences. The positive anti-Cif VHHs are then tested for desired property, including affinity and/or specificity for Cif and/or the ability to inhibit the epoxide hydrolase enzymatic activity of Cif. One applicable method for selection of anti-Cif VHH from libraries involves phage display technology, as described in EP1934611 A2.

Once selected, anti-Cif VHHs can be produced synthetically or recombinantly in host cells. In some embodiments, polynucleotides encoding anti-Cif VHHs are recombinantly expressed in host cells. In some embodiments, the host cell is a eukaryotic cell, e.g., a mammalian cell, a human cell, a yeast cell, a plant cell, an insect cell or an algal cell. In some embodiments, the host cell is a prokaryotic cell, e.g., a bacterial cell, e.g., an *E. coli* cell. In some embodiments, the host cell is a mammalian or human lymphoid cell or B cell. Methods for producing VHHs using B cells or cell lines are well known in the art. Production of VHH in filamentous fungi is described by Joosten et al., *J Biotechnol* 120:347-359 (2005). Methods for producing VHHs in *Saccharomyces cerevisiae* is described by Frenken et al. (2000) *J Biotechnol* 78:11-21. Additionally, VHH production in yeast expression host *Pichia pastoris* is described by Rahbarizadeh et al. (2006) *J Mol Immunol* 43:426-435. Polynucleotides encoding the anti-Cif VHH can be codon optimized or biased for improved recombinant expression in the desired host cell.

In some embodiments, the anti-VHH molecule comprises an N-linked glycosylation site. An advantage thereof is that this causes an increase in the production levels in yeast. Another advantage is that glycosylation sites can be advantageously used to chemically cross link, e.g., with carbohydrates or can be used as an anchor for the anti-Cif VHH in a dense polymer network as observed in hydrogels. In one embodiment, the anti-Cif VHH comprises a glycosyl group attached at one of the VHH's short loops present at the opposite site of the antigen binding domain of the VHH. An advantage of the presence of a glycosyl group is that this results in a slower release of the VHH when it is incorporated in a hydrogel.

b. Methods of Diagnosis

In view of the creation of anti-Cif VHH that bind Cif, in certain embodiments the anti-Cif VHH described herein can be used for the detection and/or quantitation of Cif in a sample, respectively in vivo, or in vitro. In certain embodiments such detection can have utility in a diagnostic context.

In some embodiments, the diagnostic or Cif detection methods involve contacting an anti-Cif VHH to a biological sample and detecting binding of the anti-Cif VHH to Cif Detection of the anti-Cif VHH bound to Cif in biological samples may occur with any method known in the art, including, but not limited to immunofluorescence microscopy, immunocytochemistry, immunohistochemistry, ELISA, FACS analysis, immunoprecipitation, micro-positron emission tomography, and the like.

For example, a biological sample may be stained with a labeled anti-Cif VHH, as described herein, in order to visualize, and/or detect, and/or quantify Cif in the specimen. The detection method may involve quantification of the anti-Cif VHH bound to Cif. Antibody/protein detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody and/or multimeric protein is radiolabeled, for example with Fluorine, and subsequently detected utilizing micro-positron emission tomography analysis. In certain embodiments the antibody and/or multimeric protein is labeled with a chromophore or fluorophore and detected using microscopy and/or immunocytochemistry.

In certain embodiments an anti-Cif VHH can be used to detect and/or quantify and/or visualize Cif, as correlated with *Pseudomonas* infection, in vivo. For example, the anti-Cif VHH can be labeled, with a radio-opaque label, an MRI label, a PET label, administered to a subject. The label can then be detected, localized, and visualized by x-ray or CAT scan, by MRI, or by PET scanning.

Accordingly in certain embodiments, methods of detecting Cif are provided where the methods involve contacting an anti-Cif VHH described herein with a test sample to form a mixture; incubating the mixture under conditions suitable for the formation of a complex between the anti-Cif VHH and Cif, if any, which is present in the sample, and detecting the presence, if any, and/or quantifying, if present, the complex formed between the anti-Cif VHH and Cif.

In certain embodiments, the anti-Cif VHH is immobilized on a particle or solid surface, and the binding of anti-Cif VHH to Cif immobilizes the Cif. The bound Cif can then be contacted with a "first" antibody that binds to the Cif and/or to multimeric anti-Cif VHH/Cif complex and detecting/ quantifying binding of that antibody. In certain embodiments a detectable label is attached to the "first" antibody and the detectable label is assayed to indicate the presence and/or quantity of Cif. In certain embodiments a "second" antibody is provided that binds to the first antibody where the second antibody is attached to a detectable label and this detectable label is assayed to indicate the presence and/or quantity of Cif.

Similarly, in certain embodiments, methods of detecting a Cif are provided where the methods involve contacting an anti-Cif VHH described herein with a test sample to form a mixture; incubating the mixture under conditions suitable for the formation of a complex between the anti-Cif VHH and Cif, if any, that are present in the sample, and detecting and/or quantifying the presence, if any, of the anti-Cif VHH.

In certain embodiments, a sandwich immunoassay is employed. In such embodiments, the anti-Cif VHH can be used as a capture antibody and is immobilized on a particle or solid surface, and the binding of the anti-Cif VHH to Cif immobilizes the bound Cif. The bound Cif can then be contacted with a "first" detection antibody that binds to the Cif and/or to anti-Cif VHH/Cif complex and detecting/ quantifying binding of that antibody. In certain embodiments a detectable label is attached to the "first" antibody and the detectable label is assayed to indicate the presence and/or quantity of Cif. In certain embodiments a "second" antibody is provided that binds to the first antibody where the second antibody is attached to a detectable label and this detectable label is assayed to indicate the presence and/or quantity of Cif. Alternatively, the "first" antibody can be used as a capture antibody, and the anti-Cif VHH can be used as a detection antibody.

Essentially any biological sample can be assayed for the presence and/or amount of Cif, e.g., as correlated with a *Pseudomonas* infection. Suitable samples include, but are not limited to saliva, sputum, bronchoalveolar lavage fluid (BALF), cheek swab, mucus, blood, sweat, tears, serum, plasma, urine, skin, cerebral spinal fluid (CSF), lymph, Eustachian tube fluid, bone marrow or feces, and the like. Generally, the sample is from a subject suspected of suffering from a *Pseudomonas* infection, particularly a *Pseudomonas aeruginosa* infection.

One of skill in the art will recognize that these samples and detecting methods are illustrative and not limiting. Using the teaching provided herein, numerous assays for Cif will be available to one of skill in the art.

c. Methods of Treatment

In certain embodiments, the anti-Cif VHH and/or Cif inhibitor compounds re utilized in various therapeutic contexts. Thus, for example, in certain embodiments, the anti-Cif VHH can be used in methods of reducing, inhibiting, mitigating and/or reversing one or more symptoms associated with or caused by a *Pseudomonas* infection, particularly a *Pseudomonas aeruginosa* infection. Typically, treatment involves administering to the subject an effective amount (e.g., an amount to reduce, inhibit, mitigate and/or reverse one or more symptoms) of one or more anti-Cif VHH molecules and/or Cif inhibitor compounds, or conjugates, or fusion proteins, or functional variants thereof, or nanoparticles/liposomes comprising the anti-Cif VHH molecules and/or Cif inhibitor compounds, or conjugates, or fusion proteins, as described herein. In some embodiments, the anti-Cif VHH molecule and/or Cif inhibitor is administered via a route selected from the group consisting of intrapulmonary, inhalational, intravenous, intramuscular, subcutaneous, intradermal, transcutaneous, topical, intrathecal, intralesional, transmucosal, intra-arterial, intraperitoneal, intraventricular and intracranial.

Accordingly, pharmaceutical compositions are provided containing one or a combination of anti-Cif VHH and/or Cif inhibitor compound, described herein, formulated together with a pharmaceutically acceptable carrier (e.g., excipient). In certain embodiments, a pharmaceutical composition comprising one or more anti-Cif VHH and/or Cif inhibitor compound is administered to a mammal in need thereof (e.g., an animal suffering a *Pseudomonas* infection, particularly a *Pseudomonas aeruginosa* infection).

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the anti-Cif VHH and/or Cif inhibitor compound may be coated in a material to protect the compound from the action of acids and other natural conditions that may inactivate the compound.

In certain embodiments the anti-Cif VHH and/or Cif inhibitor compound is provided in its native form, or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the anti-Cif VHH and/or Cif inhibitor compound can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

A "pharmaceutically acceptable salt" refers to a salt that retains the desired biological activity of the parent compound and does not impart any undesired toxicological effects (see e.g., Berge et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Methods of formulating such derivatives are known to those of skill in the art. For example, the disulfide salts of a number of delivery agents are described in PCT Publication WO 2000/059863 and are well known to those of skill in the art. For example, acid salts of anti-Cif VHH and/or Cif inhibitor compounds can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain acid addition salts of the anti-Cif VHH and/or Cif inhibitor compounds described herein include halide salts, such as may be prepared using hydrochloric or hydrobromic acids. Conversely, preparation of basic salts of the anti-Cif VHH and/or Cif inhibitor compounds described herein are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH lower than the pKa of the drug (e.g., anti-Cif VHH). Similarly, for the preparation of salt forms of acidic drugs, the pKa of the counterion is preferably at least about 2 pH higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

In certain embodiments, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments preparation of esters typically involves functionalization of hydroxyl and/or carboxyl groups that are present within the molecular structure of the anti-Cif VHH and/or Cif inhibitor compounds. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the anti-Cif VHH and/or Cif inhibitor compounds identified herein are useful for parenteral, oral, nasal (or otherwise inhaled), rectal, or transdermal administration. In certain embodiments the anti-Cif VHH and/or Cif inhibitor compounds are formulated for injection (e.g., for intravenous injection, intra-arterial injection, for intramuscular injection, for subdural injection, for subcutaneous injection, etc.). In certain embodiments the anti-Cif VHH and/or Cif inhibitor compounds are formulated for inhalation and in other embodiments, the anti-Cif VHH and/or Cif inhibitor compounds are formulated for oral administration. The compositions can be administered in a variety of unit dosage forms depending upon the method of administration. Suitable unit dosage forms, include, but are not limited to powders, tablets, pills, capsules, lozenges, suppositories, patches, sprays, injectables, implantable sustained-release formulations, lipid complexes, etc.

The active agents (e.g., anti-Cif VHH and/or Cif inhibitor compounds) described herein can also be combined with a pharmaceutically acceptable carrier (excipient) to form a pharmacological composition. In certain embodiments, pharmaceutically acceptable carriers include those approved by a regulatory agency of the Federal or a state government or listed in the U.S. Pharmacopeia or other generally recognized pharmacopeia for use in/on animals, and more particularly in/on humans. A "carrier" refers to, for example, a diluent, adjuvant, excipient, auxiliary agent or vehicle with which an active agent is administered.

Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alphastarch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., anti-Cif VHH and/or Cif inhibitor compounds) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

In some embodiments, the anti-Cif VHH and/or Cif inhibitor compounds are administered to the eyes. Administration of pharmacologically active agents to the eyes is well known, and considerable information is set forth in standard works, such as Zimmerman et al. (eds.), TEXTBOOK OF OCULAR PHARMACOLOGY, Lippincott Williams & Wilkins (1997); Jannus et al., (eds.), CLINICAL OCULAR PHARMACOLOGY, Butterworth-Heinemann (4th Ed., 2001), and Mauger and Craig, HAVENER'S OCULAR PHARMACOLOGY, Mosby-Year Book (6th Ed., 1994), Grosvenor, PRIMARY CARE OPTOMETRY, Butterworth-Heinemann, (4th Ed., 2001), Duvall and Kerschner, OPHTHALMIC MEDICATIONS AND PHARMACOLOGY, SLACK Inc., Thorofare, N.J. (1998), and Fechner and Teichmann, OCULAR THERAPEUTICS: PHARMACOLOGY AND CLINICAL APPLICATION, SLACK Inc., Thorofare, N.J. (1997). These well-known techniques can be readily applied to prepare and administer agents that increase the compliance of TM tissue to persons in need thereof.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

For preparing pharmaceutical compositions, pharmaceutically acceptable carriers can be either solid or liquid. The carriers may also act, for example, as diluents, binders, or preservatives.

Liquid form preparations include solutions, suspensions, and emulsions, for example, water or water/propylene glycol solutions. Other typical forms for administration of the agents, or combinations thereof are liquid paraffin, polyvinyl alcohol, povidine, carbomers, hypromellose, hydroxyethylcellulose, hydroxypropylcellulose, and carboxymethylcellulose.

Formulations for intravitreous injection are also known in the art. Intravitreal injection is typically performed in the outpatient setting using topical anesthesia and a small-bore needle (e.g., 27 or 30 gauge) to deliver the medication into the vitreous cavity of the eye via the pars plana portion of the globe. Typically, the agents, or combinations thereof are administered as a sterile, preservative-free aqueous solution, which may optionally contain sodium chloride, monobasic sodium phosphate monohydrate, dibasic sodium phosphate heptahydrate, hydrochloric acid, and/or sodium hydroxide and other agents to adjust the viscosity and pH.

In certain therapeutic applications, the compositions are administered, e.g., parenterally (e.g., intrapulmonary, intranasal, intramuscular, intravenous), orally, intraperitoneally, topically (including to the eyes) to a patient suffering from, or a at risk for a *Pseudomonas* infection in an amount sufficient to prevent and/or slow, and/or cure and/or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations to effectively treat (ameliorate one or more symptoms in) the patient.

The pharmaceutical compositions comprising one or more anti-Cif VHH and/or Cif inhibitor compounds can be administered alone or in combination therapy, i.e., combined with other agents (e.g., one or more antibiotics). For example, the combination therapy can include a composition described herein with at least one or more additional therapeutic agents, such as various agents shown in Table 7.

In certain embodiments it is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the active compound (the anti-Cif VHH and/or Cif inhibitor compounds) and the particular therapeutic effect to be achieved, and (b) the limitations inherent in the art of compounding such an active compound for the treatment of sensitivity in individuals.

The amount of active ingredient that can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

In certain embodiments when the anti-Cif VHH and/or Cif inhibitor compounds described herein are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the anti-Cif VHH and/or Cif inhibitor compounds employed in the pharmaceutical composition at levels lower than that required in order to achieve the desired therapeutic effect and gradually increase the dosage until the desired effect is achieved. In general, a suitable daily dose of a composition will be that amount of the compound which is the lowest dose effective to produce a therapeutic effect. Such an effective dose will generally depend upon the factors described above.

Non-limiting examples of suitable dosage ranges and regiments include 2-50 mg/kg (body weight of the subject) administered once a week, or twice a week or once every three days, or once every two weeks, and 1-100 mg/kg administered once a week, or twice a week or once every three days, or once every two weeks. In various embodiments, an anti-Cif VHH and/or Cif inhibitor compounds is administered at a dosage of 3.2 mg/kg, 6 mg/kg, 10 mg/kg, 15 mg/kg, 20 mg/kg, 25 mg/kg, 30 mg/kg, 35 mg/kg or 40 mg/kg at a timing of once a week, or twice a week or once every three days, or once every two weeks. Additional dosage ranges include: 1-1000 mg/kg, 1-500 mg/kg, 1-400 mg/kg, 1-300 mg/kg and 1-200 mg/kg. Suitable dosage schedules include once daily, twice daily, three times daily, four times daily, five times daily, once every three days, once every five days, once every seven days (i.e., once a week), once every 10 days, once every 14 days (i.e., once every two weeks), once every 21 days (i.e., once every three weeks), once every 28 days (i.e., once every four weeks) and once a month.

Use of the anti-Cif VHH and/or Cif inhibitor compounds in combination with an additional therapeutic agent (e.g., an antibiotic or Cif inhibitor compound) can lead to an additive or synergistic effect for treatment and/or prophylaxis of a *Pseudomonas* infection or recurrence thereof. Accordingly, for combination therapy, suboptimal dosages of the anti-Cif VHH and/or Cif inhibitor compounds, the second therapeutic agent, or both, can be used to achieve a desired therapeutic. For example, when used in combination with another therapeutic agent, in various embodiments the anti-Cif VHH and/or Cif inhibitor compounds described herein may be administered at a dosage that is 90%, or 80%, or 70% or 60% or 50% of the dosage used when the anti-Cif VHH and/or Cif inhibitor compounds are administered alone.

As desired, the effective daily dose of a therapeutic composition may be administered as two, three, four, five, six or more sub-doses administered separately at appropriate intervals throughout the day, optionally, in unit dosage forms. While it is possible for the anti-Cif VHH to be administered alone, it is preferable to administer the compound as a pharmaceutical formulation (composition).

In certain embodiments therapeutic compositions comprising the anti-Cif VHH and/or Cif inhibitor compounds can be administered with medical devices known in the art. For example, in certain embodiments, the anti-Cif VHH and/or Cif inhibitor compounds described herein can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules for delivery of an active agent (e.g., an anti-Cif VHH and/or Cif inhibitor compounds) those described in U.S. Pat. No. 4,487,603, which discloses an implantable micro-infusion pump for dispensing medication at a controlled rate, those described in U.S. Pat. No. 4,486,194, which discloses a therapeutic device for administering medications through the skin; those disclosed in U.S. Pat. No. 4,447,233, which discloses a medication infusion pump for delivering medication at a precise infusion rate; those disclosed in U.S. Pat. No. 4,447,224, which discloses a variable flow implantable infusion apparatus for continuous drug delivery, those disclosed in U.S. Pat. No. 4,439,196, which discloses an osmotic drug delivery system having multi-chamber compartments; those disclosed in U.S. Pat. No. 4,475,196, which discloses an osmotic drug delivery system, and the like. Many other such implants, delivery systems, and modules are known to those skilled in the art.

In certain embodiments, the anti-Cif VHH and/or Cif inhibitor compounds can be formulated to ensure proper distribution in vivo. For example, the blood-brain barrier (BBB) excludes many highly hydrophilic compounds. In certain embodiments to ensure that the therapeutic compounds cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., Ranade (1989) *J. Clin. Pharmacol.* 29: 685). Exemplary targeting moieties include, but are not limited to folate or biotin (see, e.g., U.S. Pat. No. 5,416,016); mannosides (see, e.g., Umezawa et al., (1988) *Biochem. Biophys. Res. Commun.* 153:1038); antibodies (see, e.g., Bloeman et al. (1995) *FEBS Lett.* 357:140; M. Owais et al. (1995) *Antimicrob. Agents Chemother.* 39:180); surfactant protein A receptor (see, e.g., Briscoe et al. (1995) *Am. J. Physiol.* 1233:1234), different species of which may comprise the formulations.

d. Methods of Screening Cif Inhibitors

Further provided are methods of screening for inhibitors of Cif enzymatic activity. In some embodiments, the methods comprise:

a) providing a solid support coated with polyclonal antibodies raised against Cif and bound to Cif;

b) concurrently exposing the solid support to an anti-Cif VHH molecule, as described above and herein, and a candidate inhibitor of Cif;

c) identifying inhibitors of Cif that compete with or displace binding of the anti-VHH molecule to the Cif bound to the polyclonal antibodies coated on the solid support. In some embodiments, the screening method identifies a Cif inhibitor that inhibits Cif enzymatic or catalytic activity with a greater potency than the VHH molecule. In some embodiments, the anti-VHH molecule is attached to a detectable label, and detection of the label is used to measure displacement of unbound anti-VHH molecule by the Cif inhibitor. In some embodiments, the Cif inhibitor is attached to a detectable label, and detection of the label is used to measure binding of the Cif inhibitor to Cif immobilized on the solid support. In some embodiments, the anti-VHH molecule further comprises a detectable tag, and an antibody against the tag is used to measure displacement of the unbound anti-VHH molecule by the Cif inhibitor. In some embodiments, the candidate Cif inhibitor is a small organic compound.

Further provided are methods of screening for VHH molecules that are inhibitors of Cif enzymatic activity. In some embodiments, the methods comprise:

a) providing a solid support coated with polyclonal antibodies raised against Cif and bound to Cif;

b) concurrently exposing the solid support to a known small organic inhibitor of Cif enzymatic activity and a candidate anti-Cif VHH molecule;

c) identifying anti-Cif VHH that compete with or displace binding of the known small organic inhibitor of Cif enzymatic activity to the Cif bound to the polyclonal antibodies coated on the solid support. In some embodiments, the anti-VHH molecule is attached to a detectable label, and detection of the label is used to measure binding of the anti-Cif VHH to Cif immobilized on the solid support. In some embodiments, the screening method identifies an anti-Cif VHH that inhibits Cif enzymatic or catalytic activity with a greater potency than the Cif inhibitor. In some embodiments, the anti-VHH molecule further comprises a detectable tag, and an antibody against the tag is used to measure binding of the anti-Cif VHH to Cif immobilized on the solid support. In some embodiments, the Cif inhibitor is attached to a detectable label, and detection of the label is used to measure displacement of unbound Cif inhibitor by the anti-Cif VHH molecule. In some embodiments, the known small organic inhibitor is a compound listed in Table 7.

Further provided are methods of screening for inhibitors of enzymatic or catalytic activity of an enzyme. In some embodiments, the methods comprise:

a) providing a solid support coated with polyclonal antibodies raised against the enzyme and bound to the enzyme;

b) concurrently exposing the solid support to a VHH molecule that binds to and inhibits the enzymatic or catalytic activity of the enzyme and a candidate inhibitor of the enzyme;

c) identifying inhibitors of the enzyme that compete with or displace binding of the VHH molecule to the enzyme bound to the polyclonal antibodies coated on the solid support. In some embodiments, the VHH molecule is attached to a detectable label, and detection of the label is used to measure displacement of the VHH molecule by the enzyme inhibitor. In some embodiments, the VHH molecule further comprises a detectable tag, and an antibody against the tag is used to measure displacement of the VHH molecule by the enzyme inhibitor. In some embodiments, the candidate enzyme inhibitor is a small organic compound. In some embodiments, the candidate enzyme inhibitor inhibits enzymatic or catalytic activity with a greater potency than the VHH molecule.

In some embodiments of the screening methods, the solid support is a bead, a microwell plate, a chip or a microfluidics device. The screening methods can be performed using any known immunoassay format known in the art. In some embodiments, the screening methods are performed employing ELISA, solid phase radioimmunoassay (SPRIA), immunoprecipitation or surface plasmon resonance (SPR).

4. Kits

In certain embodiments, kits are provided, e.g., for the detection of Cif or for the treatment of a *Pseudomonas* infection, particularly a *Pseudomonas aeruginosa* infection. In certain embodiments the kits comprise a container containing one or more anti-Cif VHH, fusion proteins, or conjugates thereof, as described herein. In certain embodiments, the anti-Cif VHH is provided in a pharmaceutical formulation.

In certain embodiments, the kits additionally include a container containing a second therapeutic agent. In certain embodiments the second therapeutic agent comprises and antibiotic or a Cif inhibitor compound, as described above and herein.

In certain embodiments the kits include labeling and/or instructional materials disclosing means of use of the anti-Cif VHH and/or pharmaceutical formulations for the detection of Cif in a biological sample or for the treatment of a *Pseudomonas* infection. In certain embodiments the instructional materials include recommended concentrations, incubation conditions and detection techniques. In certain embodiments the instructional materials include recommended dosages, methods of dosing, and/or counter-indications for the therapeutic agent, and the like.

While the instructional materials in the various kits typically comprise written or printed materials they are not limited to such. Any medium capable of storing such instructions and communicating them to an end user is contemplated. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Nanobodies that Specifically Bind to Cystic Fibrosis Transmembrane Conductance Regulator (CFTR) Inhibitory Factor (Cif)

Materials and Methods

All chemicals were of analytical grade and were purchased either from Fisher Scientific Co. (Chicago, Ill.) or from Sigma-Aldrich Co (St. Louis. Mo.) unless otherwise stated. Helper phage M13KO7 and SfiI were purchased from New England Biolabs (Ipswich, Mass.). (Ipswich, Mass.). Mouse anti-M13 phage mAb-horseradish peroxidase (HRP) was purchased from GE Healthcare (Piscataway, N.J.). Chemically competent TOP10F' cells were obtained from Invitrogen (Carlsbad, Calif.). The plasmid purification kit, gel purification kit, PCR purification kit, and 6×His tag (SEQ ID NO: 90) purification resins were obtained from Qiagen (Valencia, Calif.). Electrocompetent ER2738 *E. coli* cells were purchased from Lucigen Corporation (Middleton, Wis.). B-PER lysis solution was purchased from Thermo Pierce Scientific (Rockford, Ill.). CIF protein and purified polyclonal anti-CIF antibody were generously provided by Dr. Dean Madden (Dartmouth Medical School).

Buffers.

All buffers and water solutions were prepared with ultrapure deionized water; phosphate-buffered saline (PBS, 10 mM, pH 7.5); wash buffer PBST (PBS containing 0.05% TWEEN 20); coating buffer (14 mM $Na_2CO_3$, 35 mM $NaHCO_3$, pH 9.8); blocking buffer (1% BSA in PBST); substrate buffer (0.1 M sodium citrate/acetate buffer, pH 5.5). Substrate solution contained 0.2 mL of 0.6% TMB (in dimethyl sulfoxide, DMSO w/v), 0.05 mL of 1% $H_2O_2$ in 12.5 mL of substrate buffer. Stop solution was 2M $H_2SO_4$.

General.

All reagents and solvents were purchased from commercial suppliers and were used without further purification. All reactions were performed in an inert atmosphere of dry nitrogen or argon. 1H NMR spectra were collected using a Varian 600 MHz or Bruker DRX-600 MHz spectrometer with chemical shifts reported relative to residual deuterated solvent peaks or a tetramethylsilane internal standard. Accurate masses were measured using an LTQ orbitrap hybrid mass spectrometer (HRMS). The purity of the compounds that were tested in the assay was determined by reverse phase HPLC-DAD and found to be >95% based on monitoring absorption at 254 nm. Reactions were monitored on TLC plates (silica gel matrix, fluorescent indicator, Sigma-Aldrich, 99569), and spots were either monitored under UV light (254 mm) or stained with phosphomolybdic acid. The same TLC system was used to test purity, and all final products showed a single spot on TLC with both phosphomolybdic acid and UV absorbance.

5'-(2,6-dichloro-4-propionamidophenoxy)-3-fluoro-2'-hydroxy-[1,1'-biphenyl]-4-carboxamide (18f)

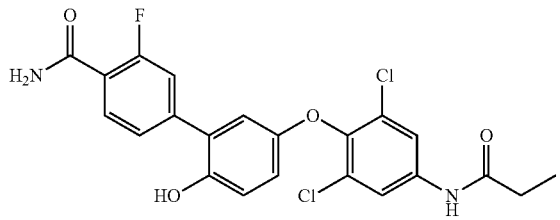 [SMILES: CCC(=O)Nc1cc(Cl)c(Oc2ccc(O)c(-c3ccc(C(N)=O)c(F)c3)c2)c(Cl)c1]

Compound 18f was synthesized by the method described previously (40) using 2-fluoro-4-(4,4,5,5-tetramethyl-1,3,2-dioxaborolan-2-yl) benzamide to give the desired product (8 mg, 10%) as an off-white powder; $^1$H NMR (600 MHz, DMSO-$d_6$) δ 10.22 (s, 1H), 9.63 (s, 1H), 7.83 (s, 2H), 7.69-7.65 (m, 2H), 7.62 (s, 1H), 7.42 (d, J=12.1 Hz, 1H), 7.38 (d, J=8.0 Hz, 1H), 6.91 (d, J=9.2 Hz, 1H), 6.81 (d, J=3.1 Hz, 1H), 6.66 (dd, J=8.9, 3.1 Hz, 1H), 2.35 (q, J=7.5 Hz, 2H), 1.09 (td, J=7.4, 1.2 Hz, 3H). $^{13}$C NMR (151 MHz, DMSO) δ 172.6, 165.1, 158.9 (d, $J_{CF}$=-249 Hz), 149.8, 149.6, 142.1, 141.5, 137.7, 130.0, 128.6, 126.2, 124.8, 121.9 (d, $J_{CCF}$=15 Hz), 119.2, 117.2, 116.4 (d, $J_{CCF}$=24 Hz), 115.9, 115.4, 29.6, 9.4. Purity (HPLC-UV): >99% (tR=9.99 min). HRMS (+) calcd for $C_{22}H_{18}C_{12}FN_2O_4$ (M-H)+463.0622. Found 463.0620.

5'-(4-amino-2,6-dichlorophenoxy)-2'-hydroxy-[1,1'-biphenyl]-4-carboxamide (18NH$_2$)

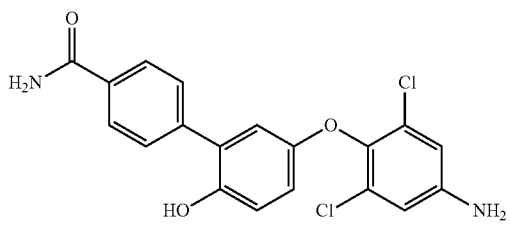 [SMILES: NC(=O)c1ccc(-c2cc(Oc3c(Cl)cc(N)cc3Cl)ccc2O)cc1]

Compound 18NH$_2$ was synthesized by the method described previously 40 using Suzuki-Miyaura coupling between 4-(4-amino-2,6-dichlorophenoxy)-2-iodophenol and (4-carbamoylphenyl) boronic acid to give the desired product (378 mg, 38%) as an off-white powder; $^1$H NMR (600 MHz, DMSO-d6) δ 9.38 (s, 1H), 7.95 (s, 1H), 7.88 (dd, J=8.4, 1.6 Hz, 2H), 7.60-7.48 (m, 2H), 7.33 (s, 1H), 6.88 (d, J=8.8 Hz, 1H), 6.69 (d, J=1.3 Hz, 3H), 6.62 (dd, J=8.8, 3.0 Hz, 1H), 5.60 (s, 2H). $^{13}$C NMR (151 MHz, DMSO) δ 167.7, 150.3, 149.4, 147.5, 140.9, 135.6, 132.6, 128.69, 128.68, 127.4, 127.3, 117.0, 115.7, 114.7, 113.4. Purity (HPLC-UV): >99% (tR=9.25 min). HRMS (+) calcd for $C_{19}H_{18}C_{12}N_2O_3$ (M-H)+389.0454. Found 389.0450.

Purity Assessment of the Inhibitors by HPLC-UV.

Purity determination of synthetic compounds was performed on an Agilent 1200 Series HPLC with a G1322A degasser, a G1311A Quatpump, and a G1315D Agilent detector. The Varian Pursuit5 C18 RP HPLC column (150 mm×2.0 mm, particle size 5 μm) was used. The UV absorption between 190 nm and 400 nm was monitored, and the purity was determined by the peak area at 254 nm. Gradients are described in Table 1. In addition, all final products showed a single spot on TLC (silica gel matrix, fluorescent indicator, Sigma-Aldrich, 99569) under UV light (254 mm) and >95% purity on $^1$H NMR.

TABLE 1

| HPLC solvent gradient for the purity determination | | | |
|---|---|---|---|
| Time | Aqueous phase$^a$ | Organic phase$^b$ | Flow rate (mL/min) |
| 0.00 | 90 | 10 | 0.3 |
| 15.00 | 0 | 100 | 0.6 |
| 25.00 | 0 | 100 | 0.6 |
| 25.01 | 90 | 10 | 0.3 |
| 35.00 | 90 | 10 | 0.3 |

$^a$Milli-Q water 99.9, formic acid 0.1, volume %,
$^b$Acetonitrile 99.9, formic acid 0.1, volume %.

Immunization and Library Construction.

An alpaca was immunized with CIF protein (200 μg per injection) in complete Freud's adjuvant and boosted four times with the same dose in incomplete Freund's adjuvant. Blood was drawn every two weeks to assess the blood titer. A VHH phage display library was built as previously described (41). The mRNA was extracted using Leuko-LOCK™ Total RNA Isolation System (Thermofisher) and transcribed to cDNA with SuperScript III RT System (Invitrogen). The cDNA was then used as template for PCR amplification of the VHH genes using the forward primers, VH1, VH3, VH4, VHH1 Back, VHH 6 Back, F and F2D and the reverse primer JH (Table 2) (42). The amplified DNA was digested with SfiI and ligated into pComb3X (gift from Dr. Carlos Barbas, The Scripps Research Institute, La Jolla, USA). The resulting vector was electroporated in electro-competent cells E. coli ER2738. The cells were cultured and the phage library displaying VHH repertoire was created by superinfection with helper phage M13KO7 (Pharmacia Biotech, Uppsala, Sweden). Library diversity was evaluated through sequencing of 20 random clones.

TABLE 2

Primers sequences for library construction

| Primer name | Sequence in 5' -> 3' |
|---|---|
| Forward | |
| VHH1BACK | GT TAT TACT CGC GGCCCAGGCGGCC ATG GCC CAG GTS MAR CTG CAG SAG TCW GG (SEQ ID NO: 91) |
| VHH6BACK | T GTT ATT ATC TGC GGCCCAGGCGGC C ATG GCC GAT GTG CAG CTG CAG GCG TCT GGR GGA GG (SEQ ID NO: 92) |
| VH1 | CAT GCC ATG ACT CGC GGCCCAGGCGGC C ATG GCC CAG GTG CAG CTG GTG CAG TCT GG (SEQ ID NO: 93) |
| VH3 | CAT GCC ATG ACT CGC GGCCCAGGCGGCC ATG GCC GAG GTG CAG CTG GTG GAG TCT GG (SEQ ID NO: 94) |
| VH4 | CAT GCC ATG ACT CGC GGCCCAGGCGGCC ATG GCC CAG GTG CAG CTG CAG GAG TCG GG (SEQ ID NO: 95) |
| F2-D | CAT GACTGTGGCCCAGGCGGC CATGCAGGTGCAGCTCGTGGASWCHGGNGGAGGMTTG GT (SEQ ID NO: 96) |
| F1 | CATGCCATGACTGTGGCCCAGGCGGCCCAGKTGCAGC TCGTGGAGTC (SEQ ID NO: 97) |
| Reverse | |
| JH | CCA CGA TTC TGGCCGGCCTGGCCT GAG GAG ACR GTG ACC TGG GTC C (SEQ ID NO: 98) |

Restriction site SfiI is underlined

Phage Library Panning for CIF Selective Clones.

Panning procedure was performed based on protocols described by Barbas (43). Panning was performed by two methods, described in detail below.

Method 1.

Library was panned against Cif initially bound to the purified polyclonal anti-Cif antibody. Two wells of a microtiter plate were coated with pAb (0.3 µg/well) in coating buffer at room temperature (RT) for 1 h. Then these two plus additional 4 wells were blocked/coated with 200 µL of 1% BSA in PBS for at least 2 h at RT. One of the wells coated with pAb was then incubated with decreasing amount of Cif at each round of panning. An aliquot of the phage library (100 µL) was added to the well coated with pAb only, incubated for 1 h at RT (removal of non-specific binders to pAb). All unbound phage was transferred to the BSA only coated well, 25 µL per well (removal of nonspecific BSA bounders). After another 1 h of incubation, unbound phages were transferred to the well coated with pAb/Cif and incubated for 1 h at RT. After washing with PBST, this well was eluted with 100 µL of trypsin at 10 mg/mL in PBS at 37° C. for 30 min.

Method 2.

Library was panned against Cif directly bound to the plate. The procedure is similar to the method 1 but does not involve pAb steps. Details on panning conditions are provided in Table 3. The eluent was collected and amplified with addition of the M13KO7 helper phage ($1\times10^{12}$ cfu/mL). The titer was assessed for the output library after panning and for the input library after amplification. ER2738 E. coli were infected with the eluted or amplified phages and titered on LB-carbenicillin (CA) agar plates. 100 µL of the amplified phages was employed again in the next round of panning. For the second, third, and fourth rounds, the same procedure was used, except the concentration of Cif was gradually decreased. After the final round of panning, individual clones were screened to identify positive clones by performing a phage ELISA.

TABLE 3

Summary of Panning Conditions

| Round of panning | pAb anti-CIF conc. µg/mL | CIF conc. µg/mL | number of washes | Trypsin elution conc mg/mL | input | output |
|---|---|---|---|---|---|---|
| Approach 1. | | | | | | |
| $1^{st}$ | 2.8 | 10 | 5 | 10 | $8 \times 10^{11}$ | $6.5 \times 10^{7}$ |
| $2^{nd}$ | 2.8 | 5 | 10 | 10 | $10^{13}$ | $9 \times 10^{8}$ |
| $3^{rd}$ | 2.8 | 1 | 10 | 10 | $8 \times 10^{12}$ | $4 \times 10^{8}$ |
| $4^{th}$ | 2.8 | 1 | 10 | 10 | $3 \times 10^{12}$ | $1.5 \times 10^{8}$ |
| Approach 2. | | | | | | |
| $1^{st}$ | No | 10 | 5 | 10 | $8 \times 10^{11}$ | $3.7 \times 10^{7}$ |
| $2^{nd}$ | No | 5 | 10 | 10 | $3.8 \times 10^{12}$ | $8 \times 10^{7}$ |
| $3^{rd}$ | No | 1 | 10 | 10 | $2 \times 10^{13}$ | $4 \times 10^{6}$ |
| $4^{th}$ | No | 1 | 10 | 10 | $10^{12}$ | $5 \times 10^{7}$ |

Expression and Purification of CIF VHHs.

From the agar plate containing the fourth elution output titer, 24 individual clones from Method 1 and Method 2 were randomly selected and grown individually in cultures overnight. Cultures for each clone were spun down at 3000 g for 10 min. For the protein extraction, the bacterial protein extraction reagent kit (BPER) was employed and the obtained protein was further characterized by ELISA. For positive clones the plasmid was extracted from cultures with Qiagen Mini Prep kit and the sequences were submitted to the UC Davis DNA Sequencing Facility. The plasmids pComb3X, containing positive VHH clones, were transformed by heat shock into Top 10F' cells. The expression and purification of VHHs was the same as previously described (43-45).

A 1-mL aliquot of overnight culture was diluted in 100 mL of Super Broth with 50 µg/mL carbenicillin. After OD reached 0.5-1, the culture was induced with 1 mM IPTG and incubated in a shaker at 37° C. overnight. The culture was centrifuged, and the cell pellet was lysed with B-PER lysis buffer (4 mL/g pellet) containing protease inhibitors at ambient temperature for 10 min. The cell lysate supernatants were collected by centrifugation at 13000×g for 10 min, followed by purifying on a 1-mL Ni-NTA resin column. The column was equilibrated and washed with 40 mM imidazole (dissolved in 10 mM PBS, pH 7.4). The VHH was eluted with 150 mM imidazole, and the purified VHH was stored at −20° C. after desalting on Zeba desalting column (Thermofisher).

High Yield Expression of Inhibitory VHHs.

For expression, the VHH genes were cloned in the pET 28a(+), flanked by the coding sequences of the ompA signal peptide at the 5' end, and the 6×His tag (SEQ ID NO: 90) and the HA epitope coding sequences (vector generously provided by Dr. Gonzalez-Sapienza, UDELAR, Uruguay). The vector was transformed into BL21(DE3) E. coli, individual clones were grown in LB-kanamicyn (40 µg/mL) plates and antibody expression was induced with 10 µM IPTG during 4 hours at 37° C. Cells were pelleted and the periplasmic proteins were extracted by osmotic shock as described previously (46). Antibody purification was performed on Ni-NTA columns in the FPLC purification system (Bio-Rad) according to the manufacturer's instructions.

Fluorescent-Based Cif Inhibitory Assay.

Figure 1:
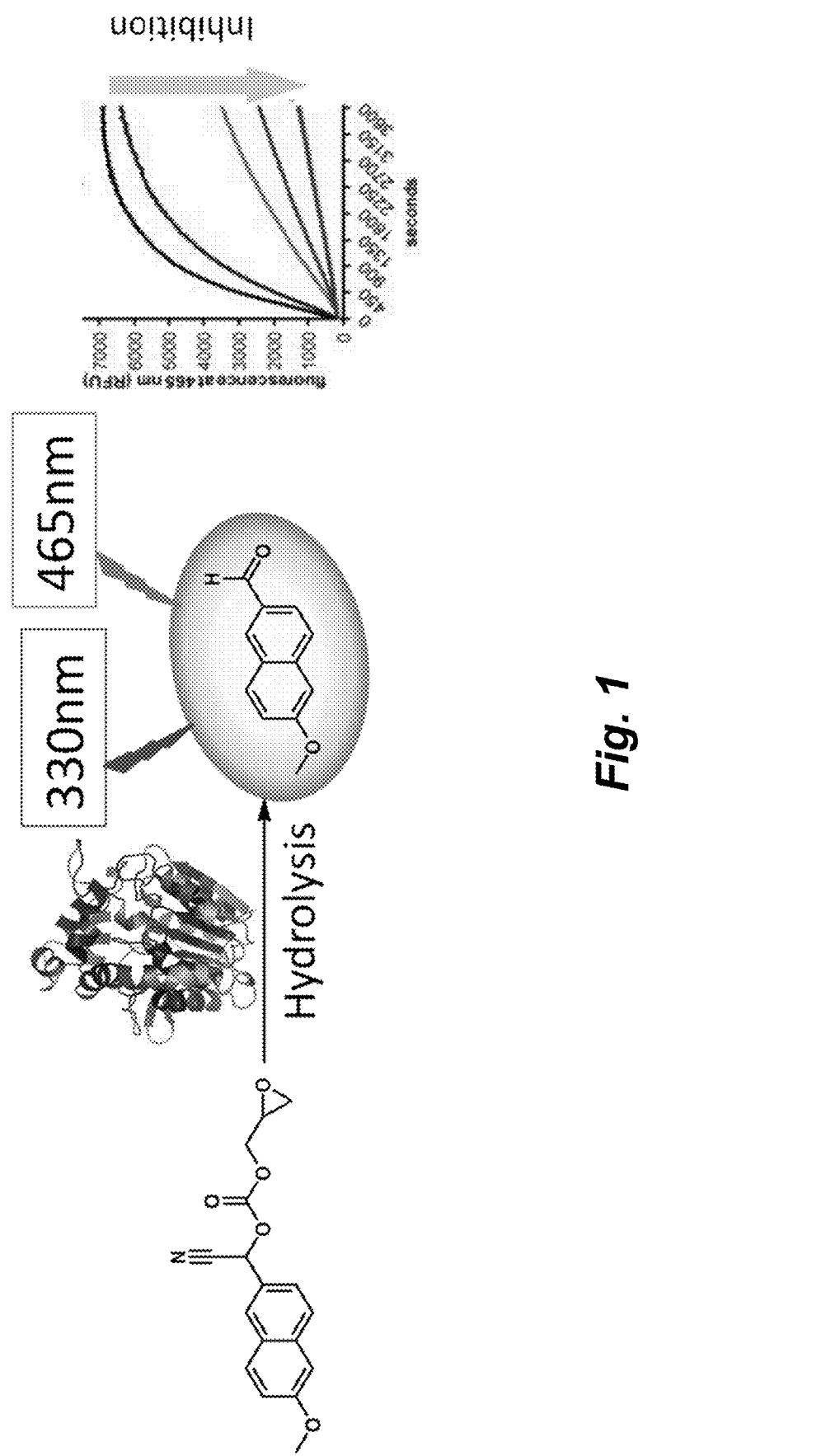
FIG. 1 illustrates a schematic of the fluorescent assay described herein. Cif hydrolyzes a reporter releasing a fluorescent probe.

Activity of enzyme was measured using a sensitive fluorescent-based assay similar to the method previously described for other EHs (29,30). Cyano(6-methoxynaphthalen-2-yl)methyl glycidyl carbonate (CMNGC) was used as a fluorescent reporter substrate. Recombinant Cif (0.6 µM) was incubated with VHHs for 5 min in sodium phosphate buffer (20 mM, pH 7.0) containing 50 mM NaCl and 0.1 mg/mL of BSA at 37° C. prior to substrate introduction ([S]=25 µM). A schematic of the assay is depicted in FIG. 1.

Activity was measured by determining the appearance of the 6-methoxy-2-naphthaldehyde with an excitation wavelength of 330 nm and an emission wavelength of 465 nm for 10 min. Reported IC50 values are the average of triplicates with at least two data points above and at least two below the IC50. The fluorescent-based assay as performed here has a standard error between 10% and 20%, suggesting that differences of 2-fold or greater are significant. Control experiments without Cif (inhibitor/VHH and substrate) were used to evaluate the intrinsic fluorescence of inhibitors.

VHH-Based Assay.

The optimal concentration of the coating anti-Cif pAb was determined as a minimal amount of the pAb sufficient to saturate the surface of the well and was 0.3 µg/well. The optimal concentrations of Cif and VHHs for both types of assay were determined from a checkerboard titration.

1). Immunoassay.

A 96-well plate was coated with pAb at 3 µg/mL, 100 µL per well at RT for 1 h. The plate was blocked with 1% skimmed milk in PBST at RT for at least 2 h. Cif in PBS was loaded on the plate with increasing concentration and incubated for 1 h at RT. Following 5 times wash with PBST, VHH at 0.5 µg/mL in PBS, 100 µL per well (or 50 ng/well) was loaded. The plate was incubated for 1 h at RT and then washed 5 times with wash buffer. Mouse anti-HA-HRP conjugate was added at 100 µl/well in a 1:3000 dilution as instructed by manufacturer. The plate was incubated for 1 h at RT and washed 5 times. The plate was developed for 10 min with substrate solution added at 100 µl/well. The reaction was stopped by addition of 2M $H_2SO_4$ (50 µl/well) and absorbance was read at 450 nm. SigmaPlot 11.0 software was used for curve fitting and data analysis.

2). Competitive or Displacement Sandwich Assay.

A 96-well plate was coated with pAb at 3 µg/mL, 100 µL per well at RT for 1 h. The plate was blocked with 1% skimmed milk in PBST at RT for at least 2 h. Cif in PBS was loaded at 20 ng/mL, 100 µL/well and incubated for 1 h at RT. Following 5 times wash with PBST, a serial dilution of small molecule synthetic inhibitors in PBS containing 20% methanol at 50 µL/well was loaded, followed by 50 µL/well of VHH at 0.1 µg/mL (or 5 ng/well) in PBS and incubated for 1 h at RT. Mouse anti-HA-HRP conjugate was added at 100 µl/well in a 1:3000 dilution as instructed by manufacturer. The plate was incubated for 1 h at RT and washed 5 times. The plate was developed for 10 min with substrate solution added at 100 µl/well. The reaction was stopped by addition of 2M $H_2SO_4$ (50 µl/well) and absorbance was read at 450 nm. SigmaPlot 11.0 software was used for curve fitting and data analysis.

Surface Plasmon Resonance (SPR).

The interactions between Cif and inhibitors were analyzed by surface plasmon resonance using a BIAcore T100. The running buffer for immobilization was HBS-P (pH 7.4), which contains 10 mM HEPES, 150 mM NaCl, and 0.05% (v/v) TWEEN 20 surfactant. Cif was coupled to the surface of a CM5 sensor chip using standard amine-coupling chemistry with a 2 min injection at 25 µL/min flow of Cif (1.5 µg/mL) diluted in 10 mM sodium acetate (pH 4.5). Cif protein was immobilized at 100 RU. Remaining activated groups were blocked with a 7 min injection at 10 µL/min of 1 M ethanolamine HCl (pH 8.5). Binding assays were performed at a flow rate of 30 µL/min with a 400 s injection of VHHs followed by washing with buffer for 1000 s. Sodium phosphate buffer (20 mM pH 7.0) containing 50 mM NaCl and 0.05% (v/v) TWEEN 20 was used as a running buffer in the assay. Experimental data were analyzed using BIAevaluation 1.0 software (BIAcore).

Octet Bio-Layer Interferometry:

KD of Cif and their inhibitors was determined by Bio-Layer Interferometry using an Octet Red instrument (ForteBio). Recombinant Cif-His was prepared as described previously (20,29). Stocks of purified proteins were stored at 4° C. until used. Cif-His at ~1 µM in kinetics buffer (sodium phosphatebuffer (20 mM pH 7.0) containing 50 mM NaCl, 4% DMSO and 0.02% TRITON X-100 was loaded onto Ni-NTA biosensors and incubated with varying concentrations of small molecule in solution (39 nM-10 µM). All binding data were collected at 30° C. The experiments comprised five steps: (1) baseline acquisition (60 s); (2) Cif loading onto sensor (1800 s); (3) second baseline acquisition (120 s); (4) association of small molecule (120 s); and (5) dissociation of small molecule (120 s). Baseline and dissociation steps were carried out in buffer only. The KD was calculated based on steady state analysis.

Results

Selection of Anti-CIF VHHs.

Two approaches of panning for Cif-selective nanobodies have been used. Approach 1 employed polyclonal anti-Cif antibody to present Cif to the phages library of nanobodies. Cif protein is thought to preserve better its 3D configuration when bound to the coating polyclonal antibody. On the other hand approach 2 involved direct coating of the plate with Cif-protein presumably resulting in deformed and partially denatured protein. Panning in both approaches was performed with Cif concentration decreasing in each round thus promoting selection of clones with higher affinity (Table 3).

Figure 2A:
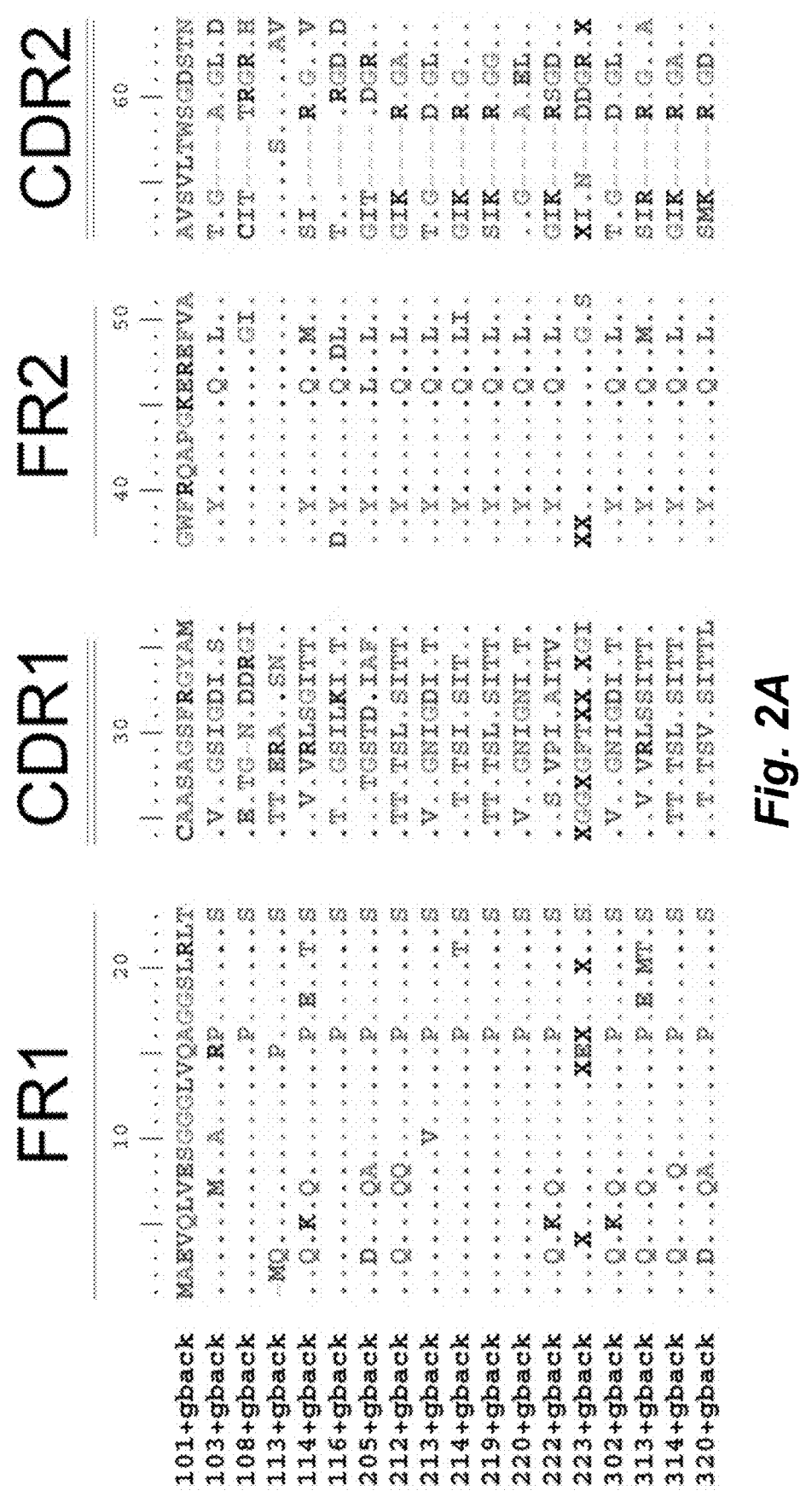
Figure 2B:
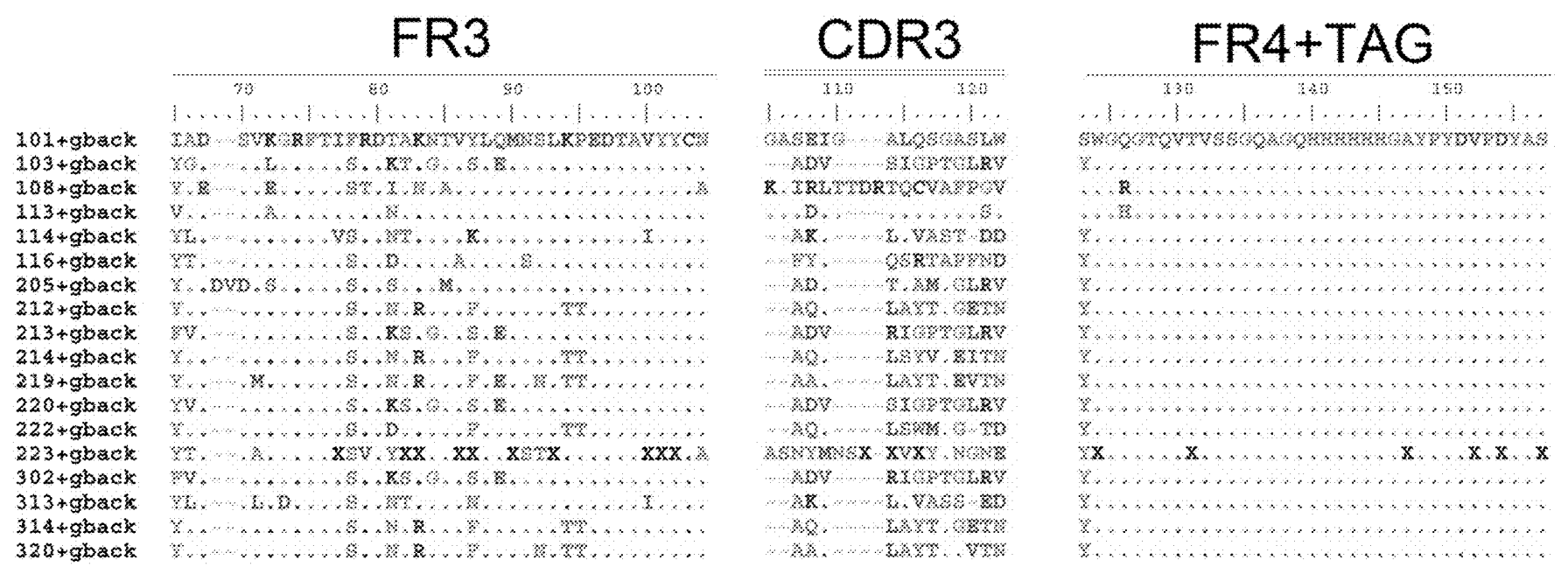

As expected, for approach 1 after 4 rounds of panning ELISA performed with amplified enriched phage library showed a very strong signal selective to Cif as compared to a non-panned library. However, for approach 2, selective signal to Cif increased after 2 rounds of panning and then decreased dramatically approaching non-specific signal as in a non-panned library. Therefore, 24 individual clones where picked after 4 rounds of panning for approach 1 and 30 clones from the second elution for approach 2. All selected phage clones showed recognition of Cif in phage ELISA. The DNA of corresponding clones was isolated, and sequencing revealed that 9 out of 24 clones obtained from approach 1 were unique. Three out of nine selected clones did not show satisfactory protein expression in later experiments and were omitted. In approach 2, 12 out of 30 clones were unique and different from those obtained from the approach 1. Between two approached 5 clones were identified as similar or with minor difference in the sequence of constant domain. Therefore, total of 18 unique clones selective to Cif were identified. Corresponding sequences are shown in FIG. 2. The phagemid vectors containing DNA of unique clones were transformed in TOP10 F' cells and expressed VHHs were purified on Ni-NTA affinity column. The size and purity of the proteins were verified on a 12% SDS-PAGE gel with a major band at MW around 17 kDa.

Figure 3:
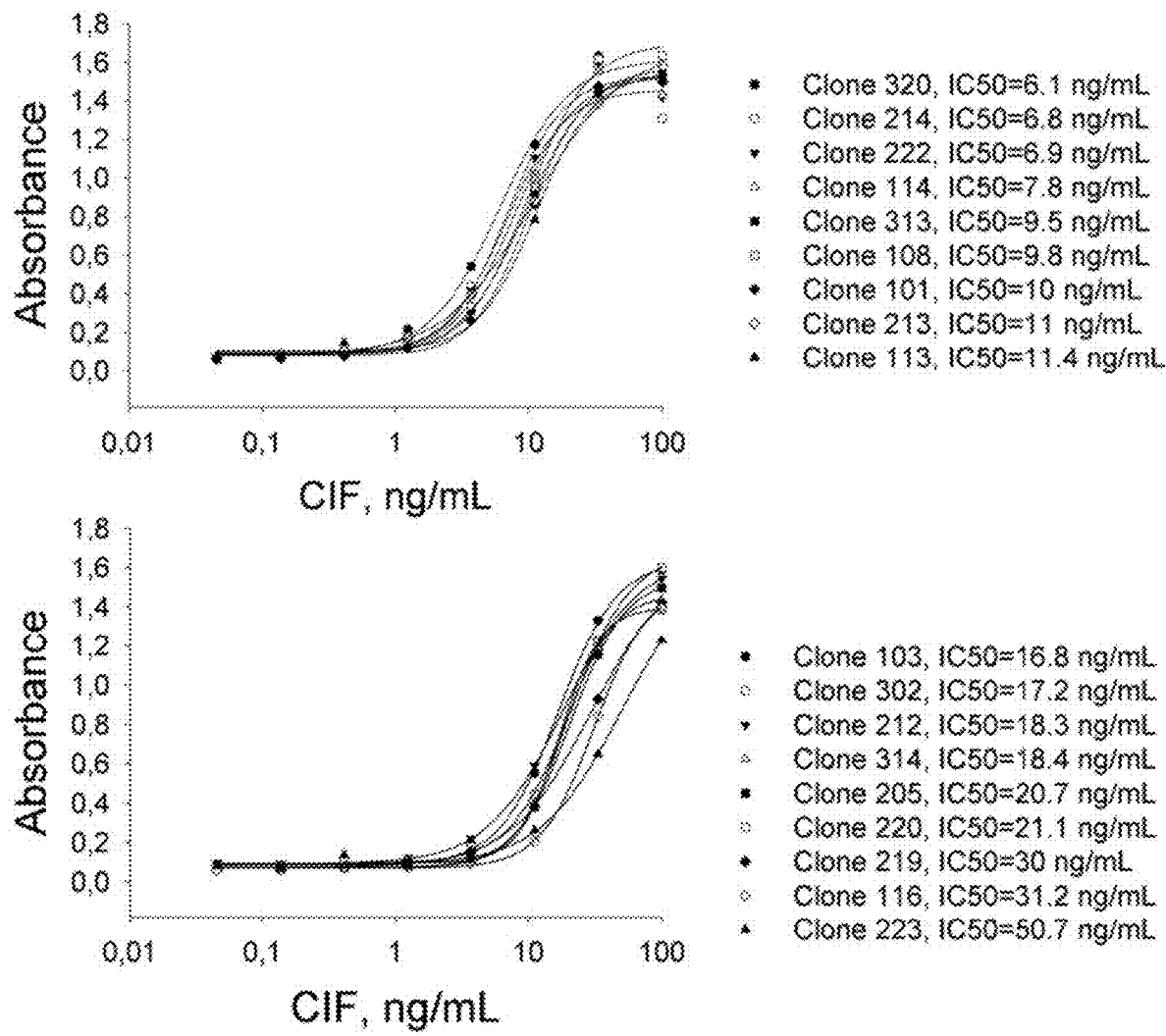
FIG. 3 illustrates ELISA curves for 18 positive clones. Conditions: pAb anti-Cif 0.3 µg/well; serial dilution of Cif in PBS; VHH 50 ng/well in PBS; anti-HA mAb dilution 1:3000 in PBST.

To evaluate produced recombinant antibodies, classical sandwich ELISA was performed using purified rabbit polyclonal anti-Cif antibodies as a capturing antibody (FIG. 3). Its concentration at 0.3 µg/well was selected by checkerboard titration as a minimal amount of antibody necessary to fully cover the well. Any further increase in the amount of loaded antibody did not result in higher signal tested with secondary anti-rabbit antibody conjugated to HRP. Cif protein was loaded in a serial dilution range of 0.05-100 ng/mL and VHHs were added at 50 ng per well. Concentration of VHHs used in the assay was not optimized and was chosen based on previously published literature (24,25) Sensitivity of clones varied by one order with EC50 ranging at 6-51 ng/mL (FIG. 3).

Identification and Characterization of Inhibitory Nanobodies.

Enzyme activity assay was used to determine inhibitory potency of the nanobodies. Small molecule inhibitor was used as a positive control, while non-Cif nanobody was used as a negative control. Eight nanobodies were identified to have inhibitory properties, where nanobodies 113 and 219 were identified as the most potent inhibitors of Cif-enzyme having IC50 values of 0.4 and 0.3 µM respectively (Table 4). Interestingly, they appeared to be more potent than a small molecule inhibitor with IC50 at 14.8 µM (Table 4). For the rest of nanobodies (Table 5) only the estimate of inhibition was given. Importantly, the positive control compound as well as 7 inhibitory nanobodies gave detectable values of IC90, within 2-4 µM, while negative control nanobody and the rest of Cif-selective nanobodies did not allow determining this parameter. The following studies with SPR were continued only with the best performing nanobodies 113 and 219.

TABLE 4

Inhibitory potency of Cif selective VHHs

| Nanobody # | IC$_{50}$ (µM) | IC$_{90}$ (µM) |
| --- | --- | --- |
| KB2115* | 14.8 ± 3.8 | >100 |
| 113 | 0.4 ± 0.0 | 1 ± 0.1 |
| 219 | 0.3 ± 0.0 | 0.9 ± 0.1 |
| 313 | 1.5 ± 0.0 | 4.1 ± 0.1 |
| 114 | 0.9 ± 0.0 | 2.4 ± 0.1 |
| 212 | 0.6 ± 0.0 | 1.6 ± 0.1 |
| 101 | 6.4 ± 0.3 | >14.7 |
| 222 | 0.6 ± 0.1 | 2.0 ± 0.6 |
| 214 | 0.5 ± 0.0 | 1.6 ± 0.1 |

*Small molecule, positive control.

TABLE 5

Screening anti-Cif nanobodies for inhibitory activity.

| Nanobody # | [nab] tested (mg/mL) | % inhibition | Nanobody # | [nab] tested (mg/mL) | % inhibition | Nanobody # | [nab] tested (mg/mL) | % inhibition |
| --- | --- | --- | --- | --- | --- | --- | --- | --- |
| 320 | 0.23 | 9 ± 4 | 114 | 0.21 | 103 ± 2 | 116 | 0.275 | 11 ± 15 |
| 214 | 0.125 | 102 ± 7 | 313 | 0.135 | 111 ± 5 | 213 | 0.55 | 0 ± 6 |
| 222 | 0.19 | 108 ± 4 | 108 | 0.275 | 19 ± 8 | 220 | 0.475 | 0 ± 8 |
| 101 | 0.23 | 94 ± 3 | 302 | 0.5 | 0 ± 3 | 223 | 0.075 | 5 ± 13 |
| 212 | 0.15 | 106 ± 4 | 103 | 0.5 | 2 ± 6 | 3PBAVHH12 | 0.38 | 0 ± 9 |
| 314 | 0.09 | 16 ± 10 | 205 | 0.125 | 0 ± 1 | Buffer | 0 | 0 ± 4 |

Conditions: [Cif] = 0.6 µM, substrate [MNCG] = 25 µM, 37° C., mean ± SD, n = 3, # negative control, nanobody specific to a different target.

To analyze the binding kinetics, single-cycle kinetics was measured with various concentrations of the nanobodies (Nbs): 0.2, 1, 3, 10, 20 nM for Nb-219, and 0.05, 0.5, 2, 8, 20 nM for Nb-113. The Nbs showed very tight binding to the Cif-protein evidenced by long dissociation time (FIG. 4). Therefore, the rate of association rate (ka) was measured from 5 forward reactions where contact time was set at 5 min each, and the dissociation rate (kd) was measured from one reverse reaction with data collection for 20 min for a smooth fit. The curve was fitted with a 1:1 binding model according to the simplest model for the interaction between antigen and antibody. The equilibrium dissociation rate constant (KD) was calculated as a ratio of kd/ka. We determined the binding kinetics of Nb 113 with ka and kd of $5.3 \times 10^5$ $M^{-1}$ s– and $6.9 \times 10^{-5}$ $M^{-1}$ $s^{-1}$, respectively. For Nb 219, ka and kd were determined at $7.4 \times 10^5$ $M^{-1}$ $s^{-1}$ and $5.8 \times 10^{-5}$ $M^{-1}$ $s^{-1}$. The equilibrium dissociation constant (Kd) was estimated at 0.13 and 0.08 nM for Nb 113 and 219, respectively. (Table 6, FIG. 4).

TABLE 6

Kinetic parameters obtained from surface plasmon resonance experiments

| Clone | Ka (1/Ms) | Kd (1/s) | $K_D$ (nM) |
| --- | --- | --- | --- |
| VHH-113 | 526740.1 | $6.91 * 10^{-5}$ | 0.13 |
| VHH-219 | 743688.8 | $5.85 * 10^{-5}$ | 0.08 |

Development of Nanobody-Based Screening Assay.

A sandwich competitive assay was designed to screen for potent inhibitors of Cif enzyme. In this assay, the plate was coated with polyclonal anti-Cif antibody (pAb) that captured Cif-protein. Inhibitory anti-Cif Nb in role of a reporter was added at constant concentration together with a serial dilution of a tested inhibitor. The inhibitor of interest was competing with Nb for the active site of the enzyme (FIG. 5A). The concentration of the inhibitor that resulted in 50% decrease of Nb binding to the plate-coated Cif was named as EC50 concentration (FIG. 5B). The inhibitor with higher potency is expected to produce a smaller EC50. In this assay, the amount of anti-Cif pAb loaded in the plate was optimized first. For this purpose, a serial dilution of pAb was loaded on the plate and after incubation period, the amount of pAb bound to the plate was revealed with secondary antibody loaded in excess. The concentration of pAb at 3 µg/mL was identified as the maximum amount needed and further increase in antibody concentration did not produce further increase in signal. Second, the amount of Cif-protein captured on pAb was optimized. Performed similarly to the first experiment, 20 ng/mL of Cif was sufficient to cover all the pAb and obtain the signal of the secondary antibody reaching a plateau. Nanobody concentration in the assay (5 ng/well) was also optimized to provide the maximum amount necessary to cover all the bound CIF, however avoiding the excess. Both nanobodies 113 and 219 were evaluated in the inhibitory assay. Even though the concept of inhibitory sandwich assay worked with both nanobodies, Nb113 was constantly showing highly variable signal and the curve was not fitted smoothly. Therefore, further experiments were performed with Nb219.

The sandwich competitive assay with Nb 219 was used to analyze a range of small molecule inhibitors including commercially available KB2115 as a positive control, non-specific compound 1k as a negative control and synthetic compounds, 8c, 8d, 8f, 8h and 8j all with known affinity to Cif.23 In addition, two new compounds the potential inhibitors of Cif were included in this study, compounds 18f and 18NH$_2$. FIG. 5B demonstrates competition curves obtained with sandwich ELISA while Table 7 provides structures of the tested compounds as well as EC50 values obtained with the Nb-based assay and IC50 values obtained with fluorescent assay.

TABLE 7

Potency comparison of small molecule inhibitors in VHH-based (dsELISA) and fluorescent assays, and equilibrium parameter (KD) obtained from bio-layer interferometry experiments.

| Cmpd. # | Structure | Chemical Name | dsELISA EC$_{50}$,µM | Fluorescent assay IC$_{50}$,µM | K$_D$$^a$ (µM) |
|---|---|---|---|---|---|
| 1$^T$ (1k) | 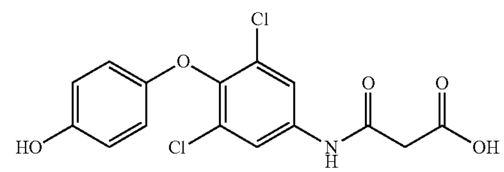 [SMILES: O=C(O)CC(=O)Nc1cc(Cl)c(Oc2ccc(O)cc2)c(Cl)c1] | 3-((3,5-dichloro-4-(4-hydroxyphenoxy)phenyl)amino)-3-oxopropanoic acid | >200 | >250 | |
| KB2115 (1a) | 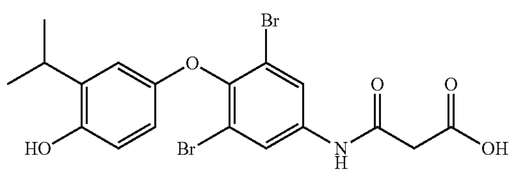 [SMILES: CC(C)c1cc(Oc2c(Br)cc(NC(=O)CC(=O)O)cc2Br)ccc1O] | 3-((3,5-dibromo-4-(4-hydroxy-3-isopropylphenoxy)phenyl)amino)-3-oxopropanoic acid | 13 ± 1 | 2.6 | |
| 2$^T$ (8d) | 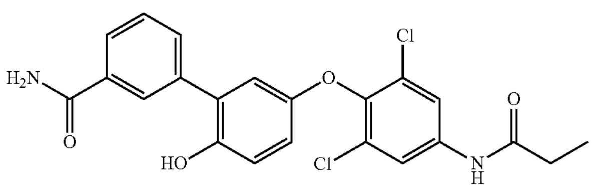 [SMILES: CCC(=O)Nc1cc(Cl)c(Oc2ccc(O)c(-c3cccc(C(N)=O)c3)c2)c(Cl)c1] | 5'-(4-acetamido-2,6-dichlorophenoxy)-2'-hydroxy-[1,1'-biphenyl]-3-carboxamide | 3.1 ± 1.0 | 0.46 | |
| 3$^T$ (8f) | 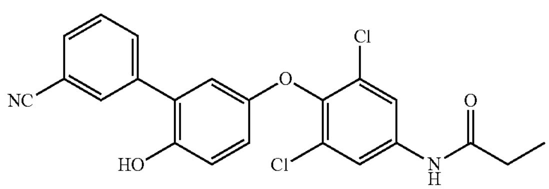 [SMILES: CCC(=O)Nc1cc(Cl)c(Oc2ccc(O)c(-c3cccc(C#N)c3)c2)c(Cl)c1] | N-(3,5-dichloro-4-((3'-cyano-6-hydroxy-[1,1'-biphenyl]-3-yl)oxy)phenyl)acetamide | 3.0 ± 1.1 | 0.58 | |
| 4$^T$ (8h) | 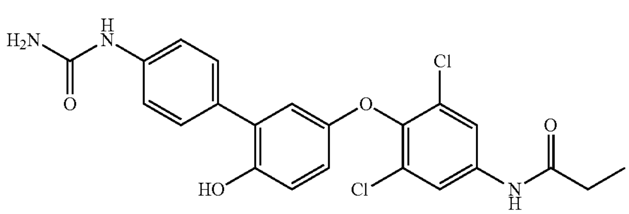 [SMILES: CCC(=O)Nc1cc(Cl)c(Oc2ccc(O)c(-c3ccc(NC(N)=O)cc3)c2)c(Cl)c1] | N-(3,5-dichloro-4-((6-hydroxy-4'-ureido-[1,1'-biphenyl]-3-yl)oxy)phenyl)acetamide | 2.5 ± 0.9 | 0.29 | 2.1 ± 0.7 |
| 5$^T$ (8j) | 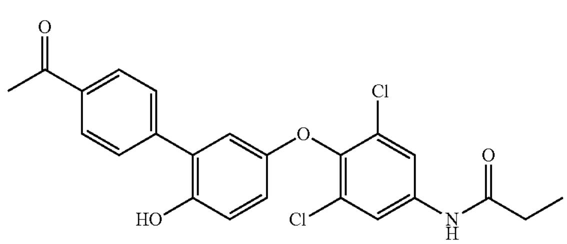 [SMILES: CCC(=O)Nc1cc(Cl)c(Oc2ccc(O)c(-c3ccc(C(C)=O)cc3)c2)c(Cl)c1] | N-(4-((4'-acetyl-6-hydroxy-[1,1'-biphenyl]-3-yl)oxy)-3,5-dichlorophenyl)acetamide | 1.5 ± 0.7 | 0.35 | |

TABLE 7-continued

Potency comparison of small molecule inhibitors in VHH-based (dsELISA) and fluorescent assays, and equilibrium parameter (KD) obtained from bio-layer interferometry experiments.

| Cmpd. # | Structure | Chemical Name | dsELISA EC$_{50}$, μM | Fluorescent assay IC$_{50}$, μM | K$_D{}^a$ (μM) |
|---|---|---|---|---|---|
| 6$^T$ (8c) | | 5'-(4-acetamido-2,6-dichlorophenoxy)-2'-hydroxy-[1,1'-biphenyl]-4-carboxamide | 1.2 ± 0.3 | 0.35 | 0.5 ± 0.1 |
| 7* (18NH$_2$) | 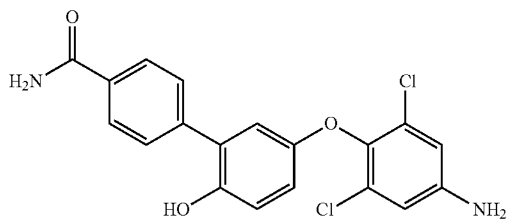 [SMILES: NC(=O)c1ccc(-c2cc(Oc3c(Cl)cc(N)cc3Cl)ccc2O)cc1] | 5'-(4-amino-2,6-dichlorophenoxy)-2'-hydroxy-[1,1'-biphenyl]-4-carboxamide | 0.7 ± 0.3 | 0.55 | 0.9 ± 0.1 |
| 8* (18f) | 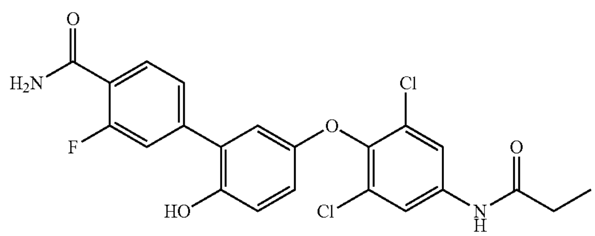 [SMILES: CCC(=O)Nc1cc(Cl)c(Oc2ccc(O)c(-c3ccc(C(N)=O)c(F)c3)c2)c(Cl)c1] | 5'-(2,6-dichloro-4-propionamidophenoxy)-3-fluoro-2'-hydroxy-[1,1'-biphenyl]-4-carboxamide | 0.2 ± 0.1 | 0.47 | 0.2 ± 0.0 |

Results shown as mean ± SD (n = 2 or 3).
$^a$Data calculated based on steady state analysis;
$^T$synthesized and reported in 14,
*synthesized and reported herein.

The sandwich competitive/displacment assay and enzyme activity assay have different principles of interaction, thus absolute values for IC50 and EC50 are different. Nevertheless, IC50 from enzyme activity assay correlated well with EC50 of sandwich competitive assay. For the positive control KB2115, both assays gave a positive readout, while the assays with a negative control 1 k, both assays gave relatively high values of EC50/IC50 values, corresponding to low inhibitory activity in the enzyme activity assay and low competitive potency in the Nb-based assay. For the compounds 8d, 8f, 8j and 8h there was a trend in decreasing IC50 values from the fluorescent assay and decrease in EC50 values from the Nb-based assay, suggesting that both methods detect similarly increase in potency of the tested inhibitors. For the compound 8c EC50 was further decreasing while IC50 was around 0.35 μM. Both assays were also applied to study new compounds 18NH$_2$ and 18f. Their IC50 values were low, around 0.5 μM suggesting that they are good inhibitors, but less potent since 8j, 8h and 8c had an IC50 around 0.3 μM. On the other hand, the Nb-based assay showed that 18NH$_2$ was as potent as 8c and better than 8h and 8j. In addition, Nb-based assay identified the compound 18f as far more efficient inhibitor compared to the rest of the tested compounds, having EC50 of 0.2 μM.

To verify these findings we measured the affinity toward Cif-protein of the new compounds 18f and 18NH$_2$, as well as 8c and 8h, as a control, with Octet bio-layer interferometry (Octet). We found that 8c had higher affinity to Cif with KD of 0.5±0.1 μM compared to 8h with KD of 2.1±0.7 μM. Indeed, Nb-based assay also indicated that 8c was more potent than 8h, with EC50 1.0 vs 1.7 μM, while fluorescent assay reached its sensitivity limit and showed IC50 for both compounds at 0.3 μM. Most importantly, similarly to Nb-based assay, Octet experiment showed that the compound 18f was indeed the most potent inhibitor among all tested candidates with KD of 0.16±0.02 μM. The results are summarized in Table 7.

To further evaluate the assay performance, inter- and intra-day variation was assessed as well as the reproducibility of the results. To determine the intra-day variation, we analyzed results obtained on the same plate and day in duplicates and tested on two different days. The intra-day variation was generally below 20%. Inter-day variation was calculated by using results obtained within one week, in addition to results obtained over a five-month period. From these data variations in absolute EC50 value were found to be up to 45% (FIG. 7).

Discussion

A number of high-throughput techniques are developed for drug screening. When the drugs aim to inhibit the enzymatic activity of the protein, this catalytic activity is often involved in the screening process. For example, any fast method including scintillation proximity assay, homogeneous time-resolved fluorescence assay (HTRF) or fluorescent polarization assay, for screening of inhibitory small molecules for kinases involves kinase mediated phosphorylation of the standard peptide attached to a reported. Then, this phosphorylated peptide undergoes the next steps of the method. For instance, in fluorescence polarization, the phosphorylated peptide binds to an anti-phospho antibody, and gives rise to a high polarization signal (26,27). To be efficient and fast, these methods are therefore generally used for fast enzymes. In contrast, slow enzymes with low activity, as for example family of p450 enzymes, would give assays with low sensitivity. Therefore, drug evaluation on these enzymes is performed in combination of enzymatic reaction and highly sensitive analytical detection methods like LC-MS/MS (7)

The use of inhibitory nanobodies in a competitive sandwich format appear as an interesting alternative to existing screening methods. The developed assay involves a competition between a nanobody and a studied small molecule inhibitor for the active site of the protein immobilized on the support. To develop the assay, we first took advantage of the phage display panning procedure to isolate nanobody clones with high affinity to Cif. As a part of the biopanning procedure, a pool of phages with individual VHH protein expressed in fusion with pIII surface protein of the phage was exposed to the Cif protein, coated on the solid support. Cif-selective nanobodies bound to the Cif-coated support, while the rest of phages bearing non-specific nanobodies were washed away. We then performed a number of panning cycles where concentration of the Cif on the surface support was decreasing, to ensure selection of only clones with very high affinity, and washing was performed with increasingly stringent conditions, to eliminate non-specific binders. Such panning strategy has been shown to be effective for phage pool enrichment with phages selective to the target analyte (28). In addition, panning with increasingly stringent conditions (increased wash and decreased coating antigen) is more frequently used in panning for selective small molecule binders, while for proteins panning is done with constant concentration of the coating protein. Unlike published reports, we used low amount of Cif even at the first round of panning (starting with 10 µg/mL and lower). We assume that all these improvements in the panning procedure applied to Cif, had a significant contribution to the success of isolation of positive clones.

We also tried two different approached for panning, where Cif was either coated directly on the solid support or on the polyclonal anti-Cif antibody absorbed on the solid support. Interestingly, we observed dramatically different outcomes for these approaches. When the Cif was coated through pAb (and after elution post-panned in pAb only coated well to remove binders of pAb) the overall panning process followed a common path resulting in a pool of phages enriched in selective binders after 4 rounds of panning. However, when the Cif was directly coated on the plate, the phage pool of selective binders increased after 2 rounds of panning but after 3rd and 4th rounds all selective binders were lost. It is therefore possible that the low concentration of Cif that we used compared to the published reports and extensive wash might resulted in isolation of only few clones that have been lost due to poor amplification efficiency compared to non-selective binders that are always present in output of the panning round. Therefore, for successful isolation of positive clones either higher concentration of the protein should be used for coating or efficient assisted presentation to the phage pool should be employed (e.g., exposure through selective pAb, or streptavidin for biotinylated protein etc.). Assisted presentation may be particularly useful for the panning directed to a specific part of the molecule, when the site of interested is better exposed to the phage while the other part of the molecule is "hidden".

We identified 18 out of 54 tested clones with unique sequences (with at least 2 different amino acids in the CDR domain, FIGS. 2 and 6). The nanobodies were confirmed to recognize Cif with sandwich ELISA where pAb served as a capturing agent and corresponding VHH as a detection agent. All clones showed recognition of the Cif protein and the sensitivity of clones varied by one order with EC50 ranging at 6-51 ng/mL (FIG. 3). This sensitivity level is largely appropriate for diagnostic purposes. For example, using western blot analysis, Flitter, et al. (21) reported Cif concentration in the range of 200-2000 ng/mL in BALF of patients with cystic fibrosis.

We then aimed in identification of the nanobody clones that could inhibit epoxy hydrolyzing activity of the Cif. Therefore, for the screening and identification of such clones, we employed well-established and characterized a fluorescent based assay (29,30), where a non-fluorescent reporter containing epoxide group is hydrolyzed by Cif to give an intermediate that spontaneously transforms in the fluorescent probe. By adding inhibitors the rate of hydrolysis decreases in function of inhibitor potency. As discussed earlier, the sensitivity of such assay depends on nature of the enzyme. For example, the sensitivity of the assay with active soluble epoxide hydrolase (sEH) is in the low nanomolar range (See, e.g., Jones, et al., *Anal Biochem.* 343(1):66-75), while a similar assay for a slow Cif enzyme has a sensitivity of 0.3 µM (23). When in the fluorescence assay the Cif is used at concentration lower than 0.6 µM, the initial fluorescent signal is very low and thus inhibition with small molecule inhibitor is hard to detect. Therefore, Cif enzymatic activity assay was run with Cif at 0.6 µM. At this condition, the minimal theoretical sensitivity (IC50) that can be obtained is 0.3 µM. Consequently, the inhibitors with IC50 lower than 0.3 µM could not be identified. From 18 nanobodies expressed, two nanobodies (Nb 113 and Nb 219) showed strong inhibiting efficiency with a potency close to small molecule inhibitor (Table 4). Other proteins did not show inhibition or the IC50 value could not be determined. Affinity studies with SPR technique showed that developed inhibitory nanobodies 113 and 219 had very high affinity to the Cif with KD values 0.130 and 0.08 nM, respectively. This is a very high affinity compared to the published literature data on affinity of nanobodies to their protein substrates, with values usually in the range of 10-500 nM (11,17,31,32). Interestingly, Rossotti, et al. (11) reported nanobodies with affinities comparable to our results. They obtained nanobodies to human sEH with KD around 0.5 nM and the authors also used a sophisticated panning procedure including extensive wash.

A crystallization of nanobody with Cif is being made. However, co-crystallization of two proteins is a challenging task. There are few possible mechanisms of inhibition. Nanobodies are known to have the CDR3 regions unusually long and they have been shown to possess the extraordinary capacity to form convex extensions that extend into cavities like active sites of enzymes, binding pockets of the transporters or receptors. A number of recent studies successfully demonstrated that nanobodies block the enzymatic (32-34), cytotoxic activity (35) of proteins and modulate the receptor functioning (36). Another very often described phenomenon is the ability of nanobodies to inhibit enzymes through an allosteric modulation of the enzymatic activity (37-39). The binding to an allosteric site, a site different from the active catalytic site of the enzyme, may induce conformational changes within the protein structure and thus change of catalytic site resulting in decrease in substrate recognition. Finally, nanobody may create a steric hindrance of the entrance to the active site thus preventing the substrate diffusion to the active site. For example, Zhu, et al. (32) demonstrated that a nanobody to furin inhibited the cleavage of furin substrates, while small peptide substrates still could enter the catalytic cleft of furin and was leaved. Therefore, they concluded that nanobody did not bind directly to the catalytic pocket but rather at some distance from the active site. In our study, the mechanism of inhibition is unknown so far.

Based on inhibitory properties of the selected nanobodies we designed an immunoassay capable to differentiate small molecule inhibitors based on their inhibitory potency. To evaluate the performance of the assay we initially tested a number of characterized compound. The results in Table 7 show very good agreement between fluorescent and nanobody-based assays. In both format, inhibitor 1k tested as a negative control competed poorly with a reporter or nanobody respectively. A positive control, a commercial compound 1a, had a moderate inhibitory potency in both assays. A library of synthetic compounds was previously prepared and reported by Kitamura, et al. (23). The authors measured the inhibitory efficiency with fluorescent assay and confirmed measurements by surface plasmon resonance (SPR). From the available library we selected the most potent inhibitors 8c, 8j and 8h, as well as less potent 8f and 8d for comparison purposes (Table 7). Similarly to fluorescent assay, all synthetic compounds showed strong inhibition of the nanobody-based assay. Interestingly, compounds 8d and 8h showed similar activity in the nanobody-based assay, while they had certain difference in potency when tested with fluorescent assay. Furthermore, we observed increase in potency within 8h, 8j and 8c inhibitors with nanobody-based assay, while fluorescent based assay signal varied around 0.3 values, that it is its limit of detection. Therefore, with nanobody-based assay we were able to see the difference in the inhibitory potencies of the compounds. These results are supported by the data published by Kitamura, et al. (23) where using SPR they demonstrated that the compound 8c was the most potent inhibitor.

Next, we applied the developed nanobody-based inhibitory sandwich ELISA to screen a library of new synthetic compounds. Two compounds 18NH$_2$ and 18f were identified as highly potent inhibitors, with 18f being 1 fold more potent then 8c identified by Kitamura, et al. (23). On the other hand, fluorescent based assay gave IC50 values higher than theoretical limit of detection, 0.55 and 0.47 vs 0.3 µM. It is possible that the error of the fluorescent based is high when the potency of the inhibitor approaches 0.3 µM resulting in inaccurate estimation of the IC50 value. Bio-layer interferometry with Octet instrument confirmed high affinity of the identified compounds to Cif-protein. Interestingly, despite different mechanism of interaction and measurements in Octet experiments and Nb-based ELISA, the KD and EC50 values were remarkably close between methods with KD being 0.5, 2.1, 0.9 and 0.2 µM vs EC50 of 1.2, 2.5, 0.7 and 0.2 µM for compounds 8c, 8h, 18NH$_2$ and 18f, respectively.

To conclude, using inhibitory VHHs raised against CIF we developed a novel approach and an assay to sort small molecule inhibitors according to their efficacy to compete with antibody for the binding site. Competing efficacy of the small inhibitors was shown to be correlating with their enzyme inhibitory properties as well as Cif binding affinity. The developed assay is advantageous over currently existing fluorescent based assay since it provides higher sorting efficiency with at least 10 times higher sensitivity. This assay can also be used as relatively high throughput technique for enzymes with slow turn over, that is a cheap and fast alternative to currently employed method combining the enzymatic hydrolysis reaction with subsequent LC-MS/MS analysis. The nanobody-based competitive assay does not directly involve the catalytic site of the enzyme and therefore, it can be generally translated to non-catalytic proteins. This important conclusion suggests that the developed approach can be used for the screening of small molecule inhibitors for the receptors, cell membrane proteins and other relevant protein targets. Therefore, the nanobody-assay can act as a convenient alternative tool for drug screening process.

REFERENCES

1 Wu, S. & Liu, B. Application of scintillation proximity assay in drug discovery. BioDrugs 19, 383-392 (2005).
2 Glickman, J. F., Schmid, A. & Fernand, S. Scintillation proximity assays in high-throughput screening. Assay Drug Dev Technol 6, 433-455, doi:10.1089/adt.2008.135 (2008).
3 Tian, H., Ip, L., Luo, H., Chang, D. C. & Luo, K. Q. A high throughput drug screen based on fluorescence resonance energy transfer (FRET) for anticancer activity of compounds from herbal medicine. British journal of pharmacology 150, 321-334, doi:10.1038/sj.bjp.0706988 (2007).
4 Lea, W. A. & Simeonov, A. Fluorescence polarization assays in small molecule screening. Expert Opin Drug Discov 6, 17-32, doi:10.1517/17460441.2011.537322 (2011).
5 von Ahsen, 0. & Bomer, U. High-throughput screening for kinase inhibitors. Chembiochem 6, 481-490, doi:10.1002/cbic.200400211 (2005).
6 Donato, M. T., Jimenez, N., Castell, J. V. & Gomez-Lechon, M. J. Fluorescence-based assays for screening nine cytochrome P450 (P450) activities in intact cells expressing individual human P450 enzymes. Drug Metab Dispos 32, 699-706, doi:DOI 10.1124/dmd.32.7.699 (2004).
7 Qin, C. Z. et al. A high-throughput inhibition screening of major human cytochrome P450 enzymes using an in vitro cocktail and liquid chromatography-tandem mass spectrometry. Biomed Chromatogr 28, 197-203, doi:10.1002/bmc.3003 (2014).
8 Hamers-Casterman, C. et al. Naturally-Occurring Antibodies Devoid of Light-Chains. Nature 363, 446-448, doi:Doi 10.1038/363446a0 (1993).
9 Chen, A. et al. Smartphone-interfaced lab-on-a-chip devices for field-deployable enzyme-linked immunosorbent assay. Biomicrofluidics 8, 064101, doi:10.1063/1.4901348 (2014).
10 Bever, C. S. et al. VHH antibodies: emerging reagents for the analysis of environmental chemicals. Anal Bioanal Chem 408, 5985-6002, doi:10.1007/s00216-016-9585-x (2016).
11 Rossotti, M. A. et al. Method for Sorting and Pairwise Selection of Nanobodies for the Development of Highly Sensitive Sandwich Immunoassays. Anal Chem 87, 11907-11914, doi:10.1021/acs.analchem.5b03561 (2015).
12 Nam, D. H., Rodriguez, C., Remacle, A. G., Strongin, A. Y. & Ge, X. Active-site MMP-selective antibody inhibitors discovered from convex paratope synthetic libraries. P Natl Acad Sci USA 113, 14970-14975, doi:10.1073/pnas.1609375114 (2016).

13 Maussang, D. et al. Llama-derived Single Variable Domains (Nanobodies) Directed against Chemokine Receptor CXCR7 Reduce Head and Neck Cancer Cell Growth in Vivo. J Biol Chem 288, 29562-29572, doi:10.1074/jbc.M113.498436 (2013).

14 Wesolowski, J. et al. Single domain antibodies: promising experimental and therapeutic tools in infection and immunity. Med Microbiol Immun 198, 157-174, doi:10.1007/s00430-009-0116-7 (2009).

15 Dmitriev, O. Y., Lutsenko, S. & Muyldermans, S. Nanobodies as Probes for Protein Dynamics in Vitro and in Cells. J Biol Chem 291, 3767-3775, doi:10.1074/jbc.R115.679811 (2016).

16 Obishakin, E. et al. Generation of a Nanobody Targeting the Paraflagellar Rod Protein of Trypanosomes. Plos One 9, doi:ARTN e11589310.1371/journal.pone.0115893 (2014).

17 Schmitz, K. R., Bagchi, A., Roovers, R. C., Henegouwen, P. M. P. V. E. & Ferguson, K. M. Structural Evaluation of EGFR Inhibition Mechanisms for Nanobodies/VHH Domains. Structure 21, 1214-1224, doi:10.1016/j.str.2013.05.008 (2013).

18 Bahl, C. D. et al. Crystal structure of the cystic fibrosis transmembrane conductance regulator inhibitory factor Cif reveals novel active-site features of an epoxide hydrolase virulence factor. Journal of bacteriology 192, 1785-1795, doi:10.1128/JB.01348-09 (2010).

19 Bahl, C. D. & Madden, D. R. *Pseudomonas aeruginosa* Cif defines a distinct class of alpha/beta epoxide hydrolases utilizing a His/Tyr ring-opening pair. Protein and peptide letters 19, 186-193 (2012).

20 MacEachran, D. P. et al. The *Pseudomonas aeruginosa* secreted protein PA2934 decreases apical membrane expression of the cystic fibrosis transmembrane conductance regulator. Infection and immunity 75, 3902-3912, doi:10.1128/IAI.00338-07 (2007).

21 Flitter, B. A. et al. *Pseudomonas aeruginosa* sabotages the generation of host proresolving lipid mediators. P Natl Acad Sci USA 114, 136-141, doi:10.1073/pnas.1610242114 (2017).

22 Bahl, C. D. et al. The cif Virulence Factor Gene Is Present in Isolates From Patients With *Pseudomonas aeruginosa* Keratitis Cornea 36, 358-362 (2017).

23 Kitamura, S. et al. Rational Design of Potent and Selective Inhibitors of an Epoxide Hydrolase Virulence Factor from *Pseudomonas aeruginosa*. J Med Chem 59, 4790-4799, doi:10.1021/acs.jmedchem.6b00173 (2016).

24 Bever, C. R. S. et al. Development and Utilization of Camelid VHH Antibodies from Alpaca for 2,2',4,4'-Tetrabrominated Diphenyl Ether Detection. Anal Chem 86, 7875-7882, doi:10.1021/ac501807j (2014).

25 Wang, J. et al. Heterologous Antigen Selection of Camelid Heavy Chain Single Domain Antibodies against Tetrabromobisphenol A. Anal Chem 86, 8296-8302, doi:10.1021/ac5017437 (2014).

26 Fowler, A. et al. An evaluation of fluorescence polarization and lifetime discriminated polarization for high throughput screening of serine/threonine kinases. Anal Biochem 308, 223-231, doi:Pii 50003-2697(02)00245-2Doi 10.1016/S0003-2697(02)00245-2 (2002).

27 Turek-Etienne, T. C. et al. Use of red-shifted dyes in a fluorescence polarization AKT kinase assay for detection of biological activity in natural product extracts. J Biomol Screen 9, 52-61, doi:10.1177/1087057103259346 (2004).

28 Tabares-da Rosa, S. et al. Competitive Selection from Single Domain Antibody Libraries Allows Isolation of High-Affinity Antihapten Antibodies That Are Not Favored in the llama Immune Response. Anal Chem 83, 7213-7220, doi:10.1021/ac201824z (2011).

29 Bahl, C. D. et al. Inhibiting an Epoxide Hydrolase Virulence Factor from *Pseudomonas aeruginosa* Protects CFTR. Angew Chem Int Edit 54, 9881-9885, doi:10.1002/anie.201503983 (2015).

30 Morisseau, C. et al. Development of fluorescent substrates for microsomal epoxide hydrolase and application to inhibition studies. Anal Biochem 414, 154-162, doi:10.1016/j.ab.2011.02.038 (2011).

31 Ghannam, A., Kumari, S., Muyldermans, S. & Abbady, A. Q. Camelid nanobodies with high affinity for broad bean mottle virus: a possible promising tool to immunomodulate plant resistance against viruses. Plant Mol Biol 87, 355-369, doi:10.1007/s11103-015-0282-5 (2015).

32 Zhu, J. J. et al. Generation and characterization of non-competitive furin-inhibiting nanobodies. Biochem J 448, 73-82, doi:10.1042/Bj20120537 (2012).

33 Buelens, K., Hassanzadeh-Ghassabeh, G., Muyldermans, S., Gils, A. & Declerck, P. J. Generation and characterization of inhibitory nanobodies towards thrombin activatable fibrinolysis inhibitor. J Thromb Haemost 8, 1302-1312, doi:10.1111/j.1538-7836.2010.03816.x (2010).

34 Menzel, S., Rissiek, B., Haag, F., Goldbaum, F. A. & Koch-Nolte, F. The art of blocking ADP-ribosyltransferases (ARTs): nanobodies as experimental and therapeutic tools to block mammalian and toxin ARTs. The FEBS journal 280, 3543-3550, doi:10.1111/febs.12313 (2013).

35 Unger, M. et al. Selection of Nanobodies that Block the Enzymatic and Cytotoxic Activities of the Binary *Clostridium Difficile* Toxin CDT. Sci Rep-Uk 5, doi:Artn 785010.1038/Srep07850 (2015).

36 Jahnichen, S. et al. CXCR4 nanobodies (VHH-based single variable domains) potently inhibit chemotaxis and HIV-1 replication and mobilize stem cells. P Natl Acad Sci USA 107, 20565-20570, doi:10.1073/pnas.1012865107 (2010).

37 Barlow, J. N., Conrath, K. & Steyaert, J. Substrate-dependent modulation of enzyme activity by allosteric effector antibodies. Bba-Proteins Proteom 1794, 1259-1268, doi:10.1016/j.bbapap.2009.03.019 (2009).

38 Sohier, J. S. et al. Allosteric inhibition of VIM metallo-beta-lactamases by a camelid nanobody. Biochem J 450, 477-486, doi:10.1042/BJ20121305 (2013).

39 Oyen, D., Srinivasan, V., Steyaert, J. & Barlow, J. N. Constraining enzyme conformational change by an antibody leads to hyperbolic inhibition. J Mol Biol 407, 138-148, doi:10.1016/j.jmb.2011.01.017 (2011).

40 Kitamura, S. et al. Rational Design of Potent and Selective Inhibitors of an Epoxide Hydrolase Virulence Factor from *Pseudomonas aeruginosa*. J. Med. Chem. 59, 4790-4799, doi:10.1021/acs.jmedchem.6b00173 (2016).

41 Tabares-da Rosa, S. et al. Competitive selection from single domain antibody libraries allows isolation of high-affinity antihapten antibodies that are not favored in the llama immune response. Analytical chemistry 83, 7213-7220 (2011).

42 Zarebski, L. M., Urrutia, M. & Goldbaum, F. A. Llama single domain antibodies as a tool for molecular mimicry. Journal of molecular biology 349, 814-824 (2005).

43 Barbas, C. F. Phage Display: A Laboratory Manual. (Cold Spring Harbor Laboratory Press, 2001).

44 Wang, J. et al. Heterologous antigen selection of camelid heavy chain single domain antibodies against tetrabromobisphenol A. Analytical chemistry 86, 8296-8302 (2014).

45 Bever, C. R. et al. Development and Utilization of Camelid VHH Antibodies from Alpaca for 2,2',4,4'-Tetrabrominated Diphenyl Ether Detection. Analytical chemistry 86, 7875-7882 (2014).

46 Lorimer, I. A. J. et al. Recombinant immunotoxins specific for a mutant epidermal growth factor receptor: Targeting with a single chain antibody variable domain isolated by phage display. P Natl Acad Sci USA 93, 14815-14820, doi:DOI 10.1073/pnas.93.25.14815 (1996).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method of identifying *Pseudomonas aeruginosa* infection in a mammalian subject in need thereof, comprising:
   (i) identifying a mammalian subject exhibiting symptoms consistent with a *Pseudomonas aeruginosa* infection;
   (ii) obtaining a biological sample from the mammalian subject;
   (iii) contacting the biological sample with an isolated, recombinant, synthetic and/or non-natural anti-Cif VHH molecule that specifically binds to cystic fibrosis transmembrane conductance regulator (CFTR) inhibitory factor (Cif) molecules secreted by *Pseudomonas aeruginosa* under conditions that allow the anti-Cif VHH molecule to bind specifically to the Cif molecules potentially in the sample; and
   (iv) identifying the subject as having a *Pseudomonas aeruginosa* infection upon positive detection of specific binding of the anti-Cif VHH molecule to the Cif molecules in the sample,
   wherein the anti-Cif VHH molecule comprises:
   a) a CDR1 comprising SEQ ID NO:2, a CDR2 comprising SEQ ID NO:3 and a CDR3 comprising SEQ ID NO:4:
   b) a CDR1 comprising SEQ ID NO:6, a CDR2 comprising SEQ ID NO:7 and a CDR3 comprising SEQ ID NO:8;
   c) a CDR1 comprising SEQ ID NO:10, a CDR2 comprising SEQ ID NO:11 and a CDR3 comprising SEQ ID NO:12;
   d) a CDR1 comprising SEQ ID NO:14, a CDR2 comprising SEQ ID NO:15 and a CDR3 comprising SEQ ID NO:16;
   e) a CDR1 comprising SEQ ID NO:18, a CDR2 comprising SEQ ID NO:19 and a CDR3 comprising SEQ ID NO:20;
   f) a CDR1 comprising SEQ ID NO:22, a CDR2 comprising SEQ ID NO:23 and a CDR3 comprising SEQ ID NO:24,
   g) a CDRI1 comprising SEQ ID NO:26, a CDR2 comprising SEQ ID NO:27 and a CDR3 comprising SEQ ID NO:28;
   h) a CDR1 comprising SEQ ID NO:30, a CDR2 comprising SEQ ID NO:31 and a CDR3 comprising SEQ ID NO:32;
   i) a CDRI1 comprising SEQ ID NO:34, a CDR2 comprising SEQ ID NO:35 and a CDR3 comprising SEQ ID NO:36;
   j) a CDR1 comprising SEQ ID NO:38, a CDR2 comprising SEQ ID NO:39 and a CDR3 comprising SEQ ID NO:40;
   k) a CDR1 comprising SEQ ID NO:42, a CDR2 comprising SEQ ID NO:43 and a CDR3 comprising SEQ ID NO:44;
   l) a CDR1 comprising SEQ ID NO:46, a CDR2 comprising SEQ ID NO:47 and a CDR3 comprising SEQ ID NO:48;
   m) a CDR1 comprising SEQ ID NO:50, a CDR2 comprising SEQ ID NO:51 and a CDR3 comprising SEQ ID NO:52;
   o) a CDR1 comprising SEQ ID NO:58, a CDR2 comprising SEQ ID NO:59 and a CDR3 comprising SEQ ID NO:60;
   p) a CDR1 comprising SEQ ID NO:62, a CDR2 comprising SEQ ID NO:63 and a CDR3 comprising SEQ ID NO:64;

q) a CDR1 comprising SEQ ID NO:66, a CDR2 comprising SEQ ID NO:67 and a CDR3 comprising SEQ ID NO:68; or
r) a CDR1 comprising SEQ ID NO:70, a CDR2 comprising SEQ ID NO:71 and a CDR3 comprising SEQ ID NO:72.

2. The method of claim 1, wherein the biological sample comprises saliva, sputum, bronchoalveolar lavage fluid (BALF), cheek swab, mucus, blood, sweat, tears, serum, plasma, urine, skin, cerebral spinal fluid (CSF), lymph, Eustachian tube fluid, bone marrow or feces.

3. The method of claim 1, wherein the anti-Cif VHH molecule comprises:
a) a CDR1 comprising SEQ ID NO:2, a CDR2 comprising SEQ ID NO:3 and a CDR3 comprising SEQ ID NO:4.

4. The method of claim 1, wherein the anti-Cif VHH molecule comprises:
b) a CDR1 comprising SEQ ID NO:6, a CDR2 comprising SEQ ID NO:7 and a CDR3 comprising SEQ ID NO:8.

5. The method of claim 1, wherein the anti-Cif VHH molecule comprises:
c) a CDR1 comprising SEQ ID NO:10, a CDR2 comprising SEQ ID NO:11 and a CDR3 comprising SEQ ID NO:12.

6. The method of claim 1, wherein the anti-Cif VHH molecule comprises:
d) a CDR1 comprising SEQ ID NO:14, a CDR2 comprising SEQ ID NO:15 and a CDR3 comprising SEQ ID NO:16.

7. The method of claim 1, wherein the anti-Cif VHH molecule comprises:
e) a CDR1 comprising SEQ ID NO:18, a CDR2 comprising SEQ ID NO:19 and a CDR3 comprising SEQ ID NO:20.

8. The method of claim 1, wherein the anti-Cif VHH molecule comprises:
f) a CDR1 comprising SEQ ID NO:22, a CDR2 comprising SEQ ID NO:23 and a CDR3 comprising SEQ ID NO:24.

9. The method of claim 1, wherein the anti-Cif VHH molecule comprises:
g) a CDR1 comprising SEQ ID NO:26, a CDR2 comprising SEQ ID NO:27 and a CDR3 comprising SEQ ID NO:28.

10. The method of claim 1, wherein the anti-Cif VHH molecule comprises:
h) a CDR1 comprising SEQ ID NO:30, a CDR2 comprising SEQ ID NO:31 and a CDR3 comprising SEQ ID NO:32.

11. The method of claim 1, wherein the anti-Cif VHH molecule comprises:
i) a CDR1 comprising SEQ ID NO:34, a CDR2 comprising SEQ ID NO:35 and a CDR3 comprising SEQ ID NO:36.

12. The method of claim 1, wherein the anti-Cif VHH molecule comprises:
j) a CDR1 comprising SEQ ID NO:38, a CDR2 comprising SEQ ID NO:39 and a CDR3 comprising SEQ ID NO:40.

13. The method of claim 1, wherein the anti-Cif VHH molecule comprises:
k) a CDR1 comprising SEQ ID NO:42, a CDR2 comprising SEQ ID NO:43 and a CDR3 comprising SEQ ID NO:44.

14. The method of claim 1, wherein the anti-Cif VHH molecule comprises:
l) a CDR1 comprising SEQ ID NO:46, a CDR2 comprising SEQ ID NO:47 and a CDR3 comprising SEQ ID NO:48.

15. The method of claim 1, wherein the anti-Cif VHH molecule comprises:
m) a CDR1 comprising SEQ ID NO:50, a CDR2 comprising SEQ ID NO:51 and a CDR3 comprising SEQ ID NO:52.

16. The method of claim 1, wherein the anti-Cif VHH molecule comprises:
o) a CDR1 comprising SEQ ID NO:58, a CDR2 comprising SEQ ID NO:59 and a CDR3 comprising SEQ ID NO:60.

17. The method of claim 1, wherein the anti-Cif VHH molecule comprises:
p) a CDR1 comprising SEQ ID NO:62, a CDR2 comprising SEQ ID NO:63 and a CDR3 comprising SEQ ID NO:64.

18. The method of claim 1, wherein the anti-Cif VHH molecule comprises:
q) a CDR1 comprising SEQ ID NO:66, a CDR2 comprising SEQ ID NO:67 and a CDR3 comprising SEQ ID NO:68.

19. The method of claim 1, wherein the anti-Cif VHH molecule comprises:
r) a CDR1 comprising SEQ ID NO:70, a CDR2 comprising SEQ ID NO:71 and a CDR3 comprising SEQ ID NO:72.

* * * * *